US011524941B2

(12) United States Patent
Wu et al.

(10) Patent No.: US 11,524,941 B2
(45) Date of Patent: Dec. 13, 2022

(54) PYRAZOLE COMPOUNDS AS LSD1 INHIBITORS AND APPLICATIONS THEREOF

(71) Applicant: MEDSHINE DISCOVERY INC., Jiangsu (CN)

(72) Inventors: Lingyun Wu, Shanghai (CN); Lele Zhao, Shanghai (CN); Jianjun Sun, Shanghai (CN); Zhen Zhan, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 17/460,662

(22) Filed: Aug. 30, 2021

(65) Prior Publication Data

US 2022/0064126 A1 Mar. 3, 2022

(30) Foreign Application Priority Data

Aug. 31, 2020 (CN) ......................... 202010893326.7

(51) Int. Cl.

*C07D 231/12* (2006.01)
*C07D 401/06* (2006.01)
*C07D 401/04* (2006.01)
*C07D 487/04* (2006.01)
*C07D 403/12* (2006.01)
*C07D 403/06* (2006.01)
*C07D 471/10* (2006.01)
*C07D 401/14* (2006.01)

(52) U.S. Cl.

CPC ......... *C07D 231/12* (2013.01); *C07D 401/04* (2013.01); *C07D 401/06* (2013.01); *C07D 401/14* (2013.01); *C07D 403/06* (2013.01); *C07D 403/12* (2013.01); *C07D 471/10* (2013.01); *C07D 487/04* (2013.01)

(58) Field of Classification Search

None

See application file for complete search history.

(56) References Cited

PUBLICATIONS

Jul. 11, 2022, Chinese Office Action issued in Chinese Patent Application No. 2021109960209.

Xueshun Wang, Boshi Huang, Takayoshi Suzuki et al., Epigenomics, 2015, 1379-1396.

Adrian Bird, Nature, 2007, 396-398.

James T Lynch, William J Harris & Tim C P Somervaille, Expert Opin. Ther. Targets, 2012, 1239-1249.

Pete Stavropoulos, Günter Blobel, André Hoelz, Nature Structral & Molecular Biology, 2006, 626-632.

Yong Chen, Yuting Yang, Feng Wang et al., Proceedings of the National Academy of Sciences Biochemistry, 2006, 13956-13961.

Ruchi Anand, Ronen Marmorstein, Journal of Biological Chemistry, 2007, 35425-35429.

Eric Metzger, Melanie Wissmann, Na Yin et al., Nature, 2005, 436-439.

Yi Chao Zheng, Jinlian Ma, Zhiru Wang, Medicinal Research Reviews, 2015, 1032-1071.

Zheng Y C, Yu B, Chen Z S, et al. Epigenomics, 2016, 8, 651-666.

Yujiang Shi, Fei Lan, Caitlin Matson, Cell, 2004, 941-953.

Hosseini A, Minucci S. Epigenomics, 2017, 9, 1123-1142.

Daniel P. Mould, Alison E. McGonagle, Daniel H. Wiseman et al., Medicinal Research Reviews, 2015, 586-618.

*Primary Examiner* — Samantha L Shterengarts

(74) *Attorney, Agent, or Firm* — Harness, Dickey & Pierce, P.L.C.

(57) ABSTRACT

Disclosed are a class of pyrazole compounds and applications thereof in the preparation of a medicament for treating related diseases. Specifically, related are a compound represented by formula (II) and a pharmaceutically acceptable salt thereof.

(II)

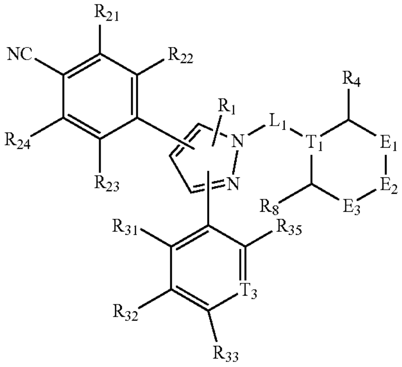

18 Claims, No Drawings

PYRAZOLE COMPOUNDS AS LSD1 INHIBITORS AND APPLICATIONS THEREOF

CROSS-REFERENCE TO RELATED APPLICATIONS

This application claims priority to Chinese Patent Application No. CN2020108933267 filed on Aug. 31, 2020. The entire disclosure of the above application is incorporated herein by reference.

FIELD

The present disclosure relates to a class of pyrazole compounds and applications thereof in the preparation of a medicament for treating related diseases. Specifically, it relates to a compound represented by formula (II) and a pharmaceutically acceptable salt thereof.

BACKGROUND

Post-translational modifications of histone, including methylation, acetylation, phosphorylation and ubiquitination and other processes, are important regulation means of epigenetics, which affect gene expression by changing chromatin structure [Xueshun Wang, Boshi Huang, Takayoshi Suzuki et al., Epigenomics, 2015, 1379-1396;]. Although these modifications do not alter the basic sequence of DNA, such epigenetic changes may persist through cell division throughout the cellular life cycle or cell iteration process [Adrian Bird, Nature, 2007, 396-398]. Therefore, the abnormal function of epigenetics is closely associated with the pathological processes of various diseases [James T Lynch, William J Harris & Tim C P Somervaille, Expert Opin. Ther. Targets, 2012, 1239-1249], such as various solid tumors, hematologic tumors, viral infections, neurological abnormalities, and other diseases. Therefore, epigenetics has now become a research hotspot in the field of drug research and development. The methylation status of histones is regulated by a combination of histone methyltransferases and histone demethylases. Lysine specific demethylase 1 (LSD1, also known as KDM1A) is the first reported histone lysine demethylase. By regulating the methylation state of histone lysine, it is widely involved in transcription regulation and affects many physiological processes such as cell proliferation and differentiation and pluripotency of embryonic stem cells. [Yujiang Shi, Fei Lan, Caitlin Matson et al., Cell, 2004, 941-953] [Daniel P. Mould, Alison E. McGonagle, Daniel H. Wiseman et al., Medicinal Research Reviews, 2015, 586-618]. LSD1 structure consists of three main parts: the N-terminal SWIRM structural domain, the C-terminal amino oxidase structural domain (AOL) and the central Tower domain. [Ruchi Anand, Ronen Marmorstein, Journal of Biological Chemistry, 2007, 35425-35429]. The C-terminal structural domain of amino oxidase includes two active pockets, one for FAD binding and the other for recognition and binding to the substrate [Pete Stavropoulos, Gunter Blobel, Andre Hoelz, Nature Structral & Molecular Biology, 2006, 626-632]. The function of the SWIRM structural domain has not been clearly concluded; it is not directly involved in FAD or substrate binding, but mutation or removal of this region decreases LSD1 activity, so it is speculated that this region may affect the function of active region by adjusting conformation. [Yong Chen, Yuting Yang, Feng Wang et al., Biochemistry, 2006, 13956-13961]. Tower domain is the binding domain between LSD1 and other protein factors. When LSD1 binds to different protein factors, it acts on different substrates and thus playing different regulatory roles in histone and gene expression. For example, after LSD1 binds to CoREST, it will preferentially act on histone H3K4, remove activation-related histone markers and inhibit gene transcription through demethylation; after binding to androgen receptor protein, the recombinant LSD1 preferentially acts on H3K9 and activates the transcription of androgen receptor-related genes through demethylation [Ruchi Anand, Ronen Marmorstein, Journal of Biological Chemistry, 2007, 35425-35429; Eric Metzger, Melanie Wissmann, Na Yin et al., Nature, 2005, 436-439.]. In addition, LSD1 also regulates the methylation status of some non-histone substrates, including tumor suppressor gene p53, DNA methyltransferase 1 (DNMT1) and the like. [Yi Chao Zheng, Jinlian Ma, Zhiru Wang, Medicinal Research Reviews, 2015, 1032-1071].

LSD1 is a FAD-dependent amino oxidase in which proton transfer is considered as its most likely oxidation mechanism [Zheng Y C, Yu B, Chen Z S, et al. Epigenomics, 2016, 8, 651-666.]. Firstly, the N—$CH_3$ bond of the substrate is converted into an imine bond by proton transfer, and this imine ion intermediate undergoes a hydrolysis reaction to produce a demethylated amine on one side and formaldehyde on the other side. In this catalytic cycle, FAD is reduced to FADH2, and then oxidized back to FAD by a molecule of oxygen, and a molecule of $H_2O_2$ is generated at the same time [Yujiang Shi, Fei Lan, Caitlin Matson, Cell, 2004, 941-953].

LSD1 is abnormally expressed in many different types of tumors. LSD1 is highly expressed in acute myeloid leukemia (AML) subtype, which is an important factor to maintain the potential of leukemia stem cell (LSC). LSD1 is highly expressed in a variety of solid tumors such as lung cancer, breast cancer, prostate cancer, liver cancer and pancreatic cancer, and is strongly associated with poor prognosis of the tumors. LSD1 inhibits the expression of cadherin, which is closely related to tumor invasion and epithelial-mesenchymal transition (EMT) [Hosseini A, Minucci S. Epigenomics, 2017, 9, 1123-1142.].

At present, no LSD1 inhibitor has been approved for marketing, and 8 drugs are in clinical research stage, mainly used for the treatment of hematologic tumor, small cell lung cancer and Ewing's sarcoma and other diseases. However, in the face of a huge unmet market, the field still needs candidates with better activity and better pharmacokinetic parameters to advance to clinical trials to meet therapeutic needs.

SUMMARY

The present disclosure provides a compound represented by formula (II) or a pharmaceutically acceptable salt thereof, (II)

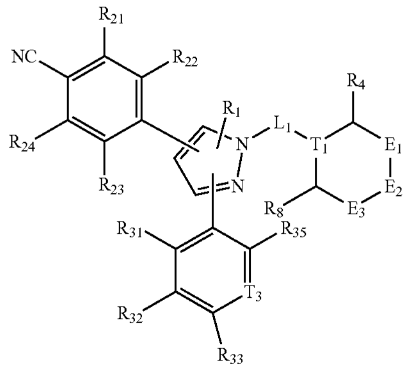

wherein, $L_1$ is single bond, —$CH_2$—, —$CH_2$—C(═O)— or —$CH_2$—C(═O)—NH—;

$T_1$ is $CR_{t1}$ or N;

$T_3$ is $CR_{34}$ or N;

$E_1$ is single bond, —$C(R_5)_2$— or —$C(R_5)_2C(R_5)_2$—;

$E_2$ is O, —$NR_6$— or —$C(R_{61})_2$—;

$E_3$ is single bond, —$C(R_7)_2$— or —$C(R_7)_2C(R_7)_2$—;

$R_1$ is H, halogen or $C_{1-3}$ alkyl, wherein the $C_{1-3}$ alkyl is optionally substituted by one, two or three $R_a$;

$R_{21}$, $R_{22}$, $R_{23}$ and $R_{24}$ are independently H or halogen;

$R_{31}$, $R_{32}$, $R_{33}$, $R_{34}$ and $R_{35}$ are independently H, halogen, $C_{1-3}$ alkyl or $C_{1-3}$ alkoxyl, wherein the $C_{1-3}$ alkyl and $C_{1-3}$ alkoxyl are optionally substituted by one, two or three $R_b$;

$R_4$ is H, halogen or $C_{1-3}$ alkyl, wherein the $C_{1-3}$ alkyl is optionally substituted by one, two or three $R_c$;

$R_5$ is independently H, halogen, OH, $NH_2$ or $C_{1-3}$ alkyl, wherein the $C_{1-3}$ alkyl is optionally substituted by one, two or three $R_d$;

$R_6$ is H or $C_{1-3}$ alkyl, wherein the $C_{1-3}$ alkyl is optionally substituted by one, two or three $R_e$;

$R_{61}$ is independently H, halogen, OH, $NH_2$ or $C_{1-3}$ alkyl, wherein the $C_{1-3}$ alkyl is optionally substituted by one, two or three $R_f$;

$R_7$ is independently H, halogen, OH, $NH_2$ or $C_{1-3}$ alkyl, wherein the $C_{1-3}$ alkyl is optionally substituted by one, two or three $R_g$;

$R_8$ is independently H, halogen, OH, $NH_2$ or $C_{1-3}$ alkyl, wherein the $C_{1-3}$ alkyl is optionally substituted by one, two or three $R_h$;

or, $R_{32}$ and $R_{33}$ are attached together so that the structural unit

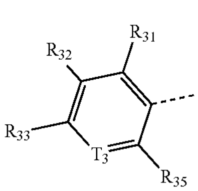 is 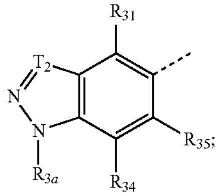

$T_2$ is $CR_{t2}$ or N;

$R_{3a}$ is H or $C_{1-3}$ alkyl, wherein the $C_{1-3}$ alkyl is optionally substituted by one, two or three $R_i$;

or, $R_5$ and $R_{61}$ are attached together so that the structural unit

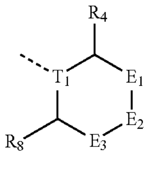 is 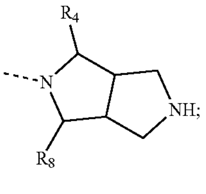

or, two $R_{61}$ are attached together with the C atom to which they are attached so that the structural unit

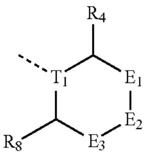 is 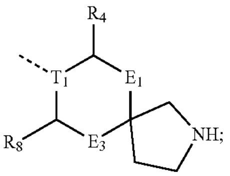

or, $R_4$ and $R_7$ are attached together so that the structural unit

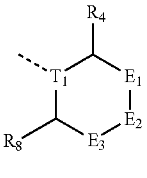 is 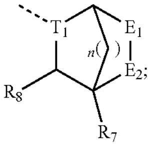

or, $R_4$ and $R_8$ are attached together so that the structural unit

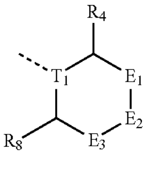 is 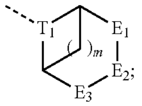

$R_{t1}$ is H or OH;

$R_{t2}$ is H or halogen;

$R_a$, $R_b$, $R_c$, $R_d$, $R_e$, $R_f$, $R_g$ and $R_h$ are independently halogen, OH or $NH_2$;

$R_1$ is independently halogen, OH or $CH_3$;

n is 1 or 2;

m is 1 or 2.

The present disclosure provides a compound represented by formula (I) or a pharmaceutically acceptable salt thereof, (I)

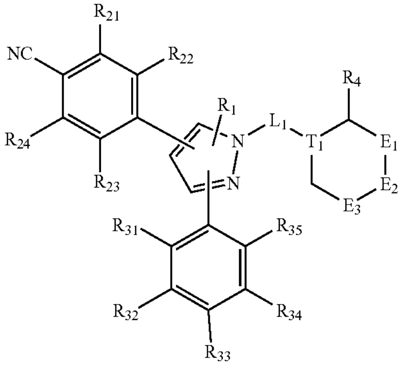

wherein, $L_1$ is single bond, —$CH_2$— or —$CH_2$—C(═O)—;

$T_1$ is CH or N;

$E_1$ is single bond, —$C(R_5)_2$— or —$C(R_5)_2C(R_5)_2$—;

$E_2$ is —$NR_6$— or —$C(R_{61})_2$—;

$E_3$ is single bond, —$C(R_7)_2$— or —$C(R_7)_2C(R_7)_2$—;

$R_1$ is H, halogen or $C_{1-3}$ alkyl, wherein the $C_{1-3}$ alkyl is optionally substituted by one, two or three $R_a$;

$R_{21}$, $R_{22}$, $R_{23}$ and $R_{24}$ are independently H or halogen;

$R_{31}$, $R_{32}$, $R_{33}$, $R_{34}$ and $R_{35}$ are independently H, halogen, $C_{1-3}$ alkyl or $C_{1-3}$ alkoxyl, wherein the $C_{1-3}$ alkyl and $C_{1-3}$ alkoxyl are independently optionally substituted by one, two or three $R_b$;

$R_4$ is H, halogen or $C_{1-3}$ alkyl, wherein the $C_{1-3}$ alkyl is optionally substituted by one, two or three $R_e$;

$R_5$ is independently H, halogen, OH, $NH_2$ or $C_{1-3}$ alkyl, wherein the $C_{1-3}$ alkyl is optionally substituted by one, two or three $R_d$;

$R_6$ is H or $C_{1-3}$ alkyl, wherein the $C_{1-3}$ alkyl is optionally substituted by one, two or three $R_e$;

$R_{61}$ is independently H, halogen, OH, $NH_2$ or $C_{1-3}$ alkyl, wherein the $C_{1-3}$ alkyl is optionally substituted by one, two or three $R_f$;

$R_7$ is independently H, halogen, OH, $NH_2$ or $C_{1-3}$ alkyl, wherein the $C_{1-3}$ alkyl is optionally substituted by one, two or three $R_g$;

or, $R_4$ and $R_7$ are attached together so that the structural unit

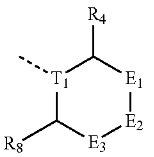

is

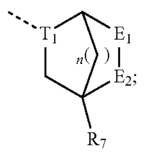

$R_a$, $R_b$, $R_c$, $R_d$, $R_e$, $R_f$ and $R_g$ are independently halogen, OH or $NH_2$;

n is 1 or 2.

In some embodiments of the present disclosure, the compound has the structure represented by formula (I-1), (I-2), (I-3), (I-4) or (I-5):

(I-1)

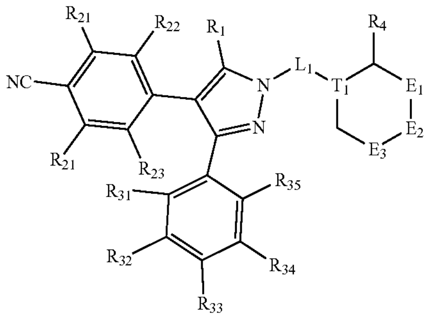

(I-2)

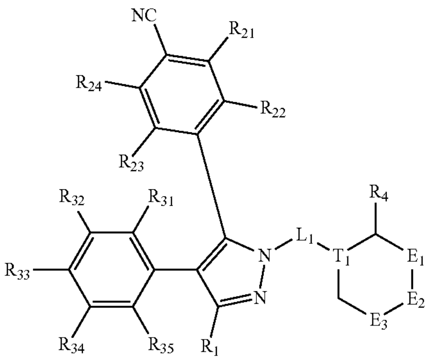

-continued (I-3)

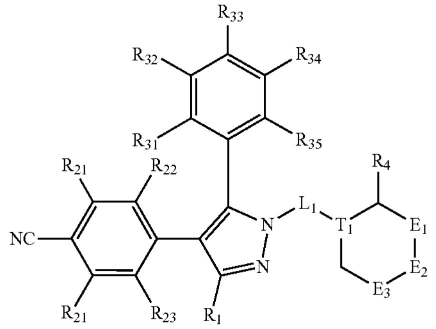

(I-4)

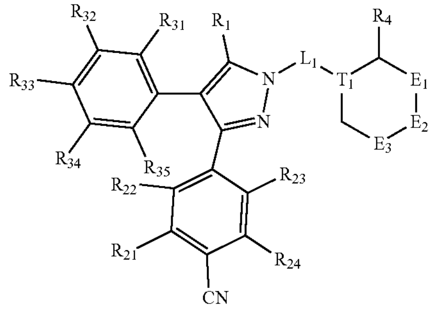

(I-5)

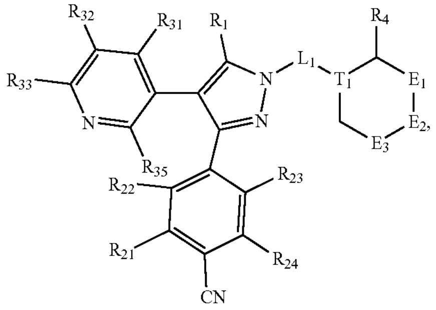

wherein, $L_1$, $T_1$, $E_1$, $E_2$, $E_3$, $R_1$, $R_{21}$, $R_{22}$, $R_{23}$, $R_{24}$, $R_{31}$, $R_{32}$, $R_{33}$, $R_{34}$, $R_{35}$ and $R_4$ are as defined in the present disclosure.

In some embodiments of the present disclosure, $R_1$ is H, F, Cl, Br, I or $CH_3$, wherein the $CH_3$ is optionally substituted by one, two or three $R_a$, other variables are as defined in the present disclosure.

In some embodiments of the present disclosure, $R_1$ is H, F or $CH_3$, other variables are as defined in the present disclosure.

In some embodiments of the present disclosure, $R_{21}$, $R_{22}$, $R_{23}$ and $R_{24}$ are independently H, F, Cl, Br or I, other variables are as defined in the present disclosure.

In some embodiments of the present disclosure, $R_{31}$, $R_{32}$, $R_{33}$, $R_{34}$ and $R_{35}$ are independently H, F, Cl, Br, I, $CH_3$ or $—OCH_3$, wherein the $CH_3$ or $—OCH_3$ is optionally substituted by one, two or three $R_b$, other variables are as defined in the present disclosure.

In some embodiments of the present disclosure, $R_{31}$, $R_{32}$, $R_{33}$, $R_{34}$ and $R_{35}$ are independently H, F, Cl, Br, I, $CH_3$, $CF_3$ or $—OCH_3$, other variables are as defined in the present disclosure.

In some embodiments of the present disclosure, $R_{31}$, $R_{32}$, $R_{33}$, $R_{34}$ and $R_{35}$ are independently H, F, Cl, Br, I, $CH_3$ or $—OCH_3$, other variables are as defined in the present disclosure.

In some embodiments of the present disclosure, $R_4$ is H, F, Cl, Br, I or $CH_3$, wherein the $CH_3$ is optionally substituted by one, two or three $R_c$, other variables are as defined in the present disclosure.

In some embodiments of the present disclosure, $R_4$ is H or $CH_3$, other variables are as defined in the present disclosure.

In some embodiments of the present disclosure, $R_5$ is independently H, F, Cl, Br, I, OH, $NH_2$ or $CH_3$, wherein the $CH_3$ is optionally substituted by one, two or three $R_d$, other variables are as defined in the present disclosure.

In some embodiments of the present disclosure, $R_5$ is independently H or $NH_2$, other variables are as defined in the present disclosure.

In some embodiments of the present disclosure, $R_6$ is H or $CH_3$, wherein the $CH_3$ is optionally substituted by one, two or three $R_e$, other variables are as defined in the present disclosure.

In some embodiments of the present disclosure, $R_6$ is H, other variables are as defined in the present disclosure.

In some embodiments of the present disclosure, $R_{61}$ is independently H, F, Cl, Br, I, OH, $NH_2$ or $CH_3$, wherein the $CH_3$ is optionally substituted by one, two or three $R_f$, other variables are as defined in the present disclosure.

In some embodiments of the present disclosure, $R_{61}$ is independently H or $NH_2$, other variables are as defined in the present disclosure.

In some embodiments of the present disclosure, $R_7$ is independently H, F, Cl, Br, I, OH, $NH_2$ or $CH_3$, wherein the $CH_3$ is optionally substituted by one, two or three $R_g$, other variables are as defined in the present disclosure.

In some embodiments of the present disclosure, $R_7$ is independently H or $NH_2$, other variables are as defined in the present disclosure.

In some embodiments of the present disclosure, $R_g$ is H, other variables are as defined in the present disclosure.

In some embodiments of the present disclosure, the structural unit

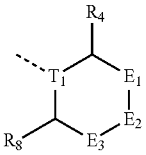

is

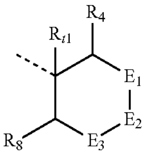

or

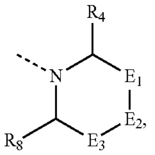

other variables are as defined in the present disclosure.

In some embodiments of the present disclosure, the structural unit

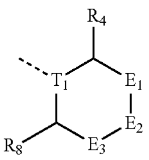

is

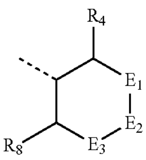

or

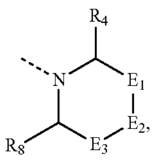

other variables are as defined in the present disclosure.

In some embodiments of the present disclosure, the structural unit

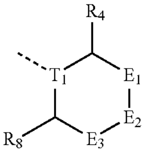

is

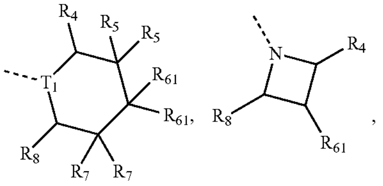

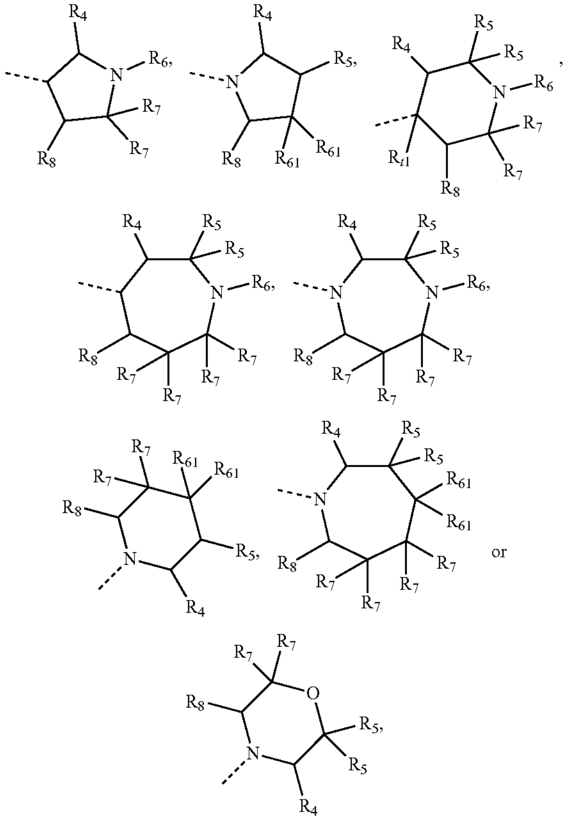

or other variables are as defined in the present disclosure.

In some embodiments of the present disclosure, the structural unit

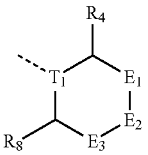

is

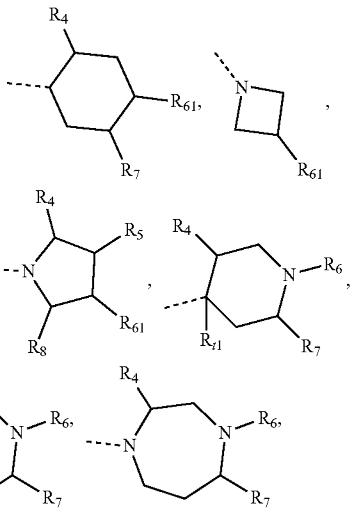

-continued

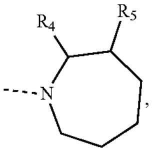,
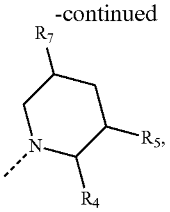
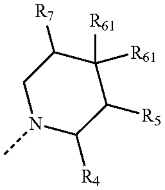 or
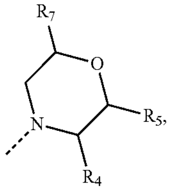

other variables are as defined in the present disclosure.

In some embodiments of the present disclosure, the structural unit

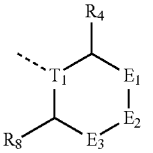 is
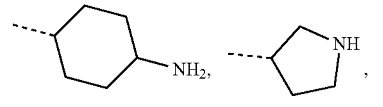
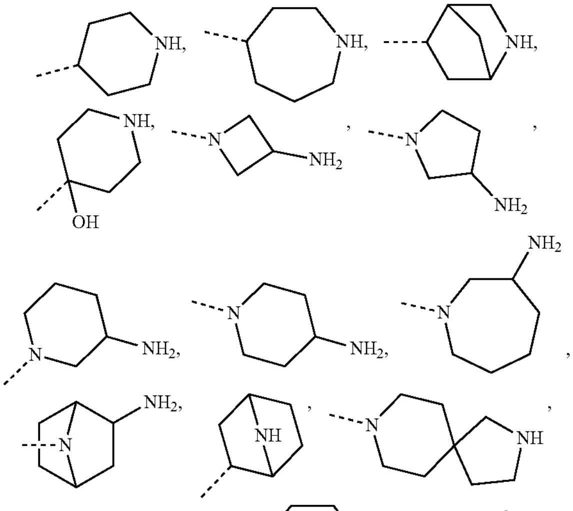
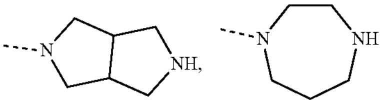 or
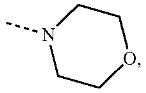

other variables are as defined in the present disclosure.

In some embodiments of the present disclosure, the structural unit

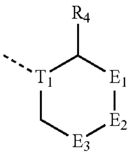 is
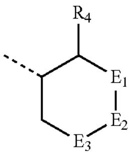 or
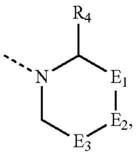

other variables are as defined in the present disclosure.

In some embodiments of the present disclosure, the structural unit

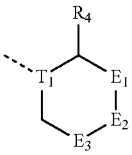 is
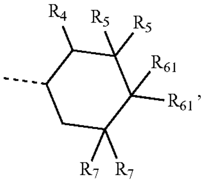
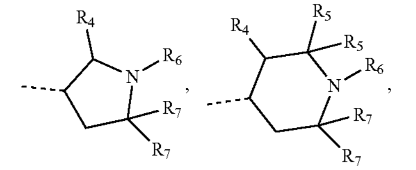
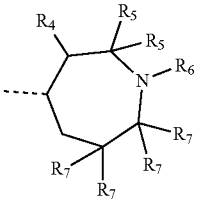 or
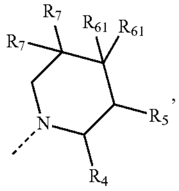

other variables are as defined in the present disclosure.

In some embodiments of the present disclosure, the structural unit

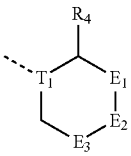 is
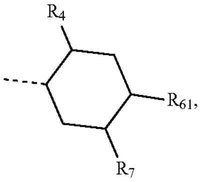
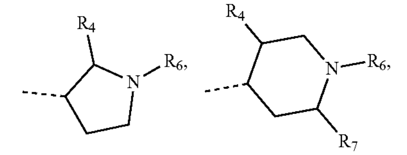
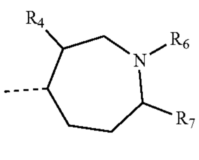 or
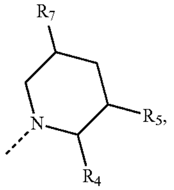

other variables are as defined in the present disclosure.

In some embodiments of the present disclosure, the structural unit

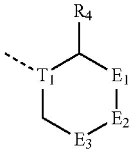 is
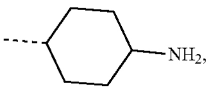
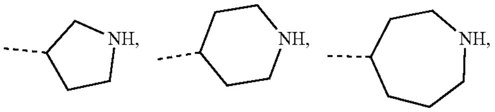

-continued
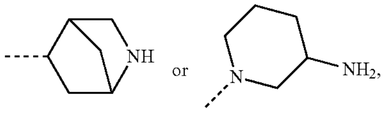
other variables are as defined in the present disclosure.
There are also embodiments of the present disclosure that result from arbitrary combination of the above variables.
In some embodiments of the present disclosure, the compound or the pharmaceutically acceptable salt thereof, wherein, the compound is
(I-1A)
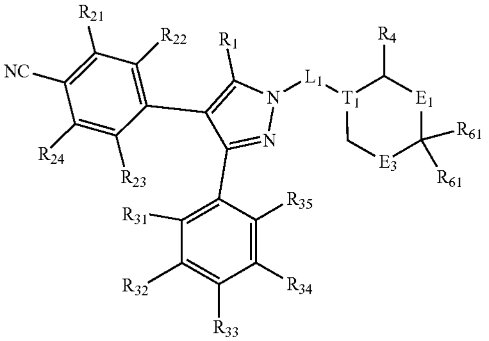
(I-1B)
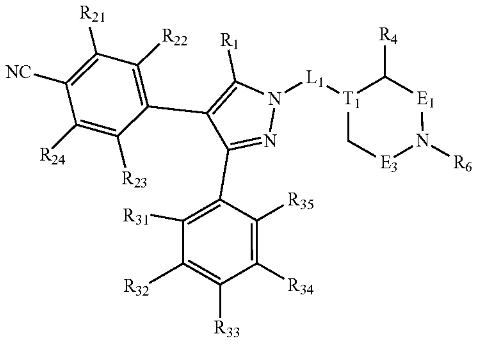
(I-2A)
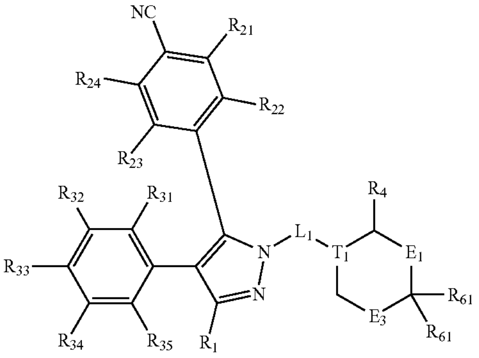
-continued
(I-2B)
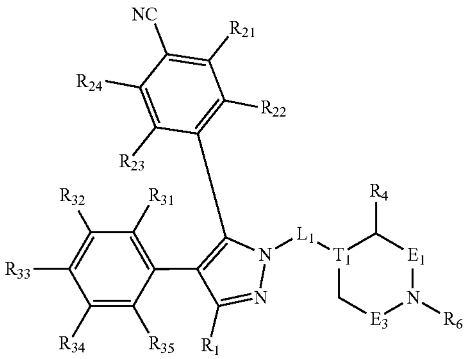
(I-2C)
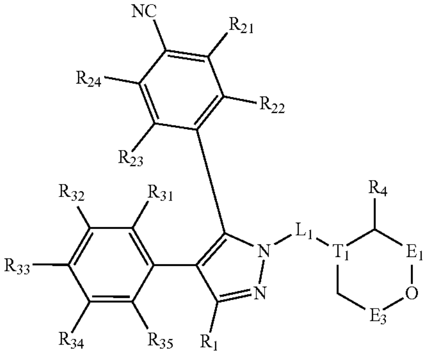
(I-3A)
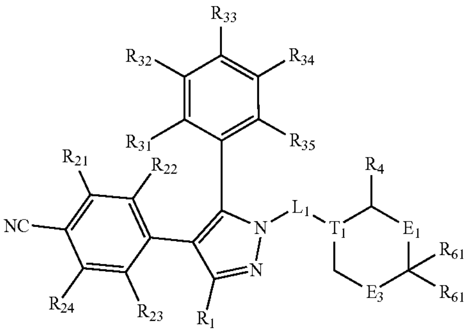
(I-3B)
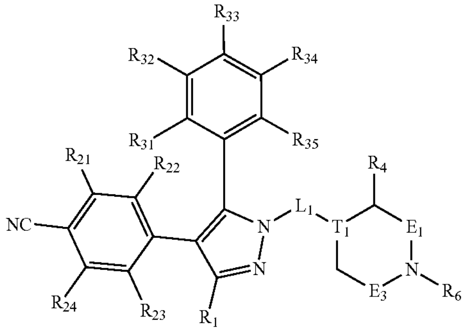

-continued (I-4A)

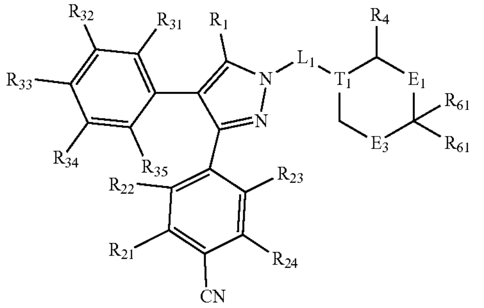

(I-4B)

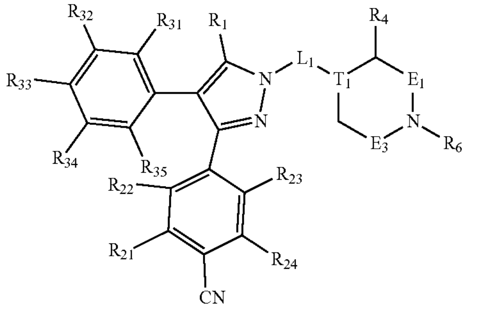

(I-4C)

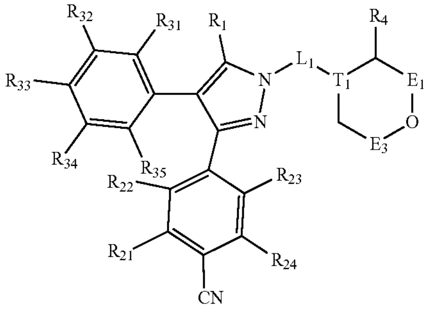

(I-5A)

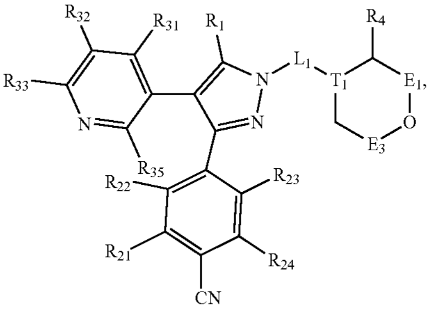

wherein, $L_1$, $T_1$, $E_1$, $E_3$, $R_1$, $R_{21}$, $R_{22}$, $R_{23}$, $R_{24}$, $R_{31}$, $R_{32}$, $R_{33}$, $R_{34}$, $R_{35}$, $R_4$, $R_6$ and $R_{61}$ are as defined in the present disclosure.

In some embodiments of the present disclosure, the compound or the pharmaceutically acceptable salt thereof, wherein, the compound is (I-4A-1)

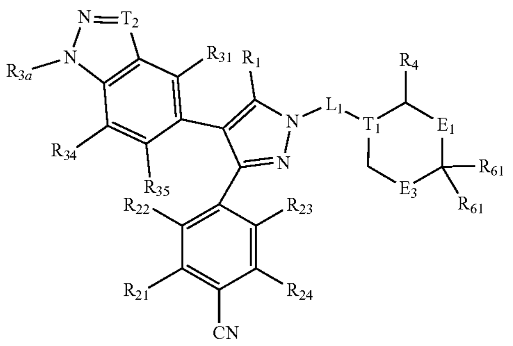

(I-4B-1)

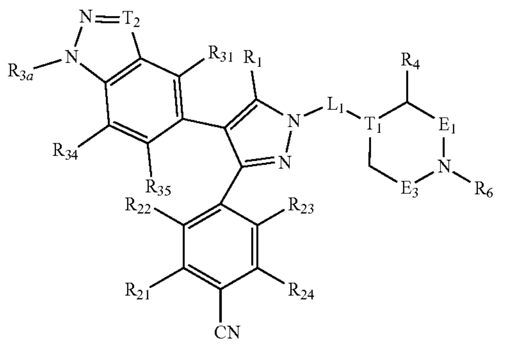

wherein, $L_1$, $T_1$, $T_2$, $E_1$, $E_3$, $R_1$, $R_{21}$, $R_{22}$, $R_{23}$, $R_{24}$, $R_{31}$, $R_{34}$, $R_{35}$, $R_{3a}$, $R_4$, $R_6$ and $R_{61}$ are as defined in the present disclosure.

The present disclosure also provides a compound represented by the following formula or a pharmaceutically acceptable salt thereof,

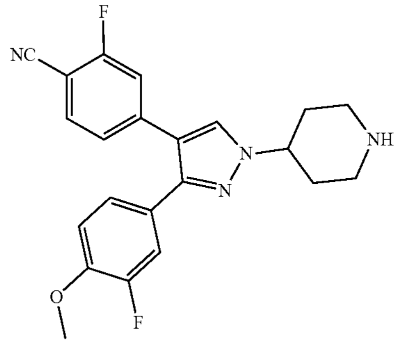

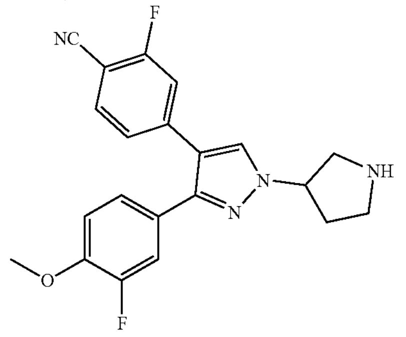

-continued
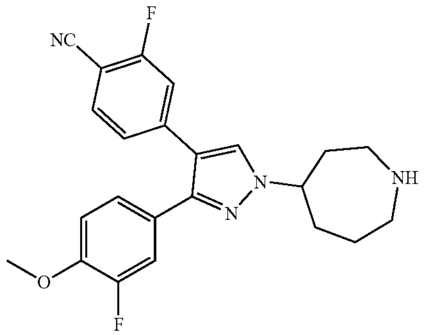
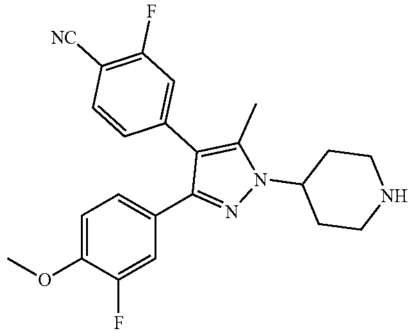
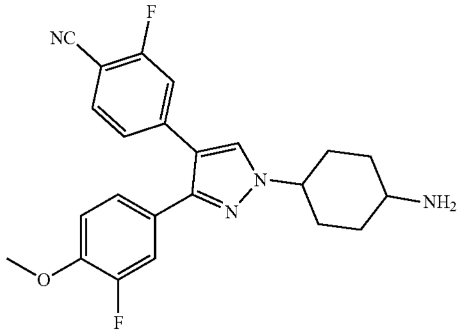
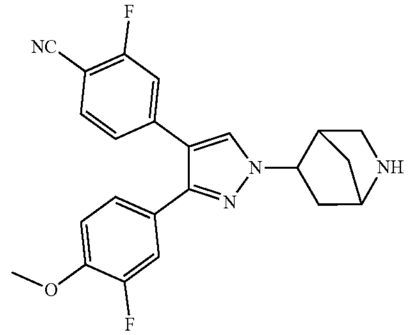
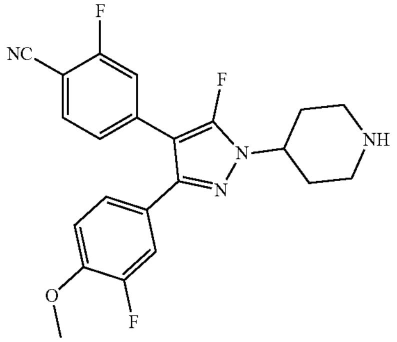
-continued
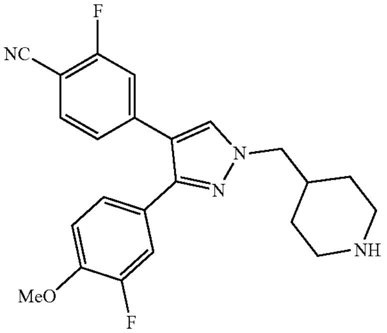
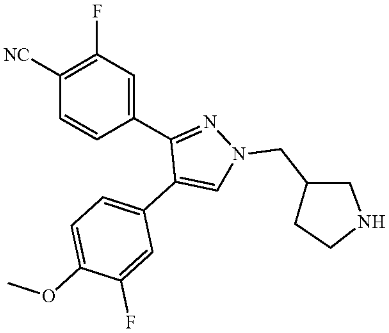
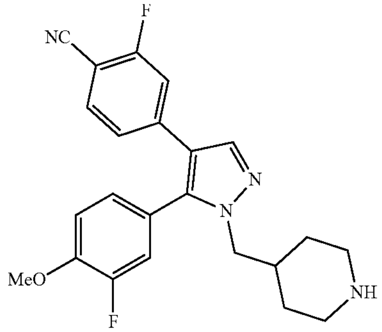
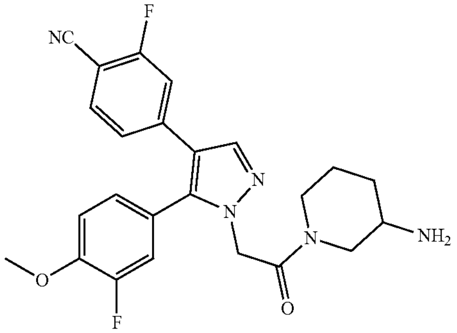
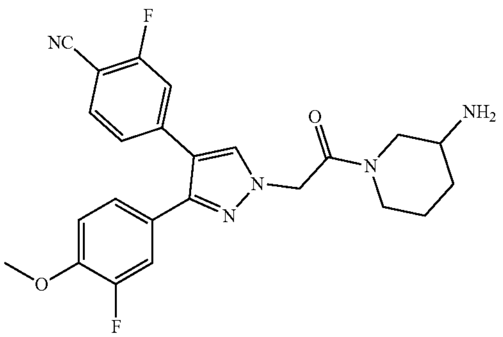

-continued
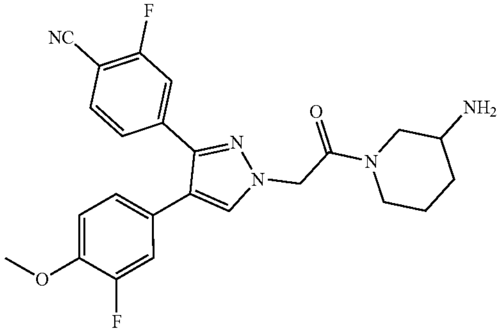
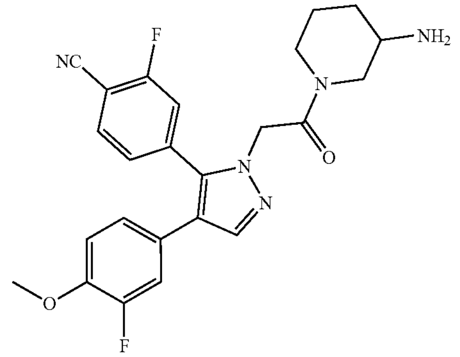
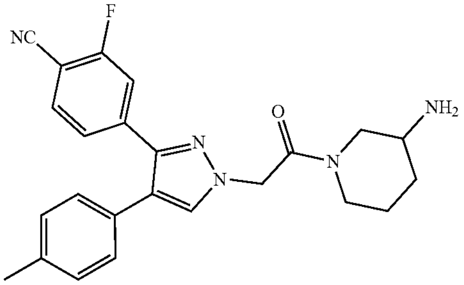
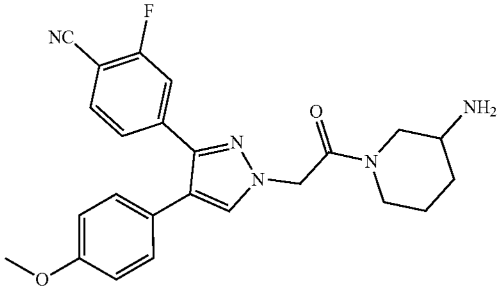
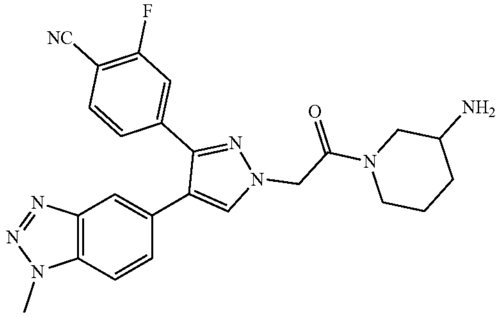
-continued
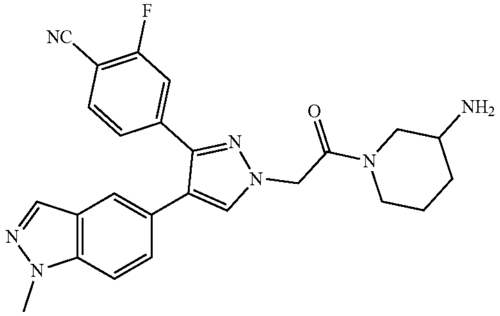
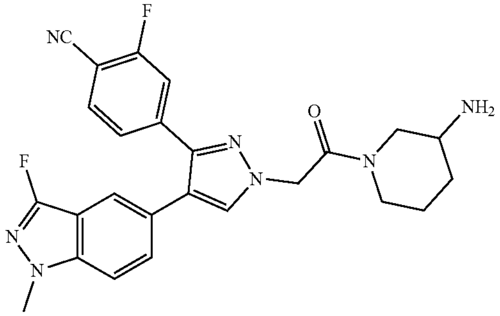
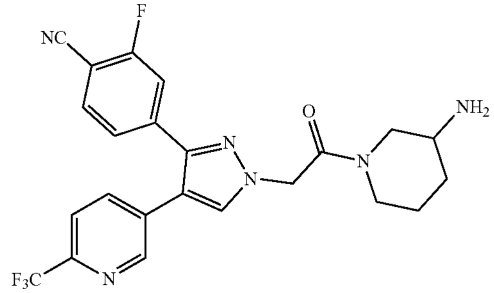
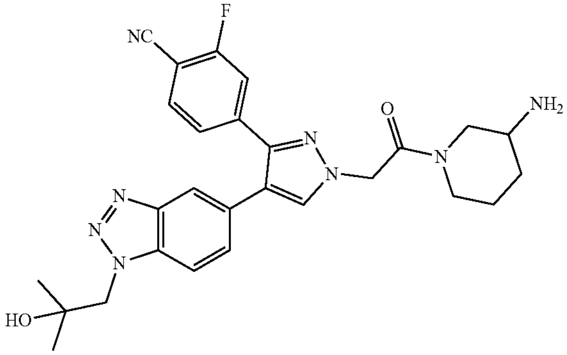
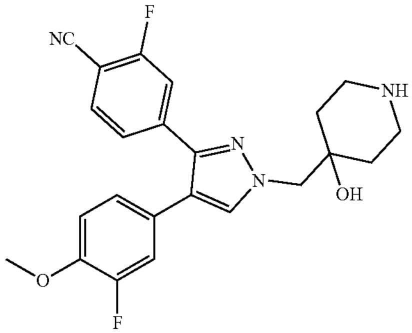

-continued
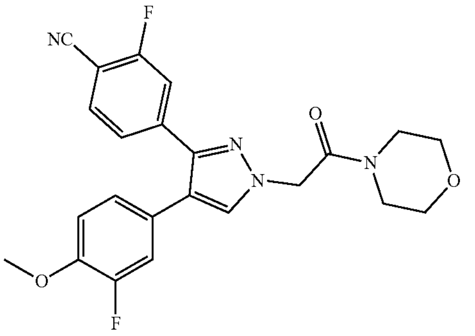
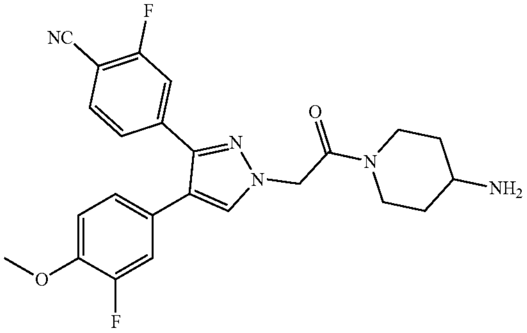
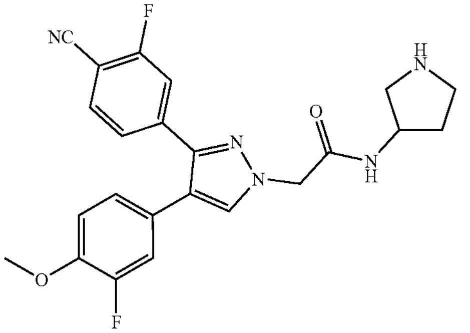
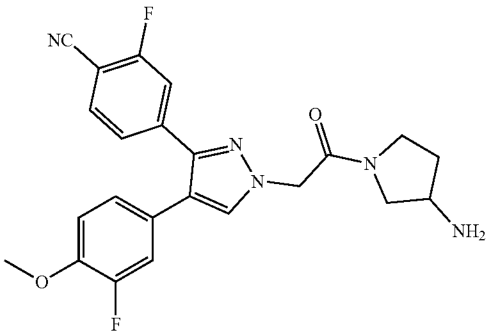
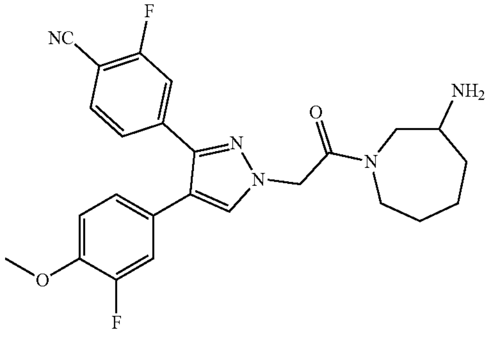
-continued
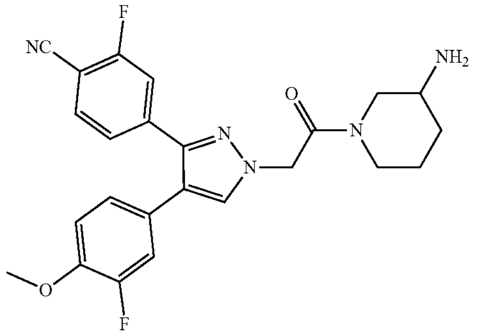
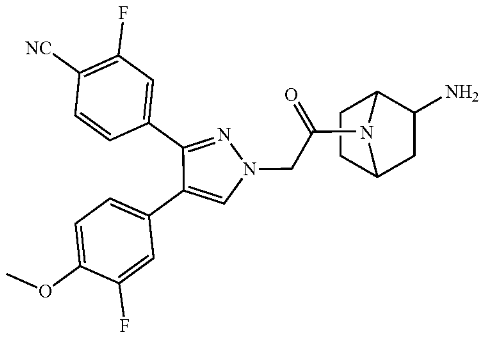
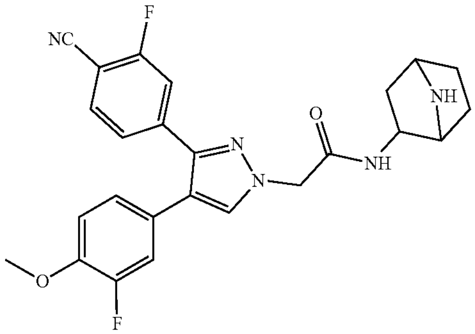
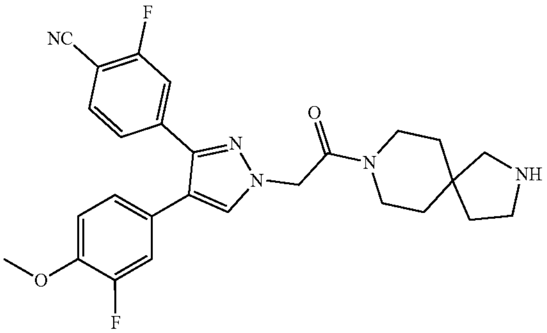
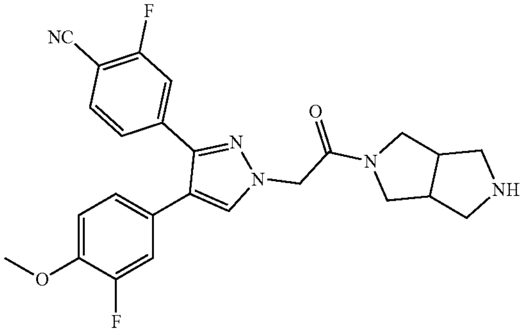

-continued
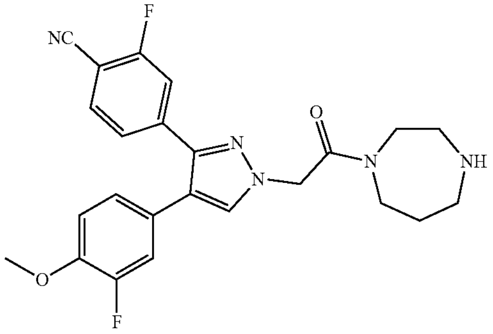
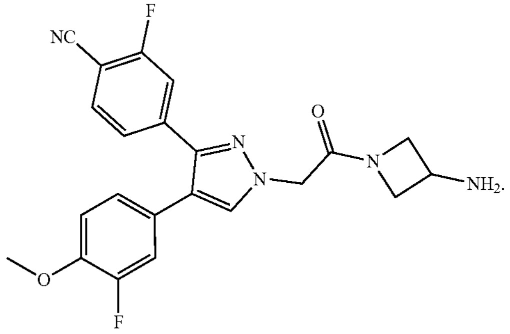
In some embodiments of the present disclosure, the compound or the pharmaceutically acceptable salt thereof, wherein, the compound is
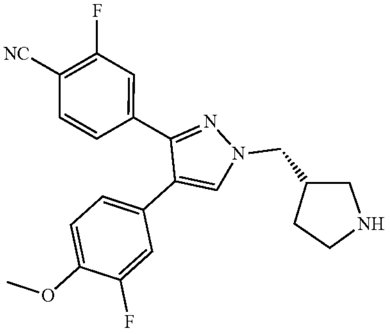
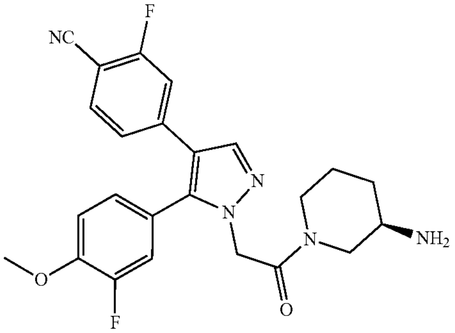
-continued
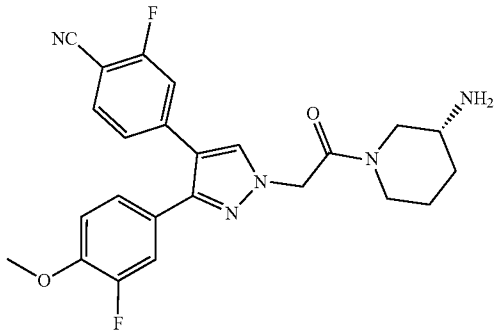
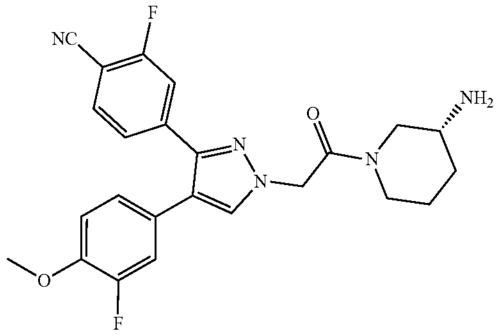
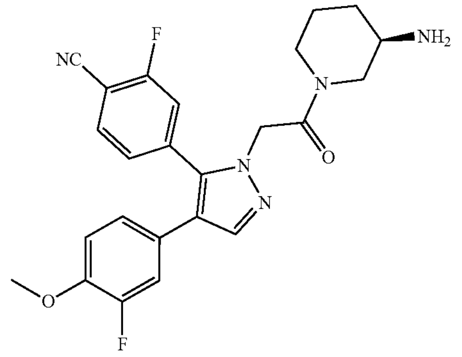
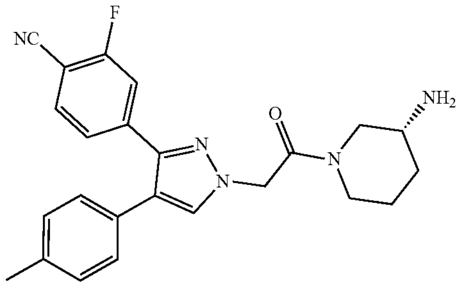
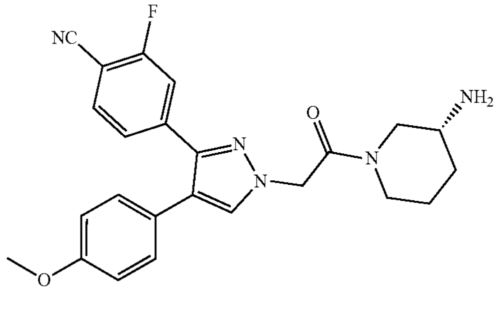

-continued

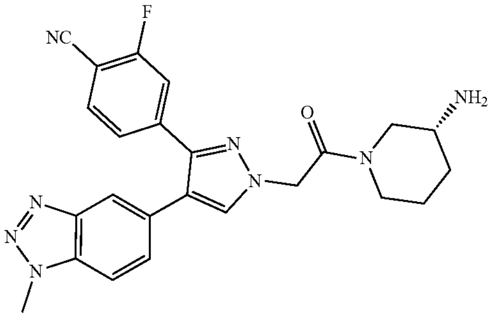

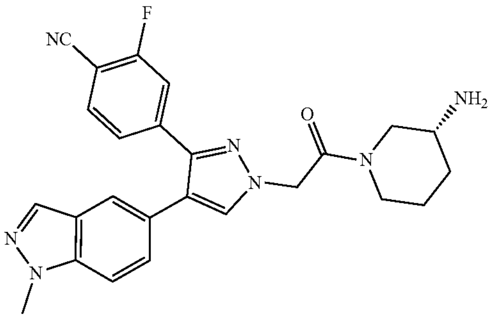

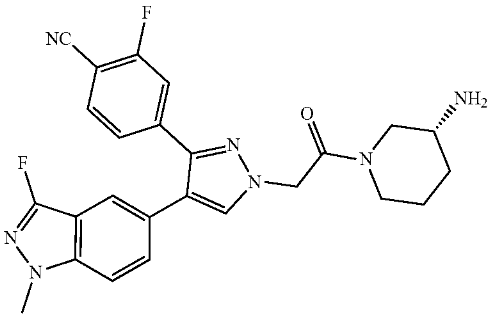

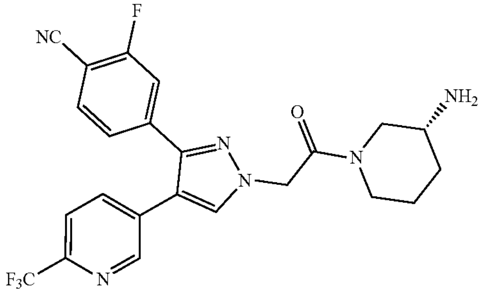

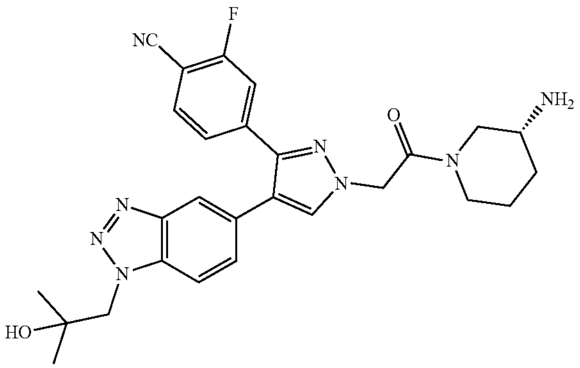

-continued

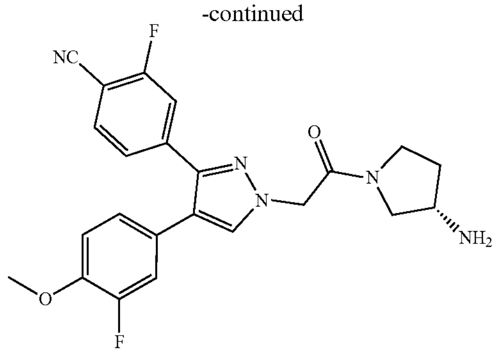

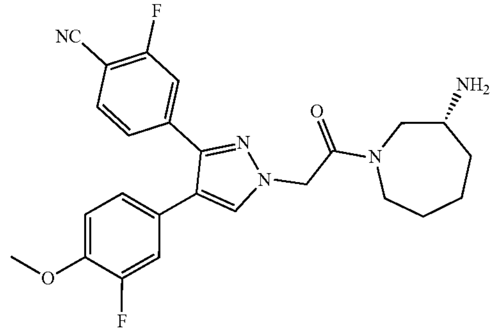

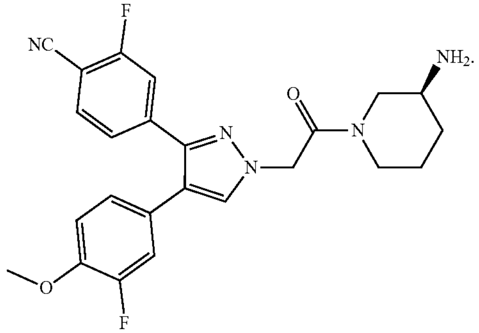

The present disclosure also provides the compound or the pharmaceutically acceptable salt thereof, wherein the pharmaceutically acceptable salt is hydrochloride.

The present disclosure also provides a use of the compound or the pharmaceutically acceptable salt thereof in the preparation of a medicament for treating LSD1 related diseases.

The present disclosure also provides a pharmaceutical composition, which comprises the compound or the pharmaceutically acceptable salt thereof, and one or more pharmaceutically acceptable carriers.

The present disclosure also provides a method for inhibiting LSD1 in-vitro, in-vivo or ex-vivo, which comprises administering the compound or the pharmaceutically acceptable salt thereof in a sufficient amount to inhibit LSD1.

The present disclosure also provides a method for treating a subject who has cancer, which comprises administering to the subject a therapeutically effective amount of the compound or the pharmaceutically acceptable salt thereof.

In some embodiments of the present disclosure, the cancer is acute myeloid leukemia (AML), acute lymphoblastic leukemia (ALL), small cell lung cancer (SCLC), non-small cell lung cancer (NSCLC), adult neuroblastoma, small round blue cell tumor, glioblastoma, prostate cancer, breast cancer, ovarian cancer, gastrointestinal cancer, liver cancer, bladder cancer, lung cancer, and/or melanoma.

DETAILED DESCRIPTION

Technical Effect

The compounds of the present disclosure possess a relatively good inhibitory activity on LSD1.

Definitions

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and or "(±)" refers to racemic.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ) a wave line ( ) is used to represent a wedged dashed bond ( ) or a wedged dashed bond ( ), or the wave line ( ) is used to represent a straight solid bond ( ) and a straight dashed bond ( ).

Unless otherwise specified, when double bond structure, such as carbon-carbon double bond, carbon-nitrogen double bond, and nitrogen-nitrogen double bond, exists in the compound, and each of the atoms on the double bond is connected to two different substituents (including the condition where a double bond contains a nitrogen atom, the lone pair of electrons attached on the nitrogen atom is regarded as a substituent connected), if the atom on the double bond in the compound is connected to its substituent by a wave line ( ), this refers to the (Z) isomer, (E) isomer or a mixture of two isomers of the compound. For example, the following formula (A) means that the compound exists as a single isomer of formula (A-1) or formula (A-2) or as a mixture of two isomers of formula (A-1) and formula (A-2); the following formula (B) means that the compound exists in the form of a single isomer of formula (B-1) or formula (B-2) or in the form of a mixture of two isomers of formula (B-1) and formula (B-2). The following formula (C) means that the compound exists as a single isomer of formula (C-1) or formula (C-2) or as two a mixture of two isomers of formula (C-1) and formula (C-2).

(A)

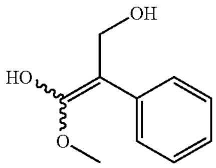

(A-1)

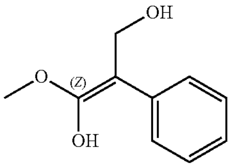

-continued (A-2)

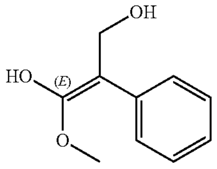

(B)

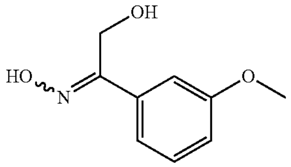

(B-1)

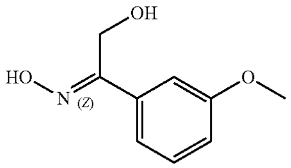

(B-2)

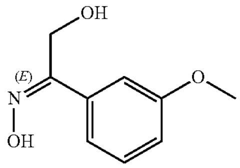

(C)

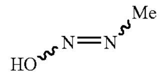

(C-1)

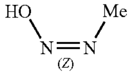

(C-2)

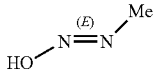

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure. The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is O, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

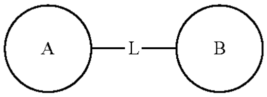

is -M-W—, then -M-W— can link ring A and ring B to form

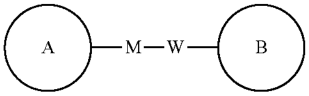

in the direction same as left-to-right reading order, and form

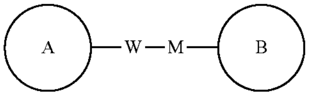

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to meet the corresponding valence. The chemical bond between the site and other groups can be represented by a straight solid bond (), a straight dashed bond () or a wavy line (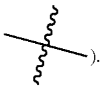).

For example, the straight solid bond in —$OCH_3$ means that it is linked to other groups through the oxygen atom in the group; the straight dashed bonds in

means that it is linked to other groups through the two ends of nitrogen atom in the group; the wave lines in

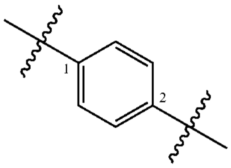 [SMILES: *c1ccc(*)cc1]

means that the phenyl group is linked to other groups through carbon atoms at position 1 and position 2;

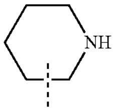

means that it can be linked to other groups through any linkable sites on the piperidinyl by one chemical bond, including at least four types of linkage, including

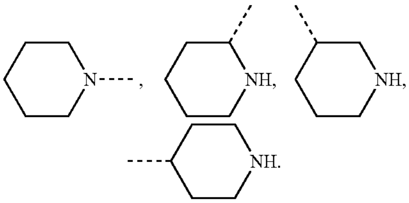

Even though the H atom is drawn on the —N—,

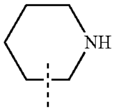

still includes the linkage of

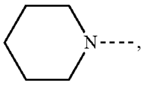

merely when one chemical bond was connected, the H of this site will be reduced by one to the corresponding monovalent piperidinyl.

Unless otherwise specified, the term "$C_{1-4}$ alkyl" refers to a linear or branched saturated hydrocarbon group containing 1 to 4 carbon atoms. The $C_{1-4}$ alkyl includes $C_{1-2}$, $C_{1-3}$ and $C_{2-3}$ alkyl groups and the like. It can be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), butyl (including n-butyl, isobutyl, s-butyl, and t-butyl), etc.

Unless otherwise specified, the term "$C_{1-3}$ alkyl" refers to a linear or branched saturated hydrocarbon group having 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_3$ and $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "halo" or "halogen" by itself or as part of another substituent refers to fluorine, chlorine, bromine or iodine atom.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n membered to n+m membered means that the number of atoms on the ring is from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring, etc.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl, such as benzyl (Bn), trityl (Tr), 1,1-bis-(4'-methoxyphenyl) methyl; silyl, such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl, such as methyl, ethyl, and tert-butyl; acyl, such as alkanoyl (e.g., acetyl); arylmethyl, such as benzyl (Bn), p-methoxybenzyl (PMB), 9-fluorenylmethyl (Fm), and diphenylmethyl (benzhydryl, DPM); silyl, such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The structure of the compounds of the present disclosure can be confirmed by conventional methods known to those skilled in the art, and if the disclosure involves an absolute configuration of a compound, then the absolute configuration can be confirmed by means of conventional techniques in the art. For example, in the case of single crystal X-ray diffraction (SXRD), the absolute configuration can be confirmed by collecting diffraction intensity data from the cultured single crystal using a Bruker D8 venture diffractometer with CuKα radiation as the light source and scanning mode: φ/scan, and after collecting the relevant data, the crystal structure can be further analyzed by direct method (Shelxs97).

The solvents used in the present disclosure are commercially available.

The present disclosure uses the following abbreviations: aq refers to water; HATU refers to O-(7-azabenzotriazol-1-yl)-N,N,N,N-tetramethyluronium hexafluorophosphate; EDC refers to N-(3-dimethylaminopropyl)-N-ethylcarbodiimide hydrochloride; m-CPBA refers to 3-chloroperoxybenzoic acid; eq refers to equivalent, equivalents; CDI refers to carbonyl diimidazole; DCM refers to dichloromethane; PE refers to petroleum ether; DIAD refers to diisopropyl azo dicarboxylate; DMF refers to N,N-dimethylformamide; DMSO refers to dimethyl sulfoxide; EtOAc refers to ethyl acetate; EtOH refers to ethanol; MeOH refers to methanol; CBz refers to benzyloxycarbonyl, an amine protecting group; BOC refers to tert-butoxycarbonyl, an amine protecting group; HOAc refers to acetic acid; $NaCNBH_3$ refers to sodium cyanoborohydride; r.t. refers to room temperature; O/N refers to overnight; THE refers to tetrahydrofuran; $Boc_2O$ refers to di-tert-butyldicarbonate; TFA refers to trifluoroacetic acid; DIPEA refers to diisopropylethylamine; $SOCl_2$ refers to sulfoxide chloride; $CS_2$ refers to carbon disulfide; TsOH refers to p-toluenesulfonic acid; NFSI refers to N-fluorobenzenesulfonimide; NCS stands refers to 1-chloropyrrolidine-2,5-dione; n-$Bu_4NF$ refers to tetrabutylammonium fluoride; iPrOH refers to 2-propanol; mp refers to melting point; LDA refers to lithium diisopropylamine.

The compounds of the present disclosure are named according to the conventional naming principles in the art or by ChemDraw® software, and the commercially available compounds use the supplier catalog names.

The present disclosure is described in detail by the embodiments below, but it does not mean that there are any adverse restrictions on the present disclosure. The present disclosure has been described in detail herein, wherein specific embodiments thereof are also disclosed, and it will be apparent to those skilled in the art that various variations and improvements can be made to specific embodiments of the present disclosure without departing from the spirit and scope of the present disclosure.

Embodiment 1

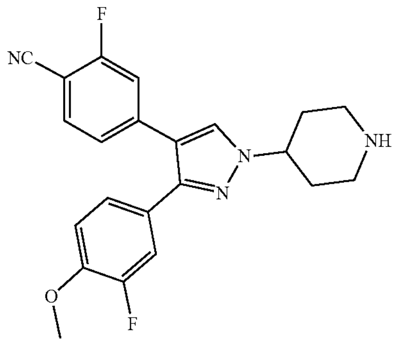

1

Synthetic Route:

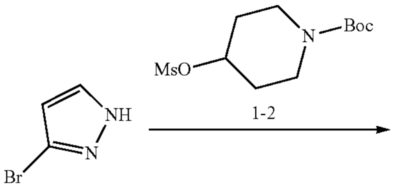

1-1

1-2

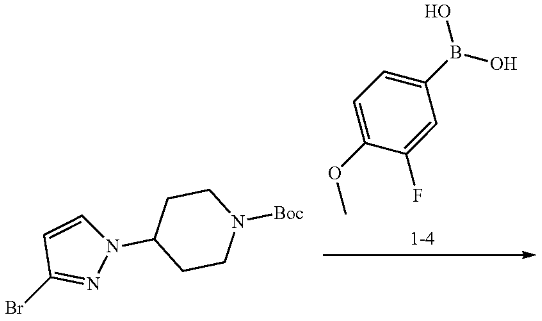

1-3

1-4

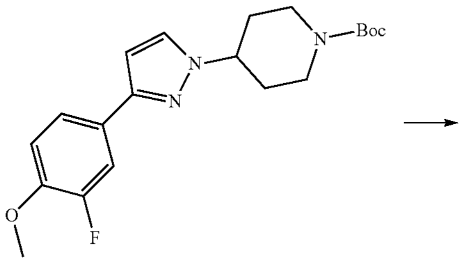

1-5

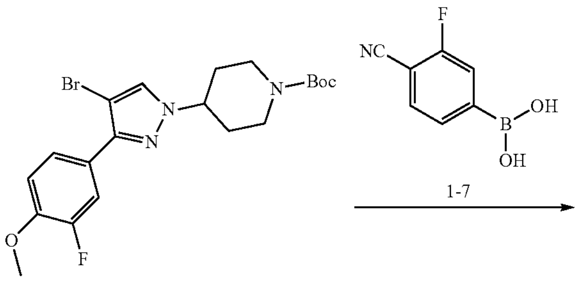

1-6

1-7

-continued

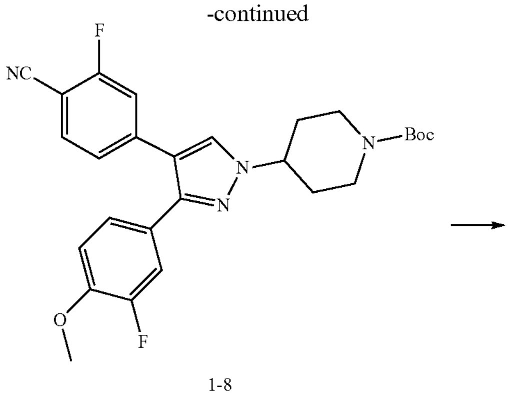

1-8

Hydrochloride of compound 1

Step 1

Under the protection of nitrogen, compound 1-1 (80.0 mg, 0.544 mmol) was dissolved in anhydrous N,N-dimethylformamide (5 mL), then compound 1-2 (152 mg, 0.544 mmol) and cesium carbonate (532 mg, 1.63 mmol) were added, and the reaction solution was stirred at 100° C. for 12 hours. Water (20 mL) was added to the reaction solution, and then the mixture was extracted with ethyl acetate (20 mL×1), dried over anhydrous sodium sulfate, filtered, concentrated under reduced pressure, and the residue was separated and purified by thin layer chromatography (1:1 petroleum ether/ethyl acetate, Rf=0.4) to obtain compound 1-3. $^{1}$H NMR (400 MHz, $CDCl_3$) δ 7.25 (d, J=2.4 Hz, 1H), 6.19 (d, J=2.4 Hz, 1H), 4.18-4.07 (m, 3H), 2.81-2.78 (m, 2H), 2.04-2.00 (m, 2H), 1.87-1.77 (m, 2H), 1.39 (s, 9H). MS-ESI calculated $[M-56+H]^+$274, found 274.

Step 2

Under the protection of nitrogen, compound 1-3 (74.0 mg, 0.224 mmol) and 1-4 (41.9 mg, 0.247 mmol) were dissolved in 1,4-dioxane (8 mL) and water (2 mL), then potassium phosphate (143 mg, 0.672 mmol) was added, followed by dichloro[1,1'-bis(di-tert-butylphosphino)ferrocene]palladium(II) (14.6 mg, 0.022 mmol), and the reaction solution was stirred at 100° C. for 12 hours. Water (30 mL) was added to the reaction solution, and then the mixture was extracted with ethyl acetate (30 mL×1), washed with saturated brine (30 mL×1), dried over anhydrous sodium sulfate, filtered, concentrated under reduced pressure, and the residue was separated and purified by thin layer chromatography to obtain compound 1-5. MS-ESI calculated $[M-56+H]^+$320, found 320.

Step 3

Under the protection of nitrogen, compound 1-5 (70.0 mg, 0.186 mmol) was dissolved in anhydrous N,N-dimethylformamide (5 mL), then N-bromosuccinimide (32.5 mg, 0.183 mmol) dissolved in anhydrous N,N-dimethylformamide (1 mL) was added dropwise within 30 minutes, and the reaction solution was stirred at 25° C. for 3 hours. Water (20 mL) was added to the reaction solution, and then the mixture was extracted with ethyl acetate (20 mL×1). The organic phase was washed with saturated brine (20 mL×1), dried over anhydrous sodium sulfate, filtered, concentrated under reduced pressure, and the residue was separated and purified by thin layer chromatography to obtain compound 1-6. $^1$H NMR (400 MHz, $CDCl_3$) δ 7.60-7.56 (m, 2H), 7.42 (s, 1H), 6.95-6.91 (m, 1H), 4.24-4.10 (m, 3H), 3.85 (s, 3H), 2.88-2.75 (m, 2H), 2.12-2.03 (m, 2H), 1.89-1.79 (m, 2H), 1.41 (s, 9H). MS-ESI calculated [M−56+H]$^+$398, 400, found 398, 400.

Step 4

Under the protection of nitrogen, compound 1-6 (55.0 mg, 0.121 mmol) and 1-7 (24.0 mg, 0.145 mmol) were dissolved in 1,4-dioxane (4 mL) and water (1 mL), then potassium phosphate (77.1 mg, 0.363 mmol) was added, then dichloro [1,1'-bis(di-tert-butylphosphino)ferrocene]palladium(II) (7.89 mg, 0.012 mmol) was added, and the reaction solution was stirred at 100° C. for 12 hours. Water (30 mL) was added to the reaction solution, and then the mixture was extracted with ethyl acetate (30 mL×1), washed with saturated brine (30 mL×1), dried over anhydrous sodium sulfate, filtered, concentrated under reduced pressure, and the residue was separated and purified by thin layer chromatography to obtain compound 1-8. MS-ESI calculated [M−56+H]$^+$439, found 439.

Step 5

Compound 1-8 (28.0 mg, 0.040 mmol) was dissolved in ethyl acetate (5 mL), and a solution of hydrogen chloride in ethyl acetate (4 mol/L, 5 mL) was added dropwise at 25° C. The reaction solution was stirred at 25° C. for 12 hours, concentrated under reduced pressure, and the crude product was purified by preparative high performance liquid chromatography (acidic, hydrochloric acid system) to obtain hydrochloride of compound 1. $^1$H NMR (400 MHz, $CD_3OD$) δ 8.10 (s, 1H), 7.69-7.65 (m, 1H), 7.27-7.23 (m, 2H), 7.21-7.18 (m, 1H), 7.12-7.08 (m, 2H), 4.66-4.58 (m, 1H), 3.90 (s, 3H), 3.62-3.59 (m, 2H), 3.29-3.22 (m, 2H), 2.43-2.30 (m, 4H). MS-ESI calculated [M+H]$^+$395, found 395.

Embodiment 2

2

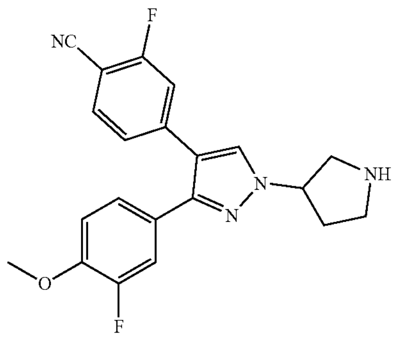

Synthetic Route:

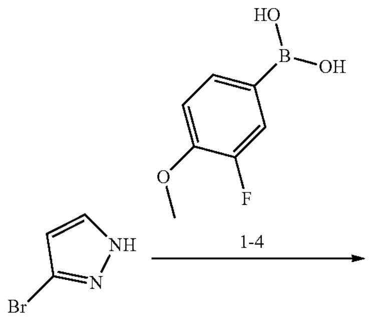

1-1

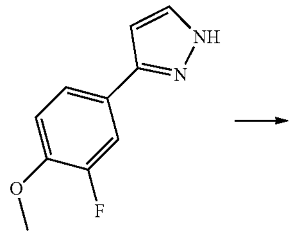

2-1

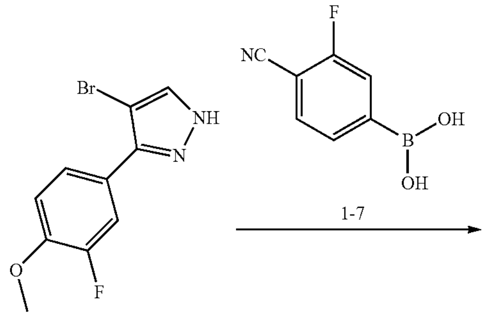

2-2

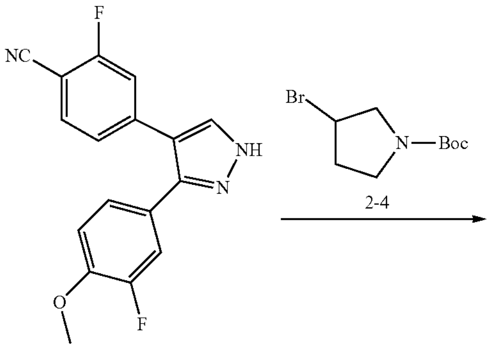

2-3

-continued

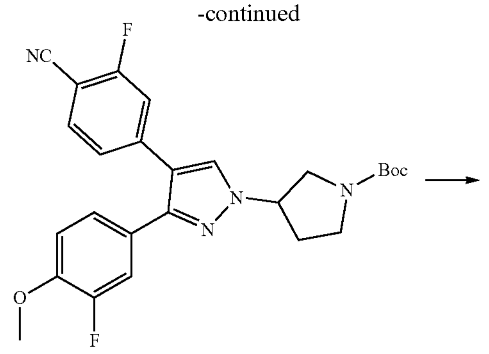

2-5

Hydrochloride of compound 2

Step 1

Under the protection of nitrogen, compound 1-1 (5.00 g, 34.0 mmol) was dissolved in 1,4-dioxane (50 mL) and water (5 mL), then 1-4 (6.36 g, 37.4 mmol), potassium phosphate (14.4 g, 68.0 mmol) and dichloro[1,1′ bis(di-tert-butylphosphino)ferrocene]palladium(II) (2.49 g, 3.40 mmol) were added, and the reaction solution was stirred at 90° C. for 12 hours. Water (100 mL) was added to the reaction solution, and then the mixture was extracted with ethyl acetate (200 mL×2). The organic phase was washed with saturated brine (200 mL×1), dried over anhydrous sodium sulfate, filtered, and concentrated under reduced pressure. The residue was separated and purified by silica gel column chromatography to obtain compound 2-1. $^1$H NMR (400 MHz, $CDCl_3$) δ 7.61 (d, J=2.4 Hz, 1H), 7.54-7.43 (m, 2H), 7.02-6.94 (m, 1H), 6.55 (d, J=2.4 Hz, 1H), 3.93 (s, 3H). MS-ESI calculated $[M+H]^+$193, found 193.

Step 2

Compound 2-1 (4.80 g, 25.0 mmol) and N-bromosuccinimide (4.45 g, 25.0 mmol) were dissolved in N,N-dimethylformamide (50 mL). The reaction mixture was stirred at 25° C. for 1 hour under the protection of nitrogen. Water (100 mL) was added to the reaction solution, and then the mixture was extracted with ethyl acetate (200 mL×2). The organic phase was washed with saturated brine (200 mL×3), dried over anhydrous sodium sulfate, filtered, and concentrated under reduced pressure. The residue was separated and purified by silica gel column chromatography to obtain compound 2-2. $^1$H NMR (400 MHz, $CDCl_3$) δ 7.59 (s, 1H), 7.55-7.44 (m, 2H), 7.00-6.95 (m, 1H), 3.93 (m, 3H). MS-ESI calculated $[M+H]^+$271 and 273, found 271 and 273.

Step 3

Under the protection of nitrogen, compound 2-2 (6.20 g, 22.9 mmol) was dissolved in 1,4-dioxane (50 mL) and water (10 mL), then 1-7 (3.77 g, 22.9 mmol), potassium phosphate (9.71 g, 45.7 mmol) and dichloro[1,1′ bis(di-tert-butylphosphino)ferrocene]palladium(II) (1.49 g, 2.29 mmol) were added, and the reaction solution was stirred at 100° C. for 12 hours. Water (100 mL) was added to the reaction solution, and then the mixture was extracted with ethyl acetate (200 mL×2). The organic phase was washed with saturated brine (200 mL×1), dried over anhydrous sodium sulfate, filtered, and concentrated under reduced pressure. The residue was separated and purified by silica gel column chromatography to obtain compound 2-3. $^1$H NMR (400 MHz, $CDCl_3$) δ 7.77 (s, 1H), 7.57-7.53 (m, 1H), 7.21-7.10 (m, 4H), 7.00-6.96 (m, 1H), 3.94 (s, 3H). MS-ESI calculated $[M+H]^+$312, found 312.

Step 4

Under the protection of nitrogen, compound 2-3 (500 mg, 1.61 mmol) was dissolved in N,N-dimethylformamide (10 mL), 2-4 (402 mg, 1.61 mmol) and cesium carbonate (1.57 g, 4.82 mmol) were added, and the reaction solution was stirred at 100° C. for 12 hours. Water (20 mL) was added to the reaction solution, and then the mixture was extracted with ethyl acetate (20 mL×2). The organic phase was washed with saturated brine (20 mL×3), dried over anhydrous sodium sulfate, filtered, and concentrated under reduced pressure. The residue was separated and purified by silica gel column chromatography to obtain compound 2-5. $^1$H NMR (400 MHz, $CDCl_3$) δ 7.59 (s, 1H), 7.55-7.52 (m, 1H), 7.24-7.21 (m, 1H), 7.15-7.09 (m, 3H), 6.93 (t, J=8.4 Hz, 1H), 5.94-4.86 (m, 1H), 3.96-3.77 (m, 5H), 3.74-3.42 (m, 2H), 2.56-2.37 (m, 2H), 1.48 (s, 9H). MS-ESI calculated $[M-56+H]^+$425, found 425.

Step 5

Compound 2-5 (150 mg, 0.312 mmol) was dissolved in ethyl acetate (2 mL), and a solution of hydrogen chloride in ethyl acetate (4 mol/L, 2 mL, 8.00 mmol) was added. The reaction solution was stirred at 20° C. for 4 hours. The reaction solution was concentrated under reduced pressure, and the residue was purified by preparative high performance liquid chromatography (acidic, hydrochloric acid system) to obtain hydrochloride of compound 2. $^1$H NMR (400 MHz, $CD_3OD$) δ 8.14 (s, 1H), 7.67 (t, J=7.6 Hz, 1H), 7.32-7.24 (m, 3H), 7.16-7.06 (m, 2H), 5.36-5.31 (m, 1H), 3.89 (s, 3H), 3.86-3.69 (m, 3H), 3.61-3.54 (m, 1H), 2.67-2.47 (m, 2H). MS-ESI calculated $[M+H]^+$381, found 381.

Embodiment 3

3

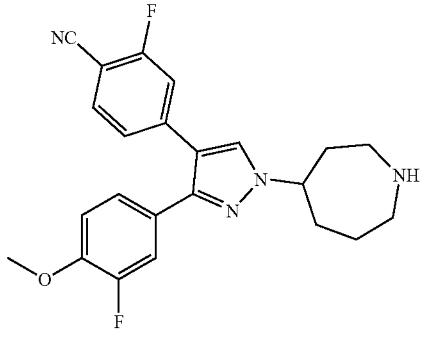

Synthetic Route:

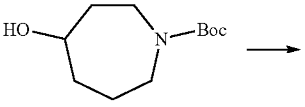

3-1

-continued

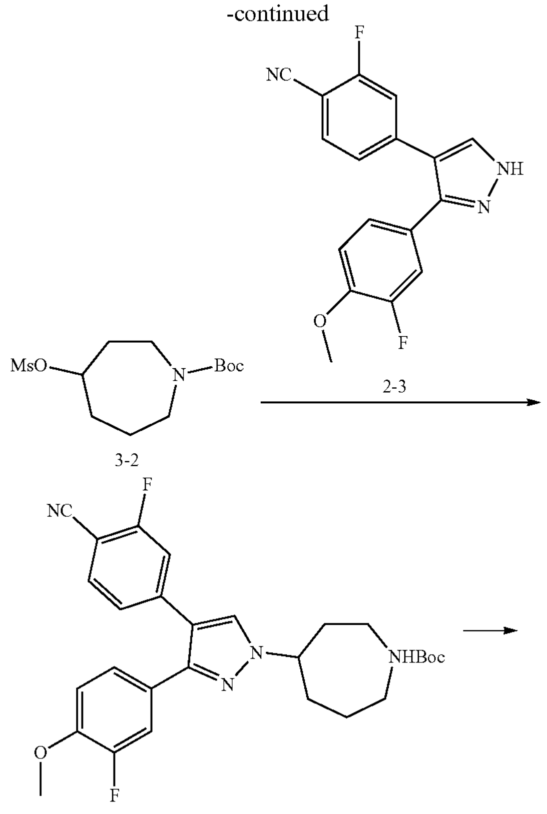

2-3

3-2

3-3

Hydrochloride of compound 3

Step 1

Under the protection of nitrogen, compound 3-1 (500 mg, 2.32 mmol) was dissolved in dichloromethane (5 mL), then triethylamine (470 mg, 4.64 mmol) and methanesulfonyl chloride (399 mg, 3.48 mmol) were added, and the reaction solution was stirred at 25° C. for 12 hours. Water (20 mL) was added to the reaction solution, and then the mixture was extracted with dichloromethane (20 mL×2). The organic phase was washed with saturated brine (20 mL×1), dried over anhydrous sodium sulfate, filtered, and concentrated under reduced pressure. The residue was separated and purified by silica gel column chromatography to obtain compound 3-2. $^1$H NMR (400 MHz, $CDCl_3$) δ 4.93-4.90 (m, 1H), 3.51-3.36 (m, 4H), 3.02 (s, 3H), 2.07-1.88 (m, 5H), 1.74-1.69 (m, 1H), 1.47 (s, 9H).

Step 2

Under the protection of nitrogen, compound 2-3 (360 mg, 1.16 mmol) was dissolved in N,N-dimethylformamide (10 mL), then compound 3-2 (407 mg, 1.61 mmol) and cesium carbonate (1.13 g, 3.47 mmol) were added, and the reaction solution was stirred at 100° C. for 12 hours. Water (20 mL) was added to the reaction solution, and then the mixture was extracted with ethyl acetate (20 mL×2). The organic phase was washed with saturated brine (20 mL×3), dried over anhydrous sodium sulfate, filtered, and concentrated under reduced pressure. The residue was separated and purified by silica gel column chromatography to obtain compound 3-3. $^1$H NMR (400 MHz, $CDCl_3$) δ 7.58 (s, 1H), 7.52 (t, J=7.2 Hz, 1H), 7.23-7.20 (m, 1H), 7.16-7.07 (m, 3H), 6.93 (t, J=8.4 Hz, 1H), 4.92-4.88 (m, 1H), 3.91 (s, 3H), 3.46-3.29 (m, 5H), 1.98-1.64 (m, 5H), 1.48 (s, 9H). MS-ESI calculated $[M-56+H]^+$453, found 453.

Step 3

Compound 3-3 (200 mg, 0.393 mmol) was dissolved in ethyl acetate (2 mL), and a solution of hydrogen chloride in ethyl acetate (4 mol/L, 2 mL) was added. The reaction solution was stirred at 25° C. for 3 hours. The reaction solution was concentrated under reduced pressure, and the residue was purified by preparative high performance liquid chromatography (acidic, hydrochloric acid system) to obtain hydrochloride of compound 3. $^1$H NMR (400 MHz, $CD_3OD$) δ 8.13 (s, 1H), 7.64 (t, J=7.2 Hz, 1H), 7.24 (d, J=9.2 Hz, 2H), 7.20-7.15 (m, 1H), 7.14-7.07 (m, 2H), 4.74-4.65 (m, 1H), 3.90 (s, 3H), 3.62-3.52 (m, 1H), 3.44-3.32 (m, 3H), 2.59-2.44 (m, 2H), 2.42-2.25 (m, 2H), 2.18-2.16 (m, 1H), 2.08-1.94 (m, 1H). MS-ESI calculated $[M+H]^+$409, found 409.

Embodiment 4

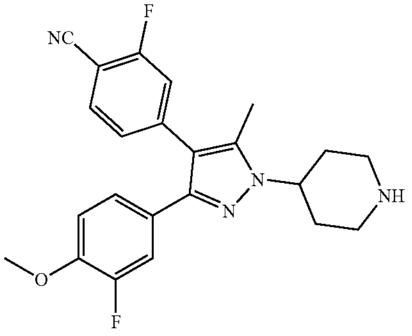

4

Synthetic Route:

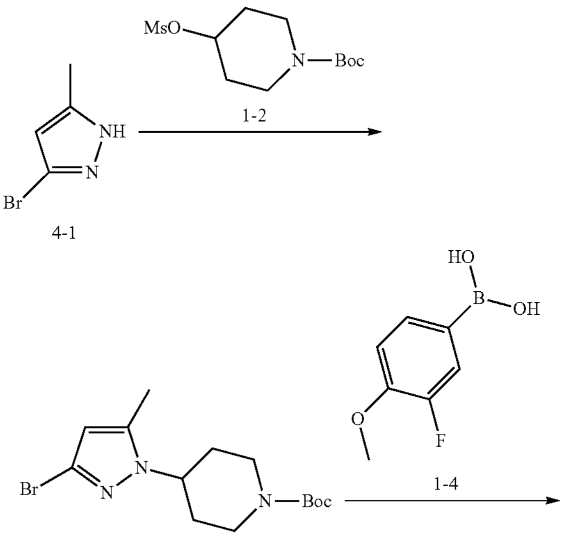

1-2

4-1

1-4

4-2

-continued

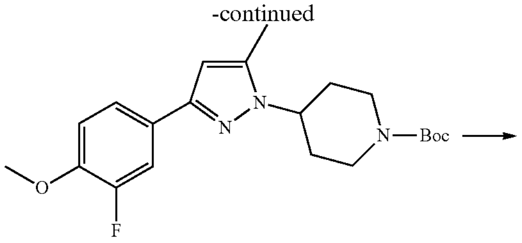

4-3

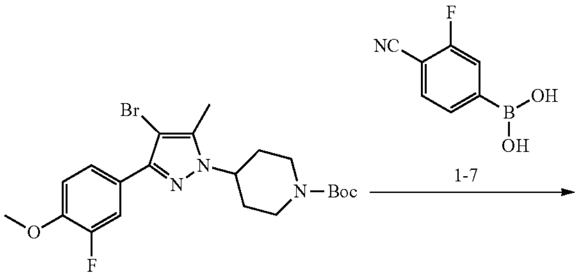

4-4

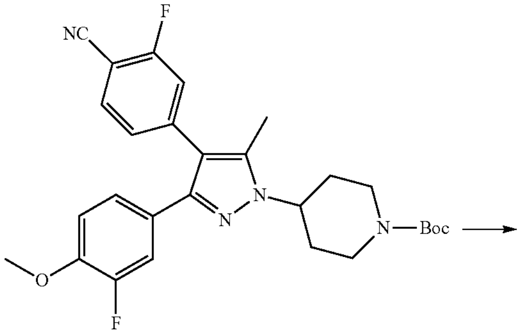

4-5

Hydrochloride of compound 4

Step 1

Under the protection of nitrogen, compound 4-1 (2.00 g, 12.4 mmol) was dissolved in N,N-dimethylformamide (20 mL), then compound 1-2 (3.47 g, 12.4 mmol) and cesium carbonate (12.1 g, 37.3 mmol) were added, and the reaction solution was stirred at 100° C. for 12 hours. Water (20 mL) was added to the reaction solution, and then the mixture was extracted with ethyl acetate (40 mL×2). The organic phase was washed with saturated brine (40 mL×3), dried over anhydrous sodium sulfate, filtered, and concentrated under reduced pressure. The residue was separated and purified by silica gel column chromatography to obtain compound 4-2. $^1$H NMR (400 MHz, $CDCl_3$) δ 5.99 (s, 1H), 4.34-4.26 (m, 2H), 4.09-4.01 (m, 1H), 2.83-2.79 (m, 2H), 2.26 (s, 3H), 2.13-1.07 (m, 2H), 1.84-1.78 (m, 2H), 1.45 (s, 9H). MS-ESI calculated [M−56+H]$^+$288 and 290, found 288 and 290.

Step 2

Under the protection of nitrogen, compound 4-2 (2.50 g, 7.26 mmol) was dissolved in 1,4-dioxane (20 mL) and water (4 mL), then compound 1-4 (1.48 g, 8.71 mmol), potassium phosphate (3.08 g, 14.5 mmol) and dichloro[1,1′-bis(di-tert-butylphosphino)ferrocene]palladium(II) (531 mg, 0.726 mmol) were added, and the reaction solution was stirred at 90° C. for 12 hours. Water (20 mL) was added to the reaction solution, and then the mixture was extracted with ethyl acetate (20 mL×2). The organic phase was washed with saturated brine (20 mL×1), dried over anhydrous sodium sulfate, filtered, and concentrated under reduced pressure. The residue was separated and purified by silica gel column chromatography to obtain compound 4-3. $^1$H NMR (400 MHz, $CDCl_3$) δ 7.53-7.45 (m, 2H), 6.96 (t, J=8.4 Hz, 1H), 6.23 (s, 1H), 4.32-4.27 (m, 2H), 4.16-4.08 (m, 1H), 3.91 (s, 3H), 2.93-2.88 (m, 2H), 2.33 (s, 3H), 2.26-2.16 (m, 2H), 1.92-1.87 (m, 2H), 1.50 (s, 9H). MS-ESI calculated [M+H]$^+$ 390, found 390.

Step 3

Compound 4-3 (1.50 g, 3.85 mmol) and N-bromosuccinimide (685 mg, 3.85 mmol) were dissolved in N,N-dimethylformamide (20 mL). The reaction solution was stirred at 25° C. for 1 hour under the protection of nitrogen. Water (50 mL) was added to the reaction solution, and then the mixture was extracted with ethyl acetate (50 mL×2). The organic phase was washed with saturated brine (50 mL×3), dried over anhydrous sodium sulfate, filtered, and concentrated under reduced pressure. The residue was separated and purified by silica gel column chromatography to obtain compound 4-4. $^1$H NMR (400 MHz, $CDCl_3$) δ 7.68-7.61 (m, 2H), 7.03-6.97 (m, 1H), 4.33-4.26 (m, 2H), 4.20-4.12 (m, 1H), 3.91 (s, 3H), 3.01-2.85 (m, 2H), 2.34 (s, 3H), 2.23-2.14 (m, 2H), 1.92-1.87 (m, 2H), 1.48 (s, 9H). MS-ESI calculated [M−56+H]$^+$412 and 414, found 412 and 414.

Step 4

Under the protection of nitrogen, compound 4-4 (500 mg, 1.07 mmol) was dissolved in 1,4-dioxane (5 mL) and water (1 mL), then compound 1-7 (211 mg, 1.28 mmol), potassium phosphate (453 mg, 2.14 mmol) and dichloro[1,1′-bis(di-tert-butylphosphino)ferrocene]palladium(II) (69.6 mg, 0.107 mmol) were added, and the reaction solution was stirred at 100° C. for 12 hours. Water (10 mL) was added to the reaction solution, and then the mixture was extracted with ethyl acetate (20 mL×2). The organic phase was washed with saturated brine (20 mL×1), dried over anhydrous sodium sulfate, filtered, and concentrated under reduced pressure. The residue was separated and purified by silica gel column chromatography to obtain compound 4-5. $^1$H NMR (400 MHz, $CDCl_3$) δ 7.58 (t, J=7.6 Hz, 1H), 7.17-7.13 (m, 1H), 7.09-7.01 (m, 2H), 6.98 (d, J=8.4 Hz, 1H), 6.89-6.83 (m, 1H), 4.40-4.17 (m, 3H), 3.88 (s, 3H), 2.93-2.89 (m, 2H), 2.33-2.20 (m, 5H), 1.96-1.89 (m, 2H), 1.49 (s, 9H). MS-ESI calculated [M−56+H]$^+$453, found 453.

Step 5

Compound 4-5 (500 mg, 0.983 mmol) was dissolved in ethyl acetate (5 mL), and a solution of hydrogen chloride in ethyl acetate (4 mol/L, 5 mL) was added. The reaction solution was stirred at 25° C. for 3 hours. The reaction solution was concentrated under reduced pressure, and the residue was purified by preparative high performance liquid chromatography (acidic, hydrochloric acid system) to obtain hydrochloride of compound 4. $^1$H NMR (400 MHz, $CD_3OD$) δ 7.72 (t, J=7.6 Hz, 1H), 7.16-7.09 (m, 3H), 7.04-6.92 (m, 2H), 4.76-4.69 (m, 1H), 3.85 (m, 3H), 3.66-3.62 (m, 2H), 3.36-3.34 (m, 1H), 3.31-3.27 (m, 1H), 2.51-2.36 (m, 5H), 2.30-2.24 (m, 2H). MS-ESI calculated [M+H]$^+$409, found 409.

Embodiment 5

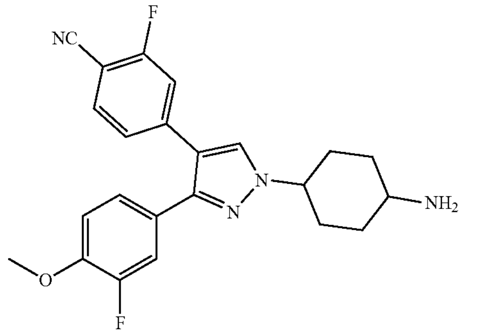

Synthetic Route:

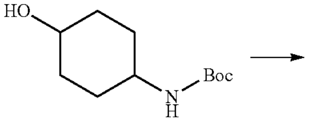

5-1

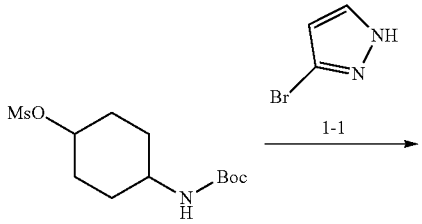

5-1

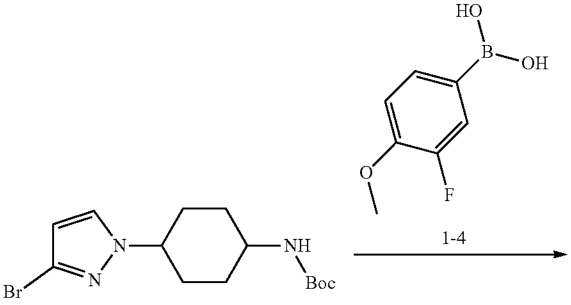

5-3

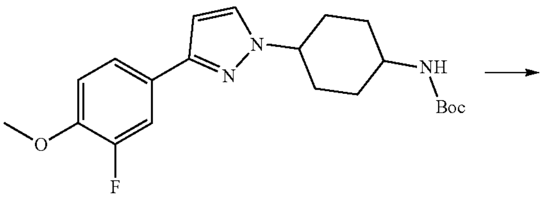

5-4

-continued

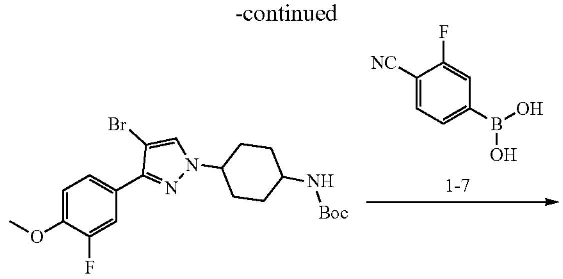

5-5

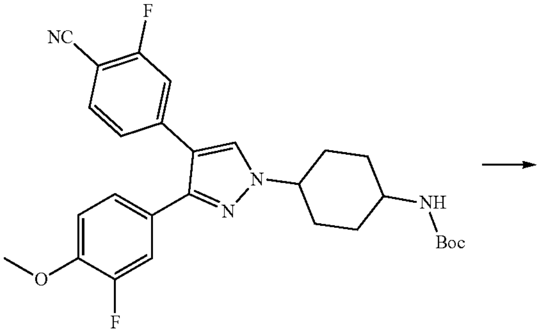

5-6

Hydrochloride of compound 5

Step 1

Under the protection of nitrogen, compound 5-1 (2.00 g, 9.29 mmol) was dissolved in dichloromethane (20 mL), then triethylamine (1.88 g, 18.6 mmol) and methanesulfonyl chloride (1.60 g, 13.9 mmol) were added, and the reaction solution was stirred at 25° C. for 12 hours. Water (20 mL) was added to the reaction solution, and then the mixture was extracted with dichloromethane (20 mL×2). The organic phase was washed with saturated brine (20 mL×1), dried over anhydrous sodium sulfate, filtered, and concentrated under reduced pressure. The residue was separated and purified by silica gel column chromatography to obtain compound 5-2. $^1$H NMR (400 MHz, $CDCl_3$) δ 4.66-4.59 (m, 1H), 4.42-4.38 (m, 1H), 3.49-3.45 (m, 1H), 3.01 (s, 3H), 2.16-2.06 (m, 4H), 1.70-1.64 (m, 2H), 1.44 (s, 9H), 1.31-1.21 (m, 2H).

Step 2

Under the protection of nitrogen, compound 5-2 (2.40 g, 8.16 mmol) was dissolved in N,N-dimethylformamide (20 mL), then compound 1-1 (1.00 g, 6.80 mmol) and cesium carbonate (6.65 g, 20.4 mmol) were added, and the reaction solution was stirred at 100° C. for 12 hours. Water (20 mL) was added to the reaction solution, and then the mixture was extracted with ethyl acetate (20 mL×2). The organic phase was washed with saturated brine (20 mL×3), dried over anhydrous sodium sulfate, filtered, and concentrated under reduced pressure. The residue was separated and purified by silica gel column chromatography to obtain compound 5-3. $^1$H NMR (400 MHz, $CDCl_3$) δ 7.33 (d, J=2.4 Hz, 1H), 6.24 (d, J=2.4 Hz, 1H), 4.84-4.81 (m, 1H), 4.12-4.05 (m, 1H), 3.83-3.80 (m, 1H), 2.12-1.91 (m, 4H), 1.90-1.83 (m, 2H), 1.74-1.65 (m, 2H), 1.44 (s, 9H). MS-ESI calculated $[M-56+H]^+$ 288 and 290, found 288 and 290.

Step 3

Under the protection of nitrogen, compound 5-3 (600 mg, 1.74 mmol) was dissolved in 1,4-dioxane (5 mL) and water (1 mL), then compound 1-4 (296 mg, 1.74 mmol), potassium phosphate (740 mg, 3.49 mmol) and [1,1'-bis(diphenylphosphino)ferrocene]dichloropalladium(II) (128 mg, 0.174 mmol) were added, and the reaction solution was stirred at 90° C. for 12 hours. Water (20 mL) was added to the reaction solution, and then the mixture was extracted with ethyl acetate (20 mL×2). The organic phase was washed with saturated brine (20 mL×1), dried over anhydrous sodium sulfate, filtered, and concentrated under reduced pressure. The residue was separated and purified by silica gel column chromatography to obtain compound 5-4. $^1$H NMR (400 MHz, $CDCl_3$) δ 7.60-7.38 (m, 3H), 6.98 (t, J=8.4 Hz, 1H), 6.46 (d, J=2.4 Hz, 1H), 4.78-4.74 (m, 1H), 4.22-4.15 (m, 1H), 3.92 (s, 3H), 3.85-3.82 (m, 1H), 2.12-2.05 (m, 4H), 1.91-1.84 (m, 2H), 1.79-1.69 (m, 2H), 1.47 (s, 9H). MS-ESI calculated $[M+H]^+$390, found 390.

Step 4

Compound 5-4 (320 mg, 0.822 mmol) and N-bromosuccinimide (146 mg, 0.822 mmol) were dissolved in N,N-dimethylformamide (5 mL). The reaction solution was stirred at 25° C. for 1 hour under the protection of nitrogen. Water (30 mL) was added to the reaction solution, and then the mixture was extracted with ethyl acetate (30 mL×2). The organic phase was washed with saturated brine (30 mL×3), dried over anhydrous sodium sulfate, filtered, and concentrated under reduced pressure. The residue was separated and purified by silica gel column chromatography to obtain compound 5-5. $^1$H NMR (400 MHz, $CDCl_3$) δ 7.68-7.63 (m, 2H), 7.52 (s, 1H), 7.01 (t, J=8.8 Hz, 1H), 4.76-4.71 (m, 1H), 4.19-4.11 (m, 1H), 3.93 (s, 3H), 3.84-3.80 (m, 1H), 2.05-2.00 (m, 4H), 1.89-1.85 (m, 2H), 1.78-1.73 (m, 2H), 1.46 (s, 9H). MS-ESI calculated $[M-56+H]^+$412 and 414, found 412 and 414.

Step 5

Under the protection of nitrogen, compound 5-5 (350 mg, 0.747 mmol) was dissolved in 1,4-dioxane (5 mL) and water (1 mL), then compound 1-7 (148 mg, 0.897 mmol), potassium phosphate (317 mg, 1.49 mmol) and dichloro[1,1'-bis(di-tert-butylphosphino)ferrocene]palladium(II) (48.7 mg, 0.0747 mmol) were added, and the reaction solution was stirred at 100° C. for 12 hours. Water (10 mL) was added to the reaction solution, and then the mixture was extracted with ethyl acetate (20 mL×2). The organic phase was washed with saturated brine (20 mL×1), dried over anhydrous sodium sulfate, filtered, and concentrated under reduced pressure. The residue was separated and purified by silica gel column chromatography to obtain compound 5-6. $^1$H NMR (400 MHz, $CDCl_3$) δ 7.64 (s, 1H), 7.54-7.51 (m, 1H), 7.25-7.22 (m, 1H), 7.15-7.10 (m, 3H), 6.94 (t, J=8.4 Hz, 1H), 4.77-4.74 (m, 1H), 4.25-4.19 (m, 1H), 3.92 (s, 3H), 3.87-3.84 (m, 1H), 2.18-2.07 (m, 4H), 1.95-1.91 (m, 2H), 1.82-1.74 (m, 2H), 1.46 (s, 9H). MS-ESI calculated $[M-56+H]^+$453, found 453.

Step 6

Compound 5-6 (350 mg, 0.688 mmol) was dissolved in ethyl acetate (5 mL), and a solution of hydrogen chloride in ethyl acetate (4 mol/L, 5 mL) was added. The reaction solution was stirred at 25° C. for 3 hours. The reaction solution was concentrated under reduced pressure, and the residue was purified by preparative high performance liquid chromatography (acidic, hydrochloric acid system) to obtain hydrochloride of compound 5. $^1$H NMR (400 MHz, $CD_3OD$) δ 8.17 (s, 1H), 7.65 (t, J=7.6 Hz, 1H), 7.27-7.15 (m, 3H), 7.13-7.06 (m, 2H), 4.52-4.41 (m, 1H), 3.90 (s, 3H), 3.49-3.40 (m, 1H), 2.45-2.41 (m, 2H), 2.16-2.08 (m, 2H), 2.05-1.89 (m, 4H). MS-ESI calculated $[M+H]^+$409, found 409.

Embodiment 6

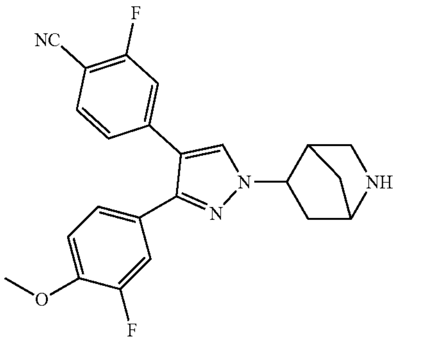

6

Synthetic Route:

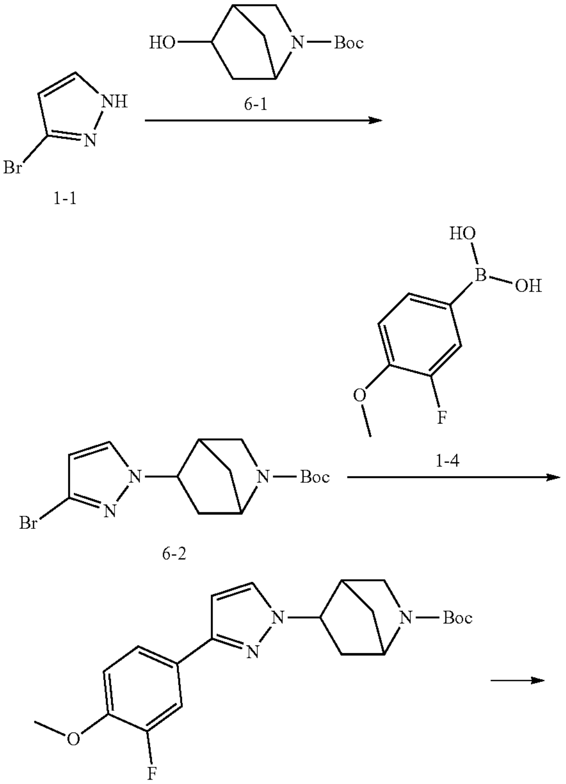

1-1

6-1

6-2

1-4

6-3

-continued

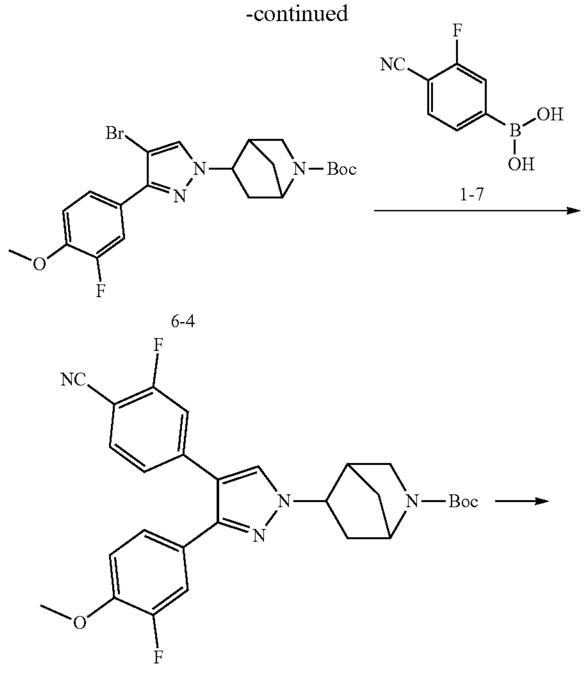

1-7

6-4

6-5

Hydrochloride of compound 6

Step 1

Under the protection of nitrogen, compound 1-1 (500 mg, 3.40 mmol) was dissolved in tetrahydrofuran (10 mL), then compound 6-1 (726 mg, 3.40 mmol), triphenylphosphine (1.78 g, 6.80 mmol) and diisopropyl azodicarboxylate (1.03 g, 5.10 mmol) were added, and the reaction solution was stirred at 70° C. for 12 hours. Water (30 mL) was added to the reaction solution, and then the mixture was extracted with ethyl acetate (30 mL×2). The organic phase was washed with saturated brine (30 mL×1), dried over anhydrous sodium sulfate, filtered, and concentrated under reduced pressure. The residue was separated and purified by silica gel column chromatography to obtain compound 6-2. $^{1}$H NMR (400 MHz, $CDCl_3$) δ 7.36-7.29 (m, 1H), 6.29 (d, J=2.4 Hz, 1H), 4.85-4.73 (m, 1H), 4.38-4.20 (m, 1H), 3.19-3.05 (m, 1H), 3.04-2.78 (m, 2H), 2.34-2.09 (m, 2H), 1.87-1.84 (m, 1H), 1.72-1.69 (m, 1H), 1.27 (s, 9H). MS-ESI calculated $[M-56+H]^+$286 and 288, found 286 and 288.

Step 2

Under the protection of nitrogen, compound 6-2 (650 mg, 1.90 mmol) was dissolved in 1,4-dioxane (5 mL) and water (1 mL), then compound 1-4 (323 mg, 1.90 mmol), potassium phosphate (806 mg, 3.80 mmol) and [1,1′-bis(diphenylphosphino)ferrocene]dichloropalladium(II) (139 mg, 0.190 mmol) were added, and the reaction solution was stirred at 90° C. for 12 hours. Water (20 mL) was added to the reaction solution, and then the mixture was extracted with ethyl acetate (20 mL×2). The organic phase was washed with saturated brine (20 mL×1), dried over anhydrous sodium sulfate, filtered, and concentrated under reduced pressure. The residue was separated and purified by silica gel column chromatography to obtain compound 6-3. $^{1}$H NMR (400 MHz, $CDCl_3$) δ 7.62-7.38 (m, 3H), 6.99-6.94 (m, 1H), 6.53-6.48 (m, 1H), 4.92-4.85 (m, 1H), 4.38-4.26 (m, 1H), 3.92 (s, 3H), 3.21-2.97 (m, 3H), 2.42-2.19 (m, 2H), 1.88-1.82 (m, 1H), 1.75-1.70 (m, 1H), 1.46 (s, 9H). MS-ESI calculated $[M+H]^+$388, found 388.

Step 3

Compound 6-3 (500 mg, 1.29 mmol) and N-bromosuccinimide (230 mg, 1.29 mmol) were dissolved in N,N-dimethylformamide (5 mL). The reaction solution was stirred at 25° C. for 1 hour under the protection of nitrogen. Water (30 mL) was added to the reaction solution, and then the mixture was extracted with ethyl acetate (30 mL×2). The organic phase was washed with saturated brine (30 mL×3), dried over anhydrous sodium sulfate, filtered, and concentrated under reduced pressure. The residue was separated and purified by silica gel column chromatography to obtain compound 6-4. $^{1}$H NMR (400 MHz, $CDCl_3$) δ 7.72-7.67 (m, 2H), 7.50-7.46 (m, 1H), 7.02-6.97 (m, 1H), 4.90-4.75 (m, 1H), 4.36-4.25 (m, 1H), 3.92 (s, 3H), 3.20-3.08 (m, 2H), 3.00-2.95 (m, 1H), 2.41-2.35 (m, 1H), 2.26-2.20 (m, 1H), 1.90-1.87 (m, 1H), 1.76-1.72 (m, 1H), 1.46 (m, 9H). MS-ESI calculated $[M-56+H]^+$410 and 412, found 410 and 412.

Step 4

Under the protection of nitrogen, compound 6-4 (600 mg, 1.29 mmol) was dissolved in 1,4-dioxane (10 mL) and water (2 mL), then compound 1-7 (255 mg, 1.54 mmol), potassium phosphate (546 mg, 2.57 mmol) and dichloro[1,1′-bis(di-tert-butylphosphino)ferrocene]palladium(II) (83.9 mg, 0.129 mmol) were added, and the reaction solution was stirred at 100° C. for 12 hours. Water (10 mL) was added to the reaction solution, and then the mixture was extracted with ethyl acetate (20 mL×2). The organic phase was washed with saturated brine (20 mL×1), dried over anhydrous sodium sulfate, filtered, and concentrated under reduced pressure. The residue was separated and purified by silica gel column chromatography for 6-5. $^{1}$H NMR (400 MHz, $CDCl_3$) δ 7.61-7.52 (m, 2H), 7.27-7.23 (m, 1H), 7.17-7.09 (m, 3H), 6.95-6.91 (m, 1H), 4.95-4.87 (m, 1H), 4.41-4.29 (m, 1H), 3.92 (s, 3H), 3.23-3.01 (m, 3H), 2.42-2.27 (m, 2H), 1.97-1.92 (m, 1H), 1.79-1.76 (m, 1H), 1.52 (s, 9H). MS-ESI calculated $[M+H]^+$507, found 507.

Step 5

Compound 6-5 (600 mg, 1.18 mmol) was dissolved in ethyl acetate (5 mL), and a solution of hydrogen chloride in ethyl acetate (4 mol/L, 5 mL) was added. The reaction solution was stirred at 25° C. for 2.5 hours. The reaction solution was concentrated under reduced pressure, and the residue was purified by preparative high performance liquid chromatography (acidic, hydrochloric acid system) to obtain hydrochloride of compound 6. $^{1}$H NMR (400 MHz, $CD_3OD$) δ 8.22 (s, 1H), 7.66 (t, J=7.6 Hz, 1H), 7.28-7.25 (m, 3H), 7.17-7.07 (m, 2H), 5.08-5.05 (m, 1H), 4.25-4.22 (m, 1H), 3.90 (s, 3H), 3.48-3.45 (m, 1H), 3.19-3.16 (m, 2H), 2.64-2.47 (m, 2H), 2.19-2.16 (m, 1H), 2.04-2.01 (m, 1H). MS-ESI calculated $[M+H]^+$ 407, found 407.

Embodiment 7

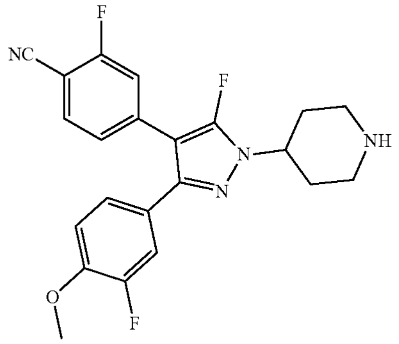

7

Synthetic Route:

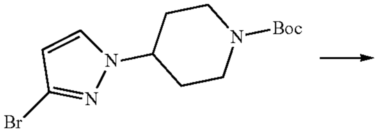

1-3

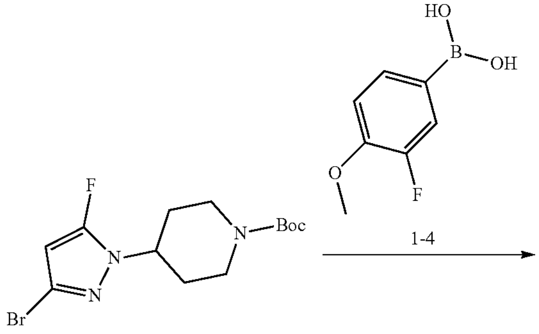

7-1

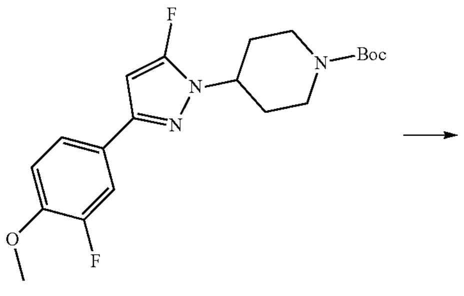

7-2

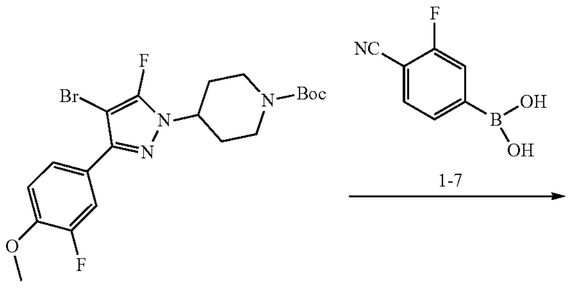

7-3

-continued

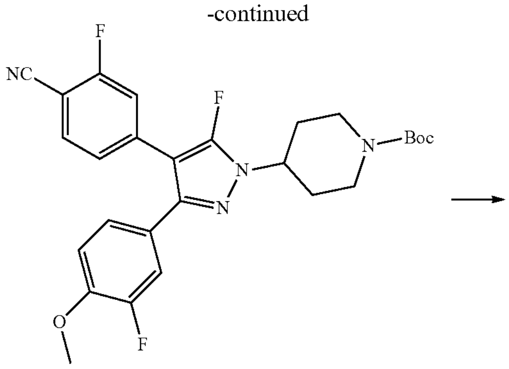

7-4

Hydrochloride of compound 7

Step 1

Under the protection of nitrogen, compound 1-3 (300 mg, 0.908 mmol) was dissolved in anhydrous tetrahydrofuran (10 mL), then lithium diisopropylamine (2.0 mol/L tetrahydrofuran solution, 681 μL, 1.36 mmol) was added dropwise at −78° C., and the reaction solution was stirred at −78° C. for 0.5 hours. N-fluorobenzenesulfonamide (573 mg, 1.82 mmol) was then added, and the reaction solution was stirred at 25° C. for 11.5 hours. Water (20 mL) was added to the reaction solution, and the mixture was extracted with ethyl acetate (20 mL×1). The organic phase was washed with saturated brine (30 mL×1), dried over anhydrous sodium sulfate, filtered, concentrated under reduced pressure, and the residue was separated and purified by silica gel column chromatography to obtain compound 7-1. MS-ESI calculated $[M-Boc+H]^+$248, found 248.

Step 2

Under the protection of nitrogen, compound 7-1 (175 mg, 0.503 mmol) and compound 1-4 (94.0 mg, 0.553 mmol) were dissolved in 1,4-dioxane (8 mL) and water (2 mL), then potassium phosphate (320 mg, 1.51 mmol) was added, followed by dichloro[1,1'-bis(di-tert-butylphosphino)ferrocene]palladium(II) (32.8 mg, 0.022 mmol), and the reaction solution was stirred at 100° C. for 12 hours. Water (30 mL) was added to the reaction solution, and then the mixture was extracted with ethyl acetate (30 mL×1). The organic phase was washed with saturated brine (30 mL×1), dried over anhydrous sodium sulfate, filtered, concentrated under reduced pressure, and the residue was separated and purified by silica gel column chromatography to obtain compound 7-2. MS-ESI calculated $[M-56+H]^+$338, found 338.

Step 3

Under the protection of nitrogen, compound 7-2 (130 mg, 0.330 mmol) was dissolved in anhydrous N,N-dimethylformamide (5 mL), then N-bromosuccinimide (70.6 mg, 0.397 mmol) was added, and the reaction solution was stirred at 25° C. for 2.5 hours. Water (20 mL) was added to the reaction solution, and then the mixture was extracted with ethyl acetate (20 mL×1). The organic phase was washed with saturated brine (20 mL×1), dried over anhydrous sodium sulfate, filtered, concentrated under reduced pressure, and the residue was separated and purified by silica gel column chromatography to obtain compound 7-3. MS-ESI calculated $[M-56+H]^+$416 and 418, found 416 and 418.

Step 4

Under the protection of nitrogen, compound 7-3 (10.0 mg, 0.021 mmol) and 1-7 (4.19 mg, 0.025 mmol) were dissolved in 1,4-dioxane (4 mL) and water (1 mL), then potassium phosphate (13.5 mg, 0.064 mmol) was added, followed by dichloro[1,1'-bis(di-tert-butylphosphino)ferrocene]palladium(II) (1.38 mg, 0.002 mmol), and the reaction solution was stirred at 100° C. for 12 hours. Water (30 mL) was added to the reaction solution, and then the mixture was extracted with ethyl acetate (30 mL×1). The organic phase was washed with saturated brine (30 mL×1), dried over anhydrous sodium sulfate, filtered, concentrated under reduced pressure, and the residue was separated and purified by silica gel column chromatography to obtain compound 7-4. MS-ESI calculated $[M-56+H]^+$457, found 457.

Step 5

Compound 7-4 (28 mg, 0.040 mmol) was dissolved in ethyl acetate (10 mL), and a solution of hydrogen chloride in ethyl acetate (4 mol/L, 10 mL) was added dropwise at 25° C. The reaction solution was stirred at 25° C. for 1 hour, concentrated under reduced pressure, and the crude product was purified by preparative high performance liquid chromatography (acidic, hydrochloric acid system) to obtain hydrochloride of compound 7. $^1H$ NMR (400 MHz, $CD_3OD$) δ 7.72 (t, J=7.6 Hz, 1H), 7.25-7.19 (m, 3H), 7.12-7.07 (m, 2H), 4.78-4.73 (m, 1H), 3.89 (s, 3H), 3.64-3.61 (m, 2H), 3.30-3.25 (m, 2H), 2.46-2.31 (m, 4H). MS-ESI calculated $[M+H]^+$413, found 413.

Embodiment 8

8

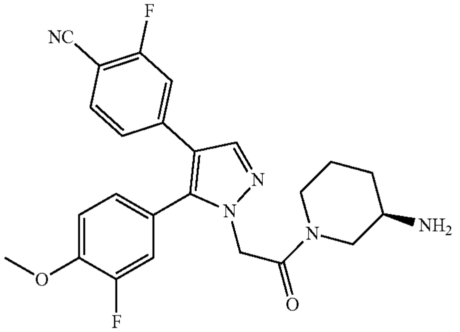

Synthetic Route:

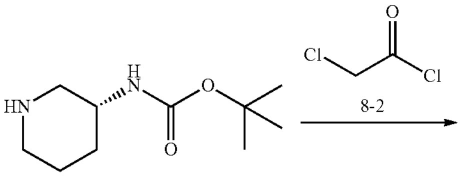

8-1

-continued

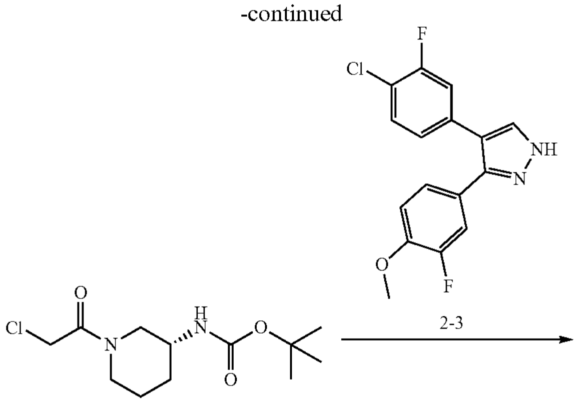

8-3

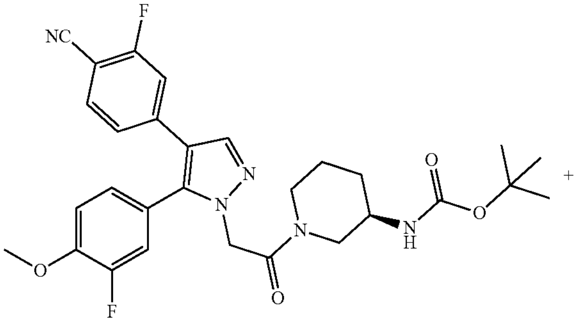

8-4

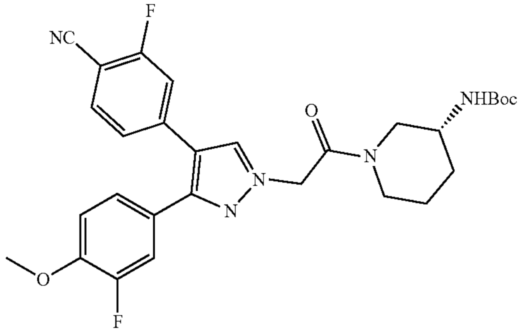

8-5

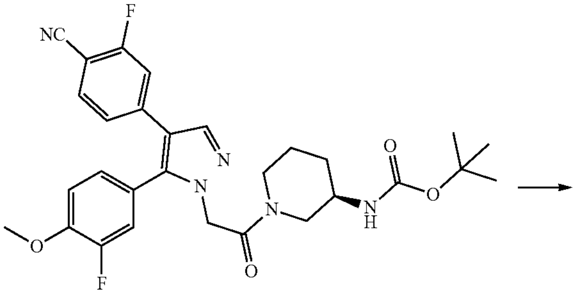

8-4

Hydrochloride of compound 8

Step 1

Compound 8-1 (2.00 g, 9.99 mmol) was dissolved in dichloromethane (100 mL), and triethylamine (1.52 g, 15.0 mmol) was added, and then compound 8-2 (1.69 g, 15.0 mmol) was added dropwise. The reaction solution was stirred at 0° C. for 1 hour. The organic phase was filtered, the filter cake was washed with dichloromethane (50 mL×3), and the filtrate was concentrated under reduced pressure. The residue was separated and purified by silica gel column chromatography to obtain compound 8-3. Compound 8-3 MS-ESI calculated $[M-56+H]^+$221, found 221.

Step 2

Under the protection of nitrogen, compound 2-3 (150 mg, 0.482 mmol) was dissolved in N,N-dimethylformamide (10 mL), then compound 8-3 (133 mg, 0.482 mmol) and cesium carbonate (471 mg, 1.45 mmol) were added, and the reaction solution was stirred at 100° C. for 12 hours. Water (50 mL) was added to the reaction solution, and the mixture was extracted with ethyl acetate (30 mL×2). The organic phase was washed with saturated brine (30 mL×1), dried over anhydrous sodium sulfate, filtered, concentrated under reduced pressure, and the residue was separated by preparative high performance liquid chromatography (acidic condition, column type: Venusil ASB Phenyl 150×30 mm×5 μm; mobile phase: [water (0.05% HCl)-acetonitrile]; B (acetonitrile) %: 60%-90%, 10 minutes) to obtain compound 8-4 (retention time: 4.69 minutes) and compound 8-5 (retention time: 4.60 minutes). $^1$H NMR (400 MHz, $CD_3OD$) δ 8.02-7.95 (m, 1H), 7.69-7.60 (m, 1H), 7.26-7.24 (m, 2H), 7.19-7.06 (m, 3H), 5.32-5.10 (m, 2H), 4.18-4.04 (m, 1H), 3.90 (s, 3H), 3.86-3.65 (m, 1H), 3.59-3.39 (m, 1H), 3.28-2.95 (m, 2H), 2.20-1.84 (m, 2H), 1.82-1.56 (m, 2H), 1.54-1.36 (m, 9H). MS-ESI calculated $[M-56+H]^+$496, found 496. Compound 8-5 MS-ESI calculated $[M-100+H]^+$452, found 452.

Step 3

Compound 8-4 (30.0 mg, 0.0544 mmol) was dissolved in ethyl acetate (5 mL), and a solution of hydrogen chloride in ethyl acetate (4 mol/L, 1 mL) was added. The reaction solution was stirred at 25° C. for 1 hour. The reaction solution was concentrated under reduced pressure, and the residue was purified by preparative high performance liquid chromatography (acidic, hydrochloric acid system) to obtain hydrochloride of compound 8. $^1$H NMR (400 MHz, $CD_3OD$) δ 8.02 (s, 1H), 7.58 (t, J=8.0 Hz, 1H), 7.26 (t, J=8.0 Hz, 1H), 7.20-7.09 (m, 4H), 5.04 (s, 2H), 4.22-4.20 (m, 1H), 3.94 (s, 3H), 3.65-3.61 (m, 1H), 3.29-3.16 (m, 3H), 2.19-2.09 (m, 1H), 1.92-1.67 (m, 2H), 1.64-1.49 (m, 1H). MS-ESI calculated $[M+H]^+$452, found 452.

Embodiment 9

9

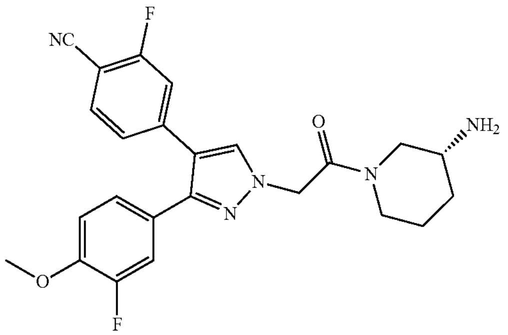

Synthetic Route:

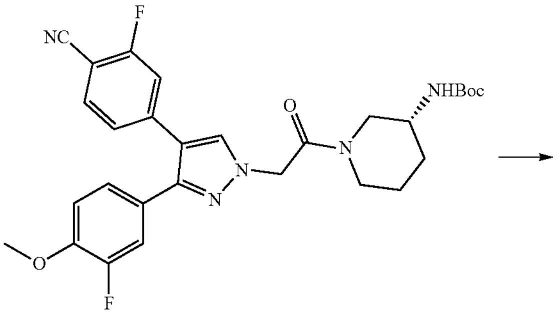

8-5

Hydrochloride of compound 9

Compound 8-5 (30.0 mg, 0.0544 mmol) was dissolved in ethyl acetate (5 mL), and a solution of hydrogen chloride in ethyl acetate (4 mol/L, 1 mL) was added. The reaction solution was stirred at 25° C. for 1 hour. The reaction solution was concentrated under reduced pressure, and the residue was purified by preparative high performance liquid chromatography (acidic, hydrochloric acid system) to obtain hydrochloride of compound 9. $^1$H NMR (400 MHz, $CD_3OD$) δ8.06 (s, 1H), 7.66 (t, J=8.0 Hz, 1H), 7.28-7.22 (m, 2H), 7.21-7.07 (m, 3H), 5.30 (s, 2H), 4.16-4.06 (m, 1H), 3.90 (s, 3H), 3.77-3.67 (m, 1H), 3.53-3.48 (m, 2H), 3.36 (s, 1H), 2.23-2.09 (m, 1H), 2.01-1.90 (m, 1H), 1.89-1.70 (m, 2H). MS-ESI calculated $[M+H]^+$452, found 452.

Embodiment 10

10

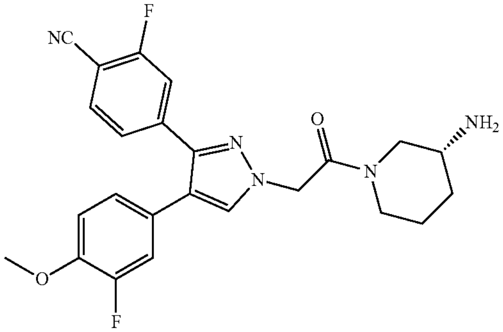

Synthetic Route:
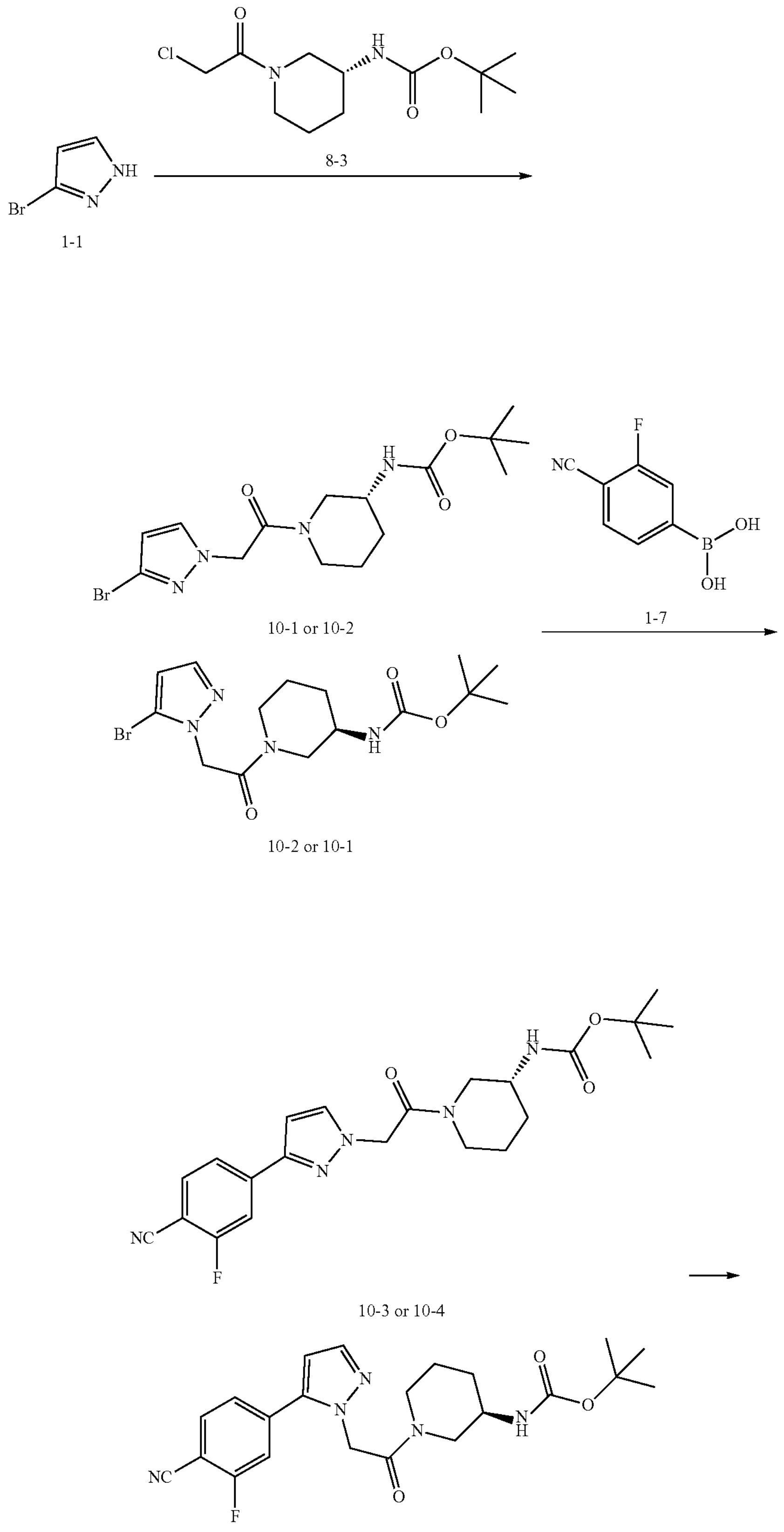
1-1
10-1 or 10-2
10-2 or 10-1
10-3 or 10-4
10-4 or 10-3

-continued
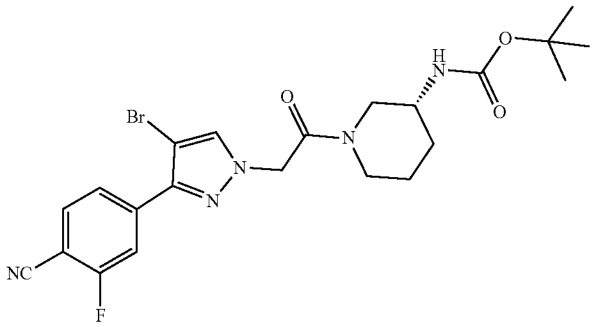
10-5 or 10-6
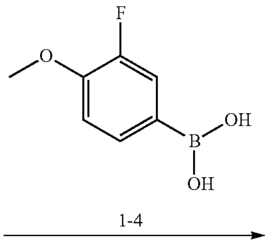
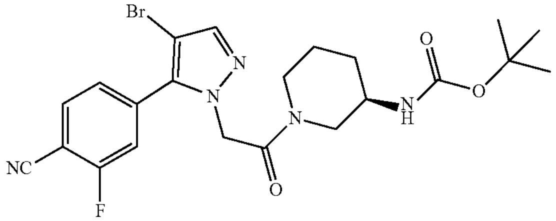
10-6 or 10-5
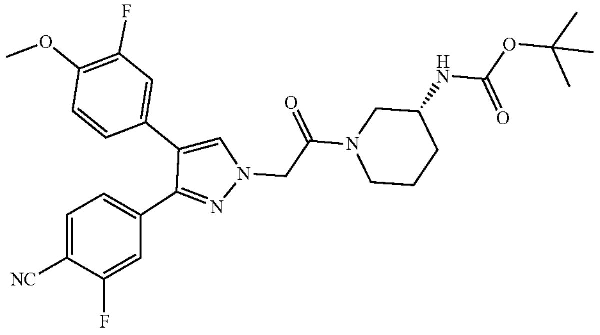
10-7
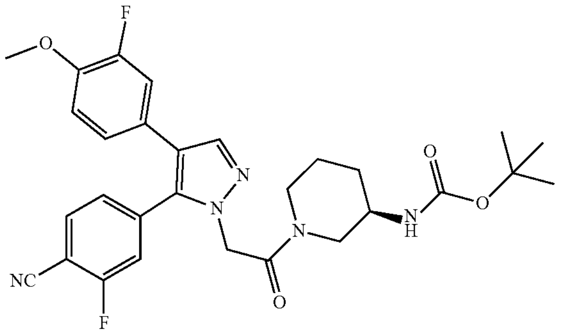
10-8

-continued

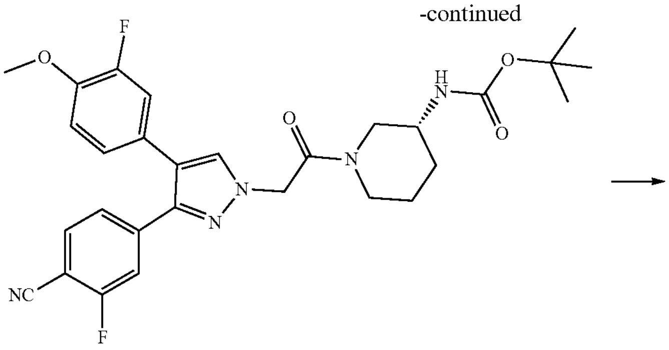

10-7

Step 1

Under the protection of nitrogen, compound 1-1 (500 mg, 3.40 mmol) was dissolved in N,N-dimethylformamide (50 mL), then compound 8-3 (1.13 g, 6.8 mmol) and cesium carbonate (3.33 g, 10.21 mmol) were added, and the reaction solution was stirred at 100° C. for 12 hours. Water (100 mL) was added to the reaction solution, and then the mixture was extracted with ethyl acetate (100 mL×2). The organic phase was washed with saturated brine (10 mL×3), dried over anhydrous sodium sulfate, filtered, and concentrated under reduced pressure; the residue was separated and purified by silica gel column chromatography to obtain a mixture of compound 10-1 and compound 10-2. MS-ESI calculated $[M-56+H]^+$331 and 333, found 331 and 333.

Step 2

Under the protection of nitrogen, the mixture of compound 10-1 and compound 10-2 (1.00 g, 2.58 mmol) was dissolved in 1,4-dioxane (50 mL) and water (10 mL), then compound 1-7 (426 mg, 2.58 mmol), potassium phosphate (1.10 g, 5.16 mmol) and dichloro[1,1E bis(di-tert-butylphosphino)ferrocene]palladium(II) (336 mg, 0.516 mmol) were added, and the reaction solution was stirred at 90° C. for 12 hours. Water (50 mL) was added to the reaction solution, and then the mixture was extracted with ethyl acetate (50 mL×2). The organic phase was washed with saturated brine (30 mL×3), dried over anhydrous sodium sulfate, filtered, and concentrated under reduced pressure. The residue was separated and purified by silica gel column chromatography to obtain a mixture of compound 10-3 and compound 10-4. MS-ESI calculated [M−56+H]>372, found 372.

Step 3

The mixture of compound 10-3 and compound 10-4 (500 mg, 1.17 mmol) and N-bromosuccinimide (208 mg, 1.17 mmol) were dissolved in N,N-dimethylformamide (10 mL). The reaction mixture was stirred at 25° C. for 1 hour under the protection of nitrogen. Water (50 mL) was added to the reaction solution, and then the mixture was extracted with ethyl acetate (30 mL×2). The organic phase was washed with saturated brine (30 mL×3), dried over anhydrous sodium sulfate, filtered, and concentrated under reduced pressure. The residue was separated and purified by silica gel column chromatography to obtain a mixture of compound 10-5 and compound 10-6. MS-ESI calculated $[M-56+H]^+$450 and 452, found 450 and 452.

Step 4

Under the protection of nitrogen, the mixture of compound 10-5 and compound 10-6 (440 mg, 825 mmol) was dissolved in 1,4-dioxane (10 mL) and water (2 mL), then compound 1-4 (140 mg, 825 mmol), potassium phosphate (350 mg, 1.65 mmol) and [1,1E bis(diphenylphosphino) ferrocene]dichloropalladium(II) (120 mg, 165 μmol) were added, and the reaction solution was stirred at 90° C. for 12 hours. Water (50 mL) was added to the reaction solution, and then the mixture was extracted with ethyl acetate (30 mL×2). The organic phase was washed with saturated brine (30 mL×2), dried over anhydrous sodium sulfate, filtered, concentrated under reduced pressure, and the residue was separated by preparative high performance liquid chromatography (acidic condition, column type: Venusil ASB Phenyl 150×30 mm×5 μm; mobile phase: [water (0.05% HCl)-acetonitrile]; B (acetonitrile) %: 60%-90%, 10 minutes) to obtain compound 10-7 (retention time: 4.80 minutes) and compound 10-8 (retention time: 4.59 minutes). Compound 10-7 $^1$H NMR (400 MHz, $CDCl_3$) δ 7.76-7.75 (m, 1H), 7.68-7.65 (m, 1H), 7.46-7.40 (m, 2H), 7.11-7.01 (m, 3H), 5.08 (s, 2H), 4.60 (s, 1H), 3.93 (s, 3H), 3.89-3.74 (m, 2H), 3.65 (s, 1H), 3.36 (s, 2H), 2.09-1.85 (m, 2H), 1.77-1.63 (m, 2H), 1.48 (s, 9H). MS-ESI calculated $[M-56+H]^+$496, found 496.

Step 5

Compound 10-7 (150 mg, 0.272 mmol) was dissolved in ethyl acetate (5 mL), and a solution of hydrogen chloride in ethyl acetate (4 mol/L, 5 mL) was added. The reaction solution was stirred at 25° C. for 1 hour. The reaction solution was concentrated under reduced pressure, and the residue was purified by preparative high performance liquid chromatography (acidic, hydrochloric acid system) to obtain hydrochloride of compound 10. $^1$H NMR (400 MHz, $CD_3OD$) δ 7.80 (s, 1H), 7.68 (t, J=7.4 Hz, 1H), 7.46-7.39 (m, 2H), 7.13-7.00 (m, 3H), 5.30 (s, 2H), 4.21-4.07 (m, 1H), 3.89 (s, 3H), 3.87-3.45 (m, 2H), 3.45-3.32 (m, 2H), 2.23-1.86 (m, 2H), 1.83-1.65 (m, 2H). MS-ESI calculated $[M+H]^+$452, found 452.

Embodiment 11

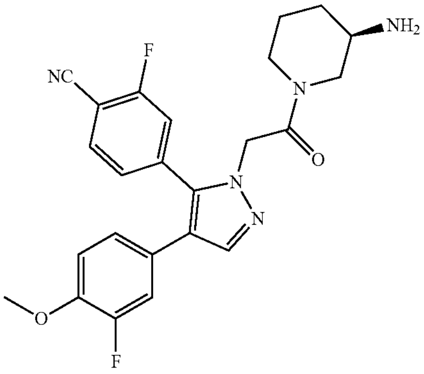

11

Synthetic Route:

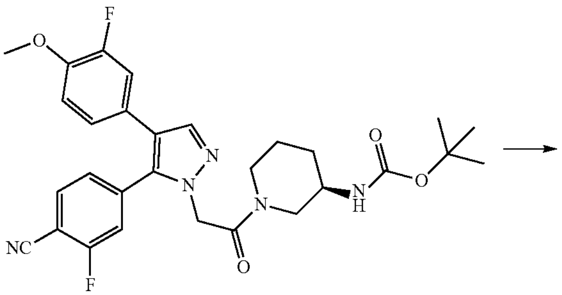

10-8

Hydrochloride of compound 11

Compound 10-8 (30.0 mg, 54.4 μmol) was dissolved in ethyl acetate (3 mL), and a solution of hydrogen chloride in ethyl acetate (4 mol/L, 9 mL) was added. The reaction solution was stirred at 25° C. for 1 hour. The reaction solution was concentrated under reduced pressure, and the residue was separated and purified by preparative high performance liquid chromatography (acidic, hydrochloric acid system) to obtain hydrochloride of compound 11. $^1$H NMR (400 MHz, $CD_3OD$) δ 7.86 (t, J=7.4 Hz, 1H), 7.82 (s, 1H), 7.45-7.30 (m, 2H), 7.05-6.82 (m, 3H), 5.15-5.04 (m, 2H), 4.19-3.97 (m, 1H), 3.84 (s, 3H), 3.77-3.53 (m, 1H), 3.40-3.33 (m, 1H), 3.28-3.26 (m, 2H), 2.13-2.11 (m, 1H), 1.87-1.59 (m, 3H). MS-ESI calculated $[M+H]^+$452, found 452.

Embodiment 12

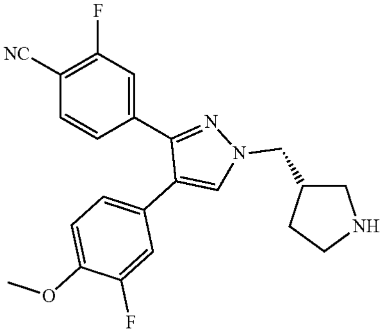

12

Synthetic Route:

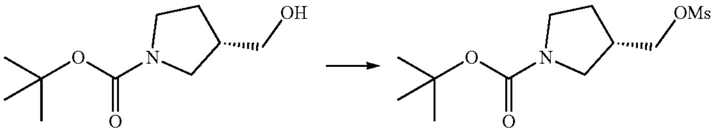

12-1

12-2

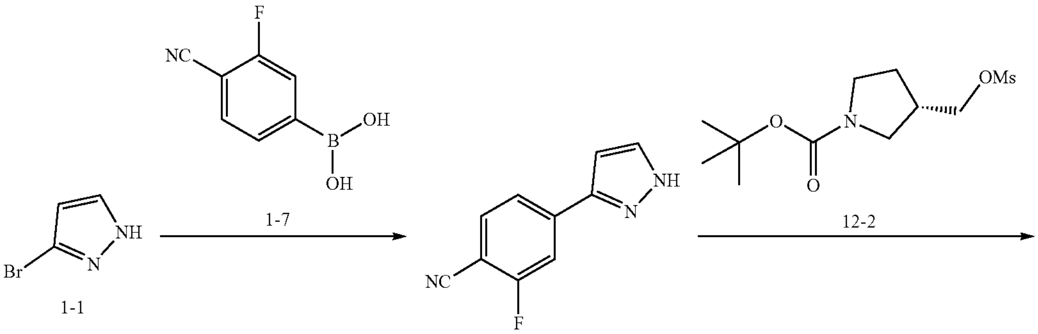

1-1

12-3

-continued

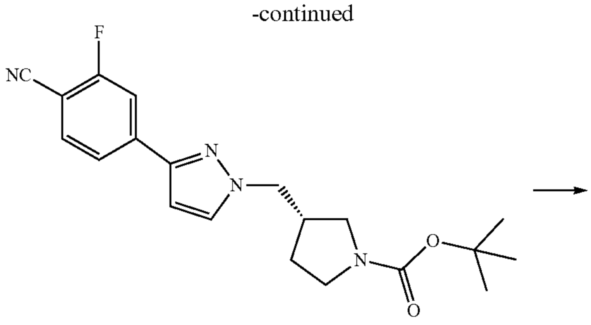

12-4

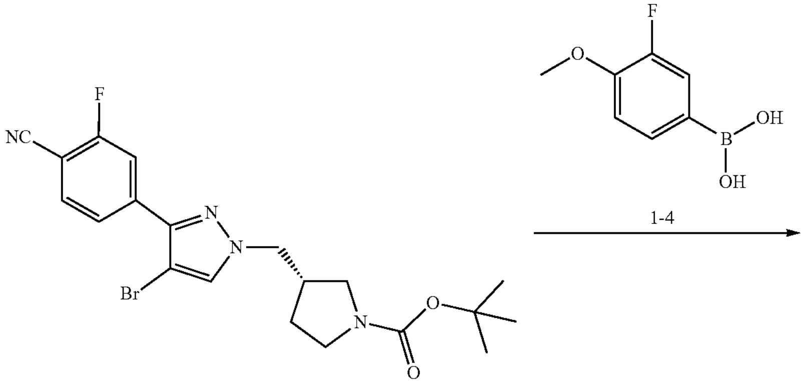

12-5

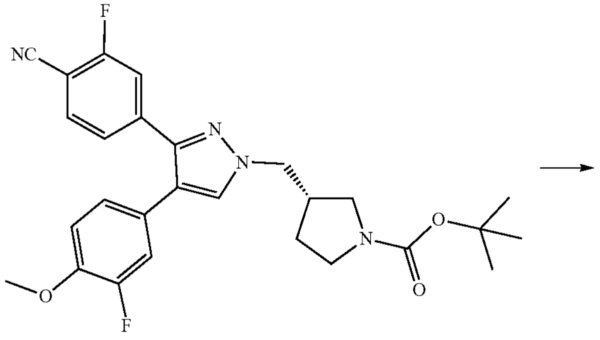

Hydrochloride of compound 12

12-6

Step 1

Under the protection of nitrogen, compound 12-1 (2.00 g, 9.94 mmol) and triethylamine (1.01 g, 9.94 mmol) were dissolved in dichloromethane (20 mL), then methanesulfonyl chloride (1.71 g, 14.9 mmol) was added, and the reaction solution was stirred at 25° C. for 12 hours. Saturated sodium bicarbonate solution (20 mL) was added to the reaction solution, and then the mixture was extracted with dichloromethane (30 mL×3). The organic phase was washed with saturated brine (30 mL×3), dried over anhydrous sodium sulfate, filtered, and concentrated under reduced pressure. The residue was separated and purified by silica gel column chromatography to obtain compound 12-2. 1H NMR (400 MHz, $CDCl_3$) δ 4.22-4.13 (m, 2H), 3.53-3.34 (m, 3H), 3.19-3.13 (m, 1H), 3.02 (s, 3H), 2.63-2.60 (m, 1H), 1.49-1.47 (m, 2H), 1.45 (s, 9H).

Step 2

Under the protection of nitrogen, compound 1-1 (1.00 g, 6.80 mmol) was dissolved in 1,4-dioxane (50 mL) and water (10 mL), then compound 1-7 (1.23 g, 7.48 mmol), potassium phosphate (2.89 g, 13.6 mmol) and dichloro[1,1'-bis(di-tert-butylphosphino)ferrocene]palladium(II) (665 mg, 1.02 mmol) were added, and the reaction solution was stirred at 90° C. for 12 hours. Water (150 mL) was added to the reaction solution, and then the mixture was extracted with ethyl acetate (100 mL×2). The organic phase was washed with saturated brine (100 mL×1), dried over anhydrous sodium sulfate, filtered, and concentrated under reduced pressure. The residue was separated and purified by silica gel column chromatography to obtain compound 12-3. MS-ESI calculated $[M+H]^+$188, found 188.

Step 3

Under the protection of nitrogen, compound 12-3 (500 mg, 2.60 mmol) was dissolved in N,N-dimethylformamide (30 mL), then compound 12-2 (746 mg, 2.67 mmol) and cesium carbonate (2.61 g, 8.01 mmol) were added, and the reaction solution was stirred at 100° C. for 12 hours. Water (200 mL) was added to the reaction solution, and then the mixture was extracted with ethyl acetate (50 mL×2). The organic phase was washed with saturated brine (100 mL×3), dried over anhydrous sodium sulfate, filtered, and concentrated under reduced pressure. The residue was separated and purified by silica gel column chromatography to obtain compound 12-4. 1H NMR (400 MHz, $CDCl_3$) δ 7.70-7.59 (m, 3H), 7.48-7.41 (m, 1H), 6.65-6.55 (m, 1H), 3.69-3.26 (m, 4H), 3.23-3.06 (m, 1H), 2.85-2.75 (m, 1H), 2.07-2.01 (m, 2H), 1.75-1.65 (m, 1H), 1.46 (s, 9H). MS-ESI calculated $[M-56+H]^+$315, found 315.

Step 4

Compound 12-4 (500 mg, 1.35 mmol) and N-bromosuccinimide (240 mg, 1.35 mmol) were dissolved in N,N-dimethylformamide (10 mL). The reaction mixture was stirred at 25° C. for 2 hours under the protection of nitrogen. Water (100 mL) was added to the reaction solution, and then the mixture was extracted with ethyl acetate (50 mL×2). The organic phase was washed with saturated brine (50 mL×3), dried over anhydrous sodium sulfate, filtered, and concentrated under reduced pressure. The residue was separated and purified by silica gel column chromatography to obtain compound 12-5. $^1H$ NMR (400 MHz, $CDCl_3$) δ 7.94-7.82 (m, 2H), 7.70-7.63 (m, 1H), 7.52 (s, 1H), 3.52-3.5 (m, 2H), 3.37-3.35 (m, 1H), 3.20-3.10 (m, 1H), 2.85-2.75 (m, 1H), 2.06-2.01 (m, 3H), 1.75-1.65 (m, 1H), 1.47 (s, 9H). MS-ESI calculated $[M-56+H]^+$393 and 395, found 393 and 395.

Step 5

Under the protection of nitrogen, compound 12-5 (450 mg, 1.00 mmol) was dissolved in 1,4-dioxane (8 mL) and water (2 mL), then compound 1-4 (204 mg, 1.20 mmol) and potassium phosphate (638 mg, 3.00 mmol) were added, and [1,1′-bis(diphenylphosphino)ferrocene]dichloropalladium (II) (36.6 mg, 50.1 μmol) was added, and the reaction solution was stirred at 90° C. for 12 hours. Water (50 mL) was added to the reaction solution; then the mixture was extracted with ethyl acetate (30 mL×3). The organic phase was washed with saturated brine (50 mL×1), dried over anhydrous sodium sulfate, filtered, and concentrated under reduced pressure. The residue was separated and purified by silica gel column chromatography to obtain compound 12-6. MS-ESI calculated $[M-56+H]^+$439, found 439.

Step 6

Compound 12-6 (300 mg, 0.607 μmol) was dissolved in ethyl acetate (5 mL), and a solution of hydrogen chloride in ethyl acetate (4 mol/L, 10 mL) was added. The reaction solution was stirred at 25° C. for 1 hour. The reaction solution was concentrated under reduced pressure, and the residue was purified by preparative high performance liquid chromatography (acidic, hydrochloric acid system) to obtain hydrochloride of compound 12. $^1H$ NMR (400 MHz, MeOD) δ 7.88 (s, 1H), 7.66 (t, J=7.4 Hz, 1H), 7.47-7.38 (m, 2H), 7.09 (t, J=8.7 Hz, 1H), 7.06-6.96 (m, 2H), 4.45-4.30 (m, 2H), 3.88 (s, 3H), 3.54-3.40 (m, 2H), 3.38-3.31 (m, 1H), 3.25-3.20 (m, 1H), 3.06-2.99 (m, 1H), 2.29-2.18 (m, 1H), 1.96-1.85 (m, 1H). MS-ESI calculated $[M+H]^+$395, found 395.

Embodiment 13

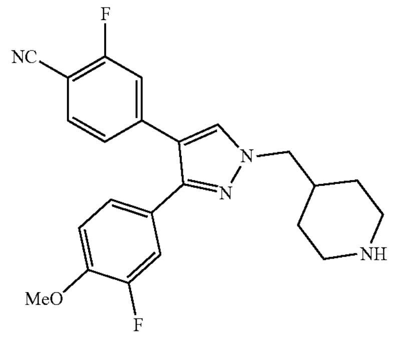

13

Synthetic Route:

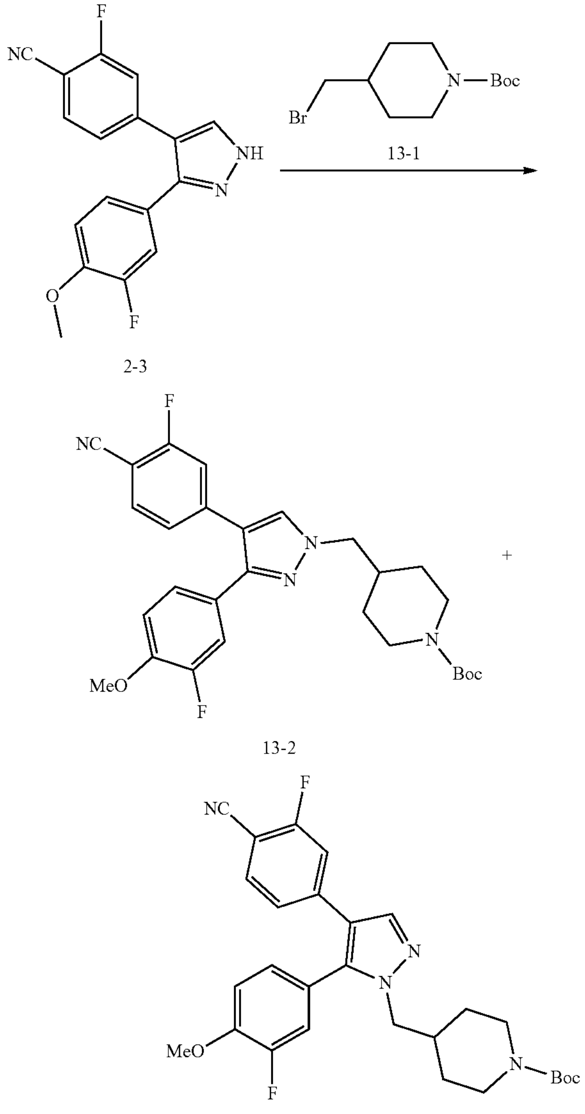

2-3

13-1

+

13-2

13-3

-continued

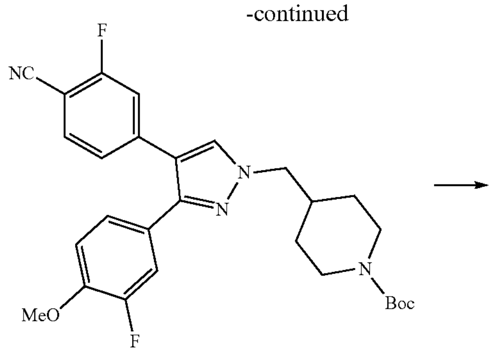

13-2

Hydrochloride of compound 13

Step 1

Compound 2-3 (400 mg, 1.28 mmol) was dissolved in anhydrous N,N-dimethylformamide (8 mL), then sodium hydride (56.5 mg, 1.41 mmol, 60%) was added to the reaction solution, and the reaction solution was reacted at 50° C. for 0.5 hours. Compound 13-1 (357 mg, 1.28 mmol) was then added to the reaction solution, and the reaction solution was stirred at 70° C. for 2.5 hours. The reaction solution was quenched with saturated ammonium chloride aqueous solution (50 mL) at 0° C., and extracted with ethyl acetate (50 mL×2). The organic phase was combined, washed with water (50 mL×3) and saturated brine (50 mL×1) sequentially, dried over anhydrous sodium sulfate, filtered, and the filtrate was concentrated under reduced pressure, and the crude product was separated by preparative high performance liquid chromatography (neutral condition, column type: Waters Xbridge 150x25 mm×5 μm; mobile phase: [water (10 mM NH4HCO3)-acetonitrile]; B %: 62%-62%, 10 min) to obtain compound 13-2 (retention time: 10.0 min) and compound 13-3 (retention time: 8.5 min). Compound 13-2 $^1H$ NMR (400 MHz, $CDCl_3$) δ 7.56-7.51 (m, 2H), 7.24 (dd, J=12.0, 2.0 Hz, 1H), 7.17-7.12 (m, 3H), 6.98-6.93 (m, 1H), 4.17-4.12 (m, 2H), 4.05 (d, J=7.2 Hz, 2H), 3.94 (s, 3H), 2.76-2.69 (m, 2H), 2.23-2.14 (m, 1H), 1.68-1.65 (m, 2H), 1.48 (s, 9H), 1.32-1.19 (m, 2H). MS-ESI calculated $[M-56+H]^+$453, found 453. Compound 13-3 $^1H$ NMR (400 MHz, $CDCl_3$) δ 7.82 (s, 1H), 7.48-7.45 (m, 1H), 7.11 (t, J=8.4 Hz, 1H), 7.04-6.95 (m, 4H), 4.07 (s, 2H), 4.01 (s, 3H), 3.87 (d, J=7.2 Hz, 2H), 2.69-2.63 (m, 2H), 2.15-2.09 (m, 1H), 1.48 (s, 2H), 1.45 (s, 9H), 1.07-0.97 (m, 2H). MS-ESI calculated $[M-56+H]^+$453, found 453.

Step 2

Compound 13-2 (180 mg, 0.354 mmol) was dissolved in ethyl acetate (5 mL), and a solution of hydrogen chloride in ethyl acetate (4 mol/L, 5 mL) was added. The reaction solution was stirred at 20° C. for 2 hours, concentrated under reduced pressure, and the crude product was separated and purified by preparative high performance liquid chromatography (acidic, hydrochloric acid system) to obtain hydrochloride of compound 13. $^1H$ NMR (400 MHz, $CD_3OD$) δ 8.10 (s, 1H), 7.69-7.66 (m, 1H), 7.28-7.25 (m, 2H), 7.22-7.18 (m, 1H), 7.16-7.10 (m, 2H), 4.21 (d, J=7.2 Hz, 2H), 3.92 (s, 3H), 3.47-3.44 (m, 2H), 3.07-3.00 (m, 2H), 2.39-2.30 (m, 1H), 1.95-1.92 (m, 2H), 1.65-1.54 (m, 2H). MS-ESI calculated $[M+H]^+$409, found 409.

Embodiment 14

14

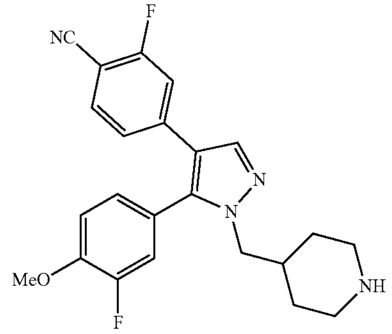

Synthetic Route:

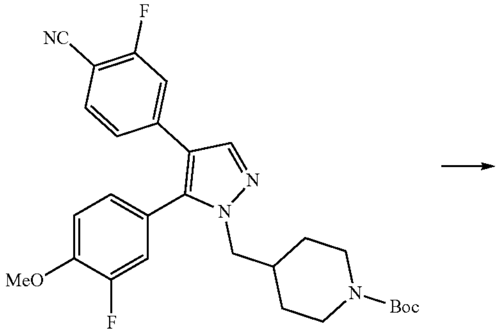

13-3

Hydrochloride of compound 14

Compound 13-3 (120 mg, 0.236 mmol) was dissolved in ethyl acetate (5 mL), and a solution of hydrogen chloride in ethyl acetate (4 mol/L, 5 mL) was added. The reaction solution was stirred at 20° C. for 2 hours, concentrated under reduced pressure, and the crude product was separated and purified by preparative high performance liquid chromatography (acidic, hydrochloric acid system) to obtain hydrochloride of compound 14. $^1H$ NMR (400 MHz, $CD_3OD$) δ 8.02 (s, 1H), 7.62-7.58 (m, 1H), 7.35-7.30 (m, 1H), 7.23-7.20 (m, 1H), 7.18-7.14 (m, 3H), 4.02 (d, J=7.2 Hz, 2H), 3.99 (s, 3H), 3.37-3.34 (m, 2H), 2.97-2.90 (m, 2H), 2.23-2.15 (m, 1H), 1.78-1.75 (m, 2H), 1.41-1.31 (m, 2H). MS-ESI calculated $[M+H]^+$409, found 409.

Embodiment 15
15
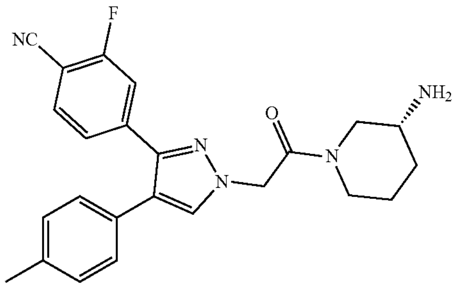
Synthetic Route:
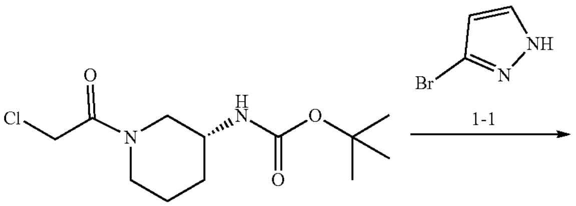
8-3
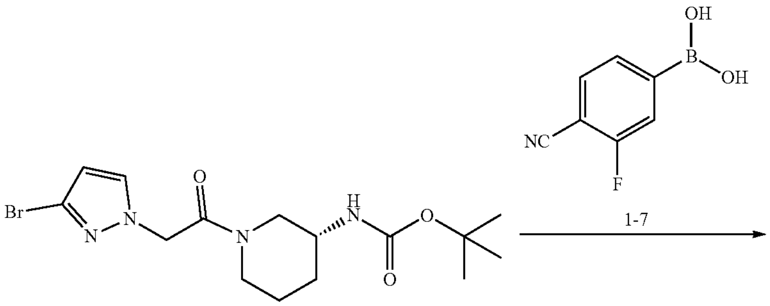
15-1
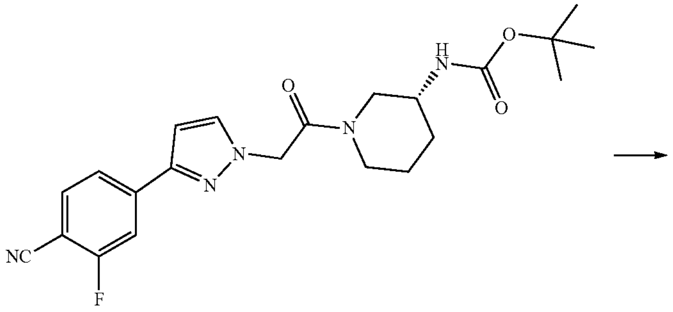
15-2

-continued

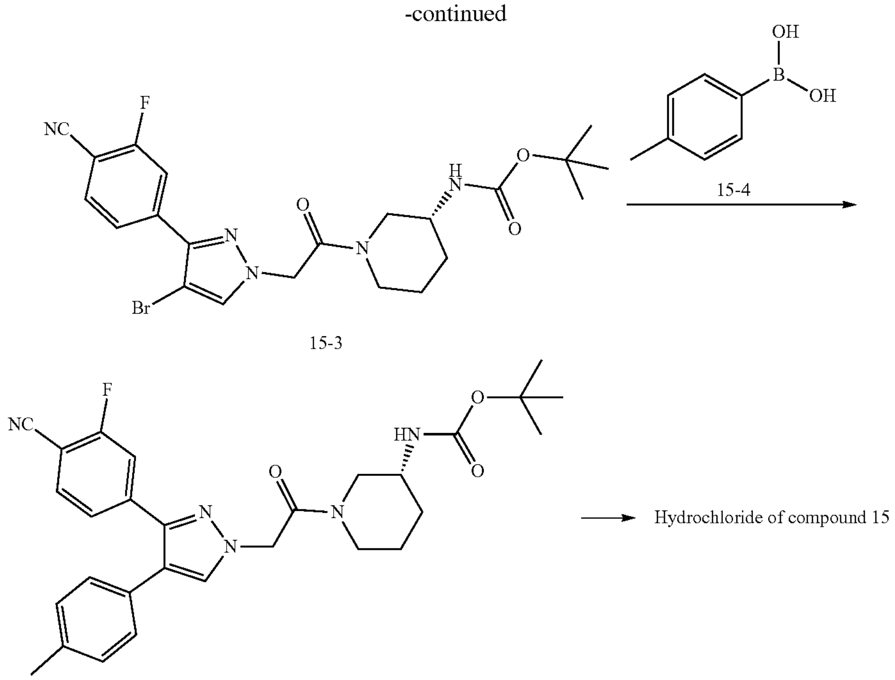

15-3

15-5

Step 1

Compound 8-3 (3.99 g, 12.3 mmol) and compound 1-1 (1.50 g, 10.2 mmol) were dissolved in N, N-dimethylformamide (10.0 mL), then cesium carbonate (9.98 g, 30.6 mmol) was added, and the reaction solution was stirred at 100° C. for 6 hours under the protection of nitrogen. Water (200 mL) was added to the reaction solution, and the mixture was extracted with ethyl acetate (100 mL×3). The organic phase was washed with saturated brine (100 mL×3), dried over anhydrous sodium sulfate, filtered, concentrated under reduced pressure, and separated and purified by silica gel column chromatography (1/1, petroleum ether/ethyl acetate, Rf=0.30) to obtain compound 15-1. MS-ESI calculated $[M-56+H]^+$333, found 333.

Step 2

Compound 15-1 (1.00 g, 2.58 mmol) and compound 1-7 (0.426 g, 2.58 mmol) were dissolved in 1,4-dioxane (30.0 mL) and water (6.00 mL), then potassium carbonate (1.10 g, 5.16 mmol) and dichloro[1,1'-bis(di-tert-butylphosphino) ferrocene]palladium(II) (337 mg, 516 μmol) were added, and the reaction solution was stirred at 90° C. for 12 hours under the protection of nitrogen. Water (50 mL) was added to the reaction solution, and the mixture was extracted with ethyl acetate (30 mL×3). The organic phase was washed with saturated brine (30 mL), dried over anhydrous sodium sulfate, filtered, concentrated under reduced pressure, and separated and purified by silica gel column chromatography (1/2, petroleum ether/ethyl acetate, Rf=0.31) to obtain compound 15-2. MS-ESI calculated $[M-56+H]^+$428, found 428.

Step 3

Compound 15-2 (1.87 g, 3.99 mmol) and N-bromosuccinimide (710 mg, 3.99 mmol) were dissolved in N,N-dimethylformamide (10 mL). The reaction solution was stirred at 25° C. for 1 hour. Water (50 mL) was added to the reaction solution, and then the mixture was extracted with ethyl acetate (30 mL×3). The organic phase was washed with saturated brine (50 mL×3), dried over anhydrous sodium sulfate, filtered, and concentrated under reduced pressure. The residue was separated by preparative high performance liquid chromatography (column: Welch Xtimate C18 150*25 mm*5 μm; mobile phase A: ammonia aqueous solution with a volume fraction of 0.05%; mobile phase B: acetonitrile B %: 55%, 9 minutes) to obtain compound 15-3. $^1$H NMR (400 MHz, $CDCl_3$) δ=7.94-7.83 (m, 2H), 7.73-7.60 (m, 2H), 5.04 (s, 2H), 4.59-4.56 (m, 1H), 3.81-3.59 (m, 2H), 3.40-3.34 (m, 2H), 2.01-1.99 (m, 1H), 1.82-1.57 (m, 3H), 1.48 (s, 9H). MS-ESI calculated $[M+Na]^+$528, found 528.

Step 4

Under the protection of nitrogen, compound 15-3 (200 mg, 395 mmol) was dissolved in 1,4-dioxane (10.0 mL) and water (2.00 mL), then compound 15-4 (53.7 mg, 395 mmol), potassium phosphate (168 mg, 790 μmol) and [1,1' bis (diphenylphosphino)ferrocene]dichloropalladium(II) (57.8 mg, 79.0 μmol) were added, and the reaction solution was stirred at 90° C. for 12 hours. The reaction solution was concentrated under reduced pressure, and the residue was separated and purified by silica gel column chromatography (1/1, petroleum ether/ethyl acetate, Rf=0.30) to obtain compound 15-5. $^1$H NMR (400 MHz, $CDCl_3$) δ 7.75-7.74 (m, 1H), 7.67-7.62 (m, 1H), 7.44-7.41 (m, 2H), 7.21-7.16 (m, 4H), 5.33-5.17 (m, 2H), 3.99-3.87 (m, 1H), 3.55-3.54 (m, 1H), 3.24-3.00 (m, 2H), 2.36 (s, 3H), 2.00-1.97 (m, 1H), 1.85-1.80 (m, 1H), 1.62-1.53 (m, 2H), 1.44 (s, 9H). MS-ESI calculated $[M-56+H]^+$462, found 462.

Step 5

Compound 15-5 (180 mg, 348 μmol) was dissolved in ethyl acetate (5.00 mL), and a solution of hydrogen chloride in ethyl acetate (4 mol/L, 5.00 mL) was added. The reaction solution was stirred at 25° C. for 1 hour. The reaction solution was concentrated under reduced pressure, and the residue was separated and purified by preparative high performance liquid chromatography (Venusil ASB Phenyl 150*30 mm*5 μm; mobile phase A: 0.05% hydrochloric acid aqueous solution; mobile phase B: acetonitrile; B %: 35%-65%, 9 min) to obtain hydrochloride of compound 15. $^1$H NMR (400 MHz, $CD_3OD$) δ 7.78 (s, 1H), 7.68-7.64 (m, 1H), 7.43-7.41 (m, 2H), 7.20-7.15 (m, 4H), 5.30 (s, 2H), 4.18-4.04 (m, 1H), 3.77-3.74 (m, 1H), 3.49-3.34 (m, 3H), 2.36 (s, 3H), 2.18-2.15 (m, 1H), 1.95-1.76 (m, 3H). MS-ESI calculated $[M+H]^+$418, found 418.

Embodiment 16

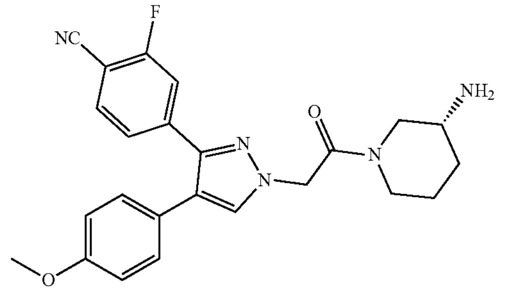

16

Synthetic Route:

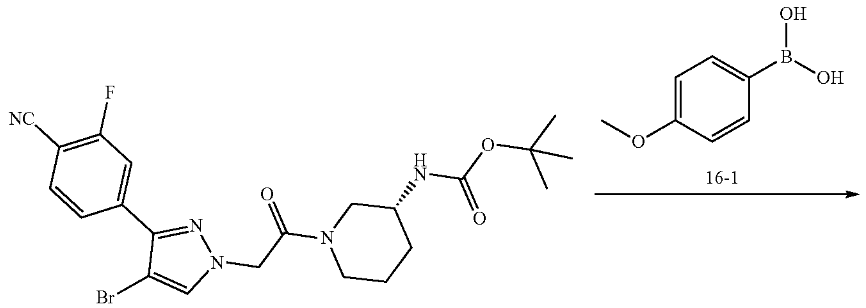

15-3

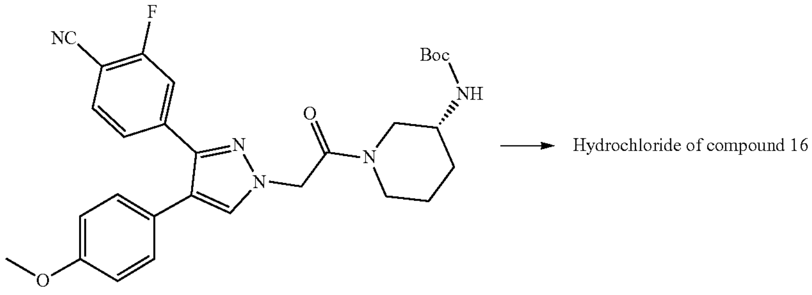

16-2

Step 1

Under the protection of nitrogen, compound 15-3 (200 mg, 395 mmol) was dissolved in 1,4-dioxane (10.0 mL) and water (2.00 mL), then compound 16-1 (60.0 mg, 0.395 mmol), potassium phosphate (168 mg, 790 μmol) and [1,1'-bis(diphenylphosphino)ferrocene]dichloropalladium (II) (57.8 mg, 79.0 μmol) were added, and the reaction solution was stirred at 90° C. for 12 hours. The reaction solution was concentrated under reduced pressure, and the residue was separated and purified by silica gel column chromatography (1/1, petroleum ether/ethyl acetate, Rf=0.30) to obtain compound 16-2. $^1$H NMR (400 MHz, $CDCl_3$) δ 7.70-7.68 (m, 1H), 7.64-7.59 (m, 1H), 7.41-7.38 (m, 2H), 7.18 (d, J=8.8 Hz, 2H), 6.91 (d, J=8.8 Hz, 2H), 5.29-5.13 (m, 2H), 4.14-3.82 (m, 2H), 3.80 (s, 3H), 3.55-3.54 (m, 1H), 3.27-2.95 (m, 2H), 1.97-1.95 (m, 1H), 1.86-1.76 (m, 1H), 1.66-1.53 (m, 2H), 1.44 (s, 9H). MS-ESI calculated $[M-56+H]^+$478, found 478.

Step 2

Compound 16-2 (120 mg, 225 μmol) was dissolved in ethyl acetate (5.00 mL), and a solution of hydrogen chloride in ethyl acetate (4 mol/L, 562 μL) was added. The reaction solution was stirred at 25° C. for 1 hour. The reaction solution was concentrated under reduced pressure, and the residue was separated and purified by preparative high performance liquid chromatography (Venusil ASB Phenyl 150*30 mm*5 μm; mobile phase A: 0.05% hydrochloric acid aqueous solution; mobile phase B: acetonitrile; B %: 35%-65%, 9 min) to obtain hydrochloride of compound 16. $^1$H NMR (400 MHz, $CD_3OD$) δ 7.75 (s, 1H), 7.68-7.66 (m, 1H), 7.42 (d, J=8.0 Hz, 2H), 7.20 (d, J=8.0 Hz, 2H), 6.94 (d, J=8.0 Hz, 2H), 5.30 (s, 2H), 4.18-4.16 (m, 1H), 3.81 (s, 3H), 3.79-3.74 (m, 1H), 3.50-3.40 (m, 2H), 3.36-3.33 (m, 1H), 2.19-2.16 (m, 1H), 2.05-1.93 (m, 1H), 1.83-1.76 (m, 2H). MS-ESI calculated [M+H]$^+$434, found 434.

Embodiment 17

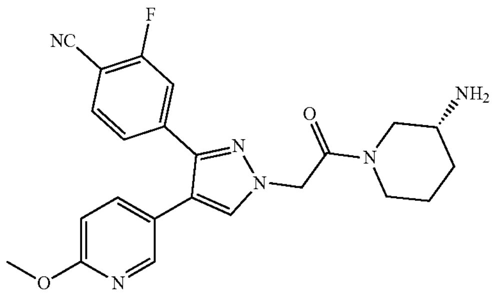

17

Synthetic Route:

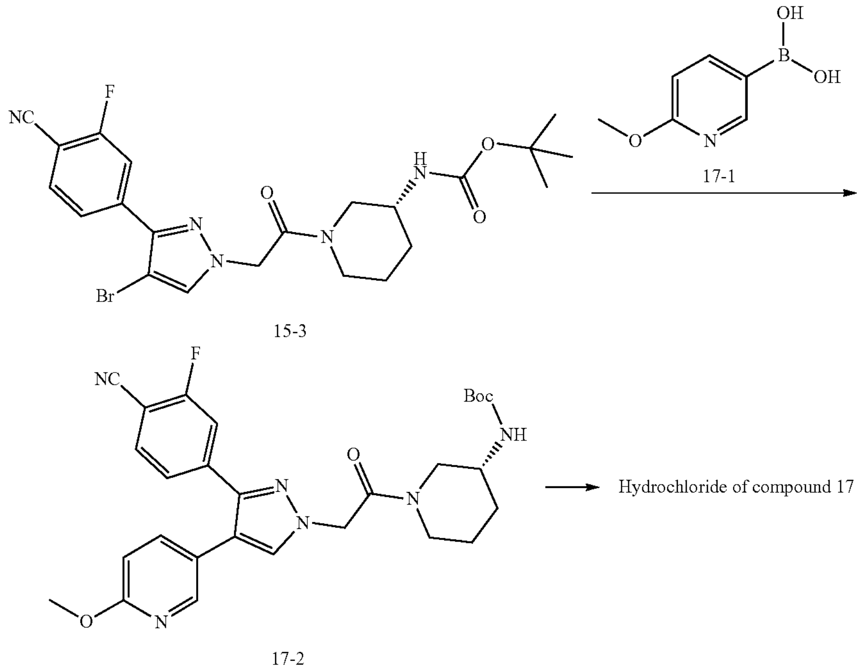

15-3

17-1

17-2

Step 1

Under the protection of nitrogen, compound 15-3 (200 mg, 395 μmol) was dissolved in 1,4-dioxane (10.0 mL) and water (2.00 mL), then compound 17-1 (60.4 mg, 395 μmol), potassium phosphate (168 mg, 790 μmol) and [1,1′ bis (diphenylphosphino)ferrocene]dichloropalladium(II) (57.80 mg, 79.0 μmol) were added, and the reaction solution was stirred at 90° C. for 12 hours. The reaction solution was concentrated under reduced pressure, and the residue was separated and purified by silica gel column chromatography (1/1, petroleum ether/ethyl acetate, Rf=0.30) to obtain compound 17-2. $^1$H NMR (400 MHz, $CDCl_3$) δ 8.05 (s, 1H), 7.81-7.63 (m, 3H), 7.56-7.55 (m, 1H), 7.46-7.36 (m, 2H), 6.83-6.79 (m, 1H), 5.33-5.14 (m, 2H), 4.17-3.96 (m, 1H), 3.92 (s, 3H), 3.85-3.73 (m, 1H), 3.61-3.54 (m, 1H), 3.28-2.96 (m, 2H), 2.01-1.92 (m, 1H), 1.87-1.76 (m, 1H), 1.68-1.54 (m, 2H), 1.44 (s, 9H). MS-ESI calculated [M−56+H]$^+$ 479, found 479.

Step 2

Compound 17-2 (140 mg, 262 μmol) was dissolved in ethyl acetate (5.00 mL), and a solution of hydrogen chloride in ethyl acetate (4 mol/L, 1.00 mL) was added. The reaction solution was stirred at 25° C. for 1 hour. The reaction solution was concentrated under reduced pressure, and the residue was separated and purified by preparative high performance liquid chromatography (Venusil ASB Phenyl 150*30 mm*5 μm; mobile phase A: 0.05% hydrochloric acid aqueous solution; mobile phase B: acetonitrile; B %: 35%-65%, 9 min) to obtain hydrochloride of compound 17. $^1$H NMR (400 MHz, $CD_3OD$) δ 8.33 (s, 1H), 8.25 (d, J=8.8 Hz, 1H), 8.10 (s, 1H), 7.75 (t, J=7.6 Hz, 1H), 7.54-7.50 (m, 2H), 7.43 (d, J=7.6 Hz, 1H), 5.40 (s, 2H), 4.24 (s, 3H), 4.19-4.05 (m, 1H), 3.77-3.75 (m, 1H), 3.50-3.33 (m, 3H), 2.20-2.17 (m, 1H), 1.99-1.78 (m, 3H). MS-ESI calculated [M+H]$^+$435, found 435.

Embodiment 18

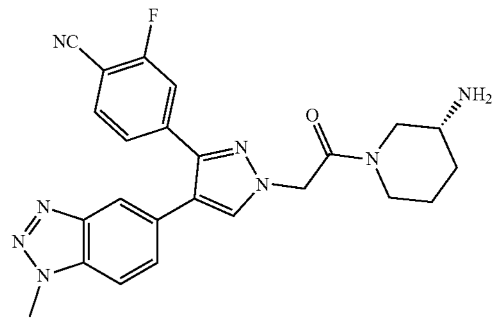

18

Synthetic Route:

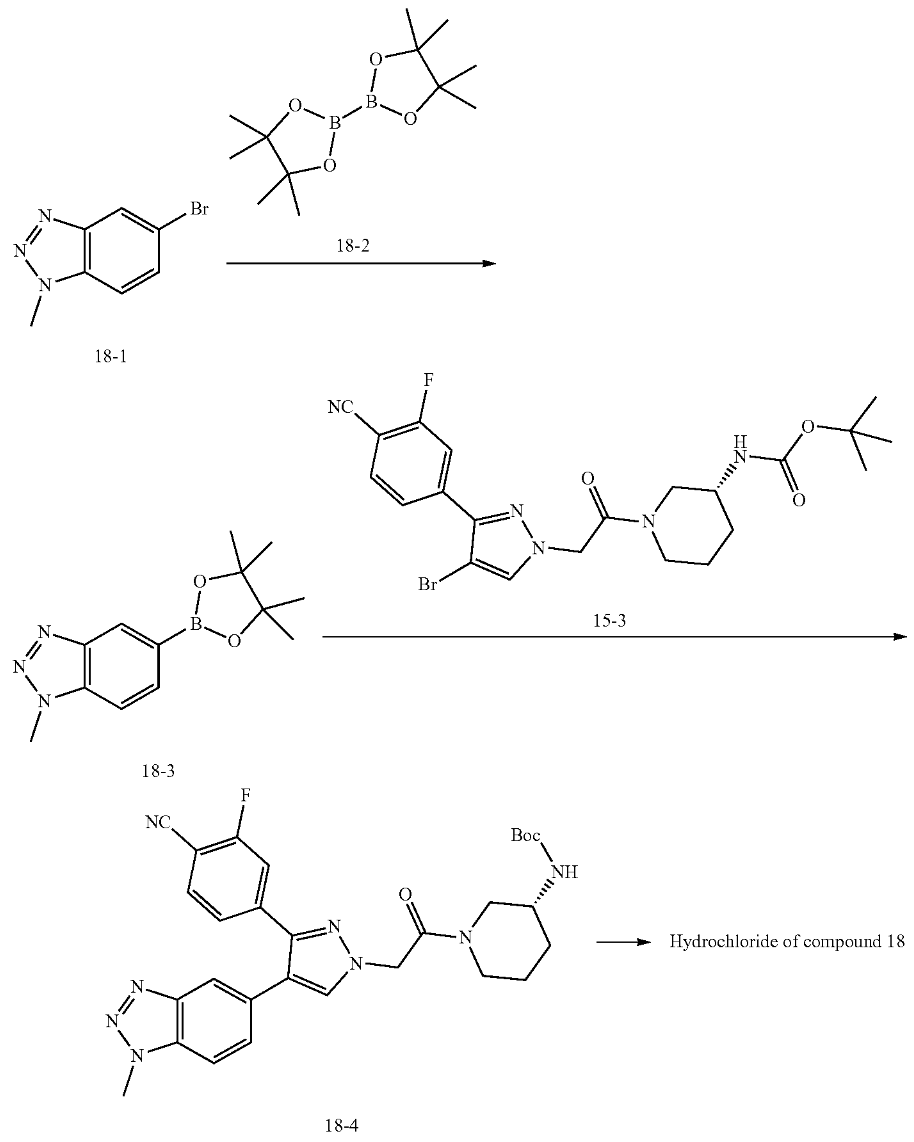

Step 1

Under the protection of nitrogen, compound 18-1 (200 mg, 943 μmol) was dissolved in 1,4-dioxane, then compound 18-2 (359 mg, 1.41 mmol), potassium phosphate (400 mg, 1.89 mmol) and [1,1'-bis(diphenylphosphino)ferrocene]dichloropalladium(II) (69.0 mg, 94.3 μmol) were added, and the reaction solution was stirred at 90° C. for 12 hours. The reaction solution was concentrated under reduced pressure, and the residue was separated and purified by silica gel column chromatography (1/1, petroleum ether/ethyl acetate, Rf=0.70) to obtain compound 18-3. $^1$H NMR (400 MHz, $CDCl_3$) 7.62-7.60 (m, 1H), 7.54-7.49 (m, 2H), 4.31 (s, 3H), 1.39 (s, 12H). MS-ESI calculated $[M+H]^+$260, found 260.

Step 2

Under the protection of nitrogen, compound 18-3 (80 mg, 309 μmol) was dissolved in 1,4-dioxane (5.00 mL) and water (1.00 mL), then compound 15-3 (156 mg, 308 μmol), potassium phosphate (131 mg, 617 μmol) and [1,1'-bis(diphenylphosphino)ferrocene]dichloropalladium(II) (45.2 mg, 61.8 μmol) were added, and the reaction solution was stirred at 90° C. for 12 hours. The reaction solution was concentrated under reduced pressure, and the residue was separated and purified by silica gel column chromatography (5/1, petroleum ether/ethyl acetate, Rf=0.35) to obtain compound 18-4. MS-ESI calculated $[M+H]^+$559, found 559.

Step 3

Compound 18-4 (50.0 mg, 262 μmol) was dissolved in ethyl acetate (5.00 mL), and a solution of hydrogen chloride in ethyl acetate (4 mol/L, 5.00 mL) was added. The reaction solution was stirred at 25° C. for 1 hour. The reaction solution was concentrated under reduced pressure, and the residue was separated and purified by preparative high performance liquid chromatography (Venusil ASB Phenyl 150*30 mm*5 μm; mobile phase A: 0.05% hydrochloric acid aqueous solution; mobile phase B: acetonitrile; B %: 30%-70%, 9 min) to obtain hydrochloride of compound 18. $^1$H NMR (400 MHz, $CD_3OD$) δ 7.96 (s, 1H), 7.91 (s, 1H), 7.79 (d, J=8.4 Hz, 1H), 7.65 (t, J=7.4 Hz, 1H), 7.50-7.35 (m, 3H), 5.36 (s, 2H), 4.37 (s, 3H), 4.21-4.09 (m, 1H), 3.79-3.76 (m, 1H), 3.48-3.35 (m, 3H), 2.17-1.79 (m, 4H). MS-ESI calculated $[M+H]^+$459, found 459.

Embodiment 19

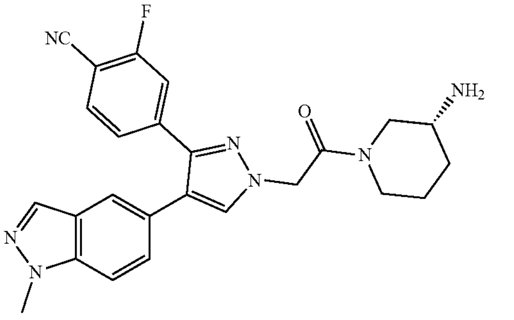

19

Synthetic Route:

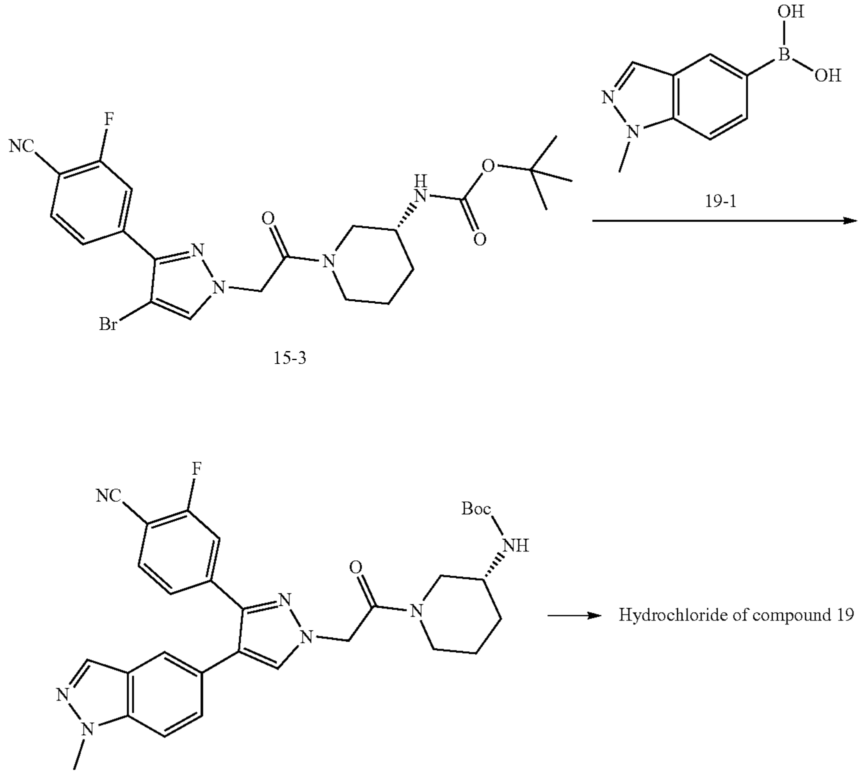

15-3

19-1

19-2

Step 1

Under the protection of nitrogen, compound 15-3 (100 mg, 197 μmol) was dissolved in 1,4-dioxane (10.0 mL) and water (2.00 mL), then compound 19-1 (41.7 mg, 237 μmol), potassium phosphate (83.8 mg, 395 μmol) and [1,1'-bis (diphenylphosphino)ferrocene]dichloropalladium(II) (28.9 mg, 39.5 μmol) were added, and the reaction solution was stirred at 90° C. for 12 hours. Water (50 mL) was added to the reaction solution, and the mixture was extracted with ethyl acetate (20 mL×3). The organic phase was washed with saturated brine (50 mL), dried over anhydrous sodium sulfate, filtered, concentrated under reduced pressure, and the residue was separated and purified by silica gel column chromatography (1/2, petroleum ether/ethyl acetate, Rf=0.14) to obtain compound 19-2. MS-ESI calculated $[M+H]^+$558, found 558.

Step 2

Compound 19-2 (60 mg, 108 μmol) was dissolved in ethyl acetate (5.00 mL), and a solution of hydrogen chloride in ethyl acetate (4 mol/L, 1.00 mL) was added. The reaction solution was stirred at 25° C. for 1 hour. The reaction solution was concentrated under reduced pressure, and the residue was separated and purified by preparative high performance liquid chromatography (Venusil ASB Phenyl 150*30 mm*5 uμm; mobile phase A: 0.05% hydrochloric acid aqueous solution; mobile phase B: acetonitrile; B %: 20%-50%, 9 min) to obtain hydrochloride of compound 19. $^1$H NMR (400 MHz, $CD_3OD$) δ=8.00 (s, 1H), 7.85 (s, 1H), 7.71 (s, 1H), 7.63 (t, J=7.2 Hz, 1H), 7.57 (d, J=8.8 Hz, 1H), 7.46-7.36 (m, 2H), 7.33 (d, J=8.8 Hz, 1H), 5.33 (s, 2H), 4.20-4.17 (m, 1H), 4.09 (s, 3H), 3.79-3.76 (m, 1H), 3.57-3.34 (m, 3H), 2.20-1.65 (m, 4H). MS-ESI calculated $[M+H]^+$458, found 458.

Embodiment 20

20

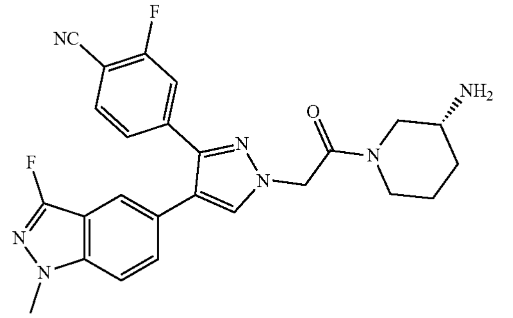

Synthetic Route:

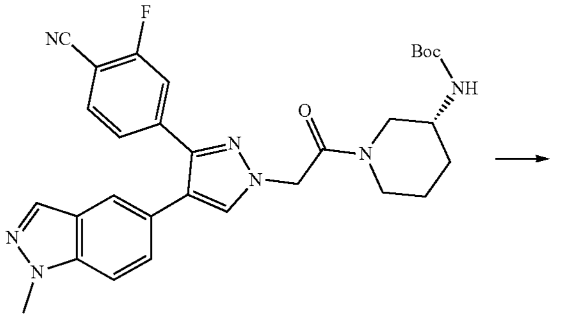

19-2

Hydrochloride of compound 20

Step 1

Compound 19-2 (100 mg, 179 μmol) was dissolved in acetonitrile (5.00 mL) and acetic acid (0.500 mL), and 1-chloromethyl-4-fluoro-1,4-diazoniabicyclo[2.2.2]octane bis(tetrafluoroborate) (127 mg, 359 μmol) was added. The reaction solution was stirred at 80° C. for 6 hours. The reaction solution was concentrated under reduced pressure, and the residue was separated and purified by preparative high performance liquid chromatography (Venusil ASB Phenyl 150*30 mm*5 μm; mobile phase A: 0.05% hydrochloric acid aqueous solution; mobile phase B: acetonitrile; B %: 35%-65%, 9 min) to obtain hydrochloride of compound 20. $^1$NMR (400 MHz, $CD_3OD$) δ 8.06 (s, 1H), 7.89 (s, 1H), 7.65-7.63 (t, J=7.2 Hz, 1H), 7.42 (d, J=8.8 Hz, 2H), 7.37-7.29 (m, 2H), 5.35 (s, 2H), 4.21-4.17 (m, 1H), 4.10 (s, 3H), 4.07-4.04 (m, 1H), 3.80-3.76 (m, 1H), 3.50-3.40 (m, 2H), 2.19-2.16 (m, 1H), 1.94-1.78 (m, 3H). MS-ESI calculated $[M-56+H]^+$476, found 476.

Embodiment 21

21

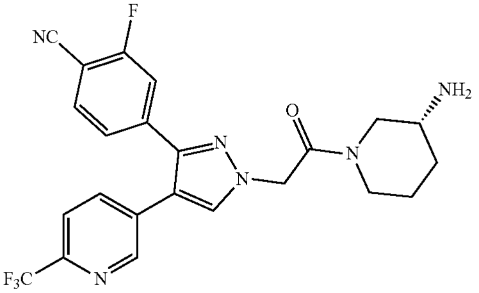

Synthetic Route:

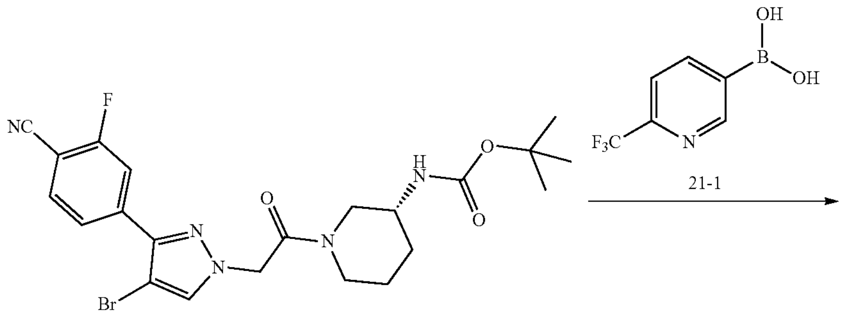

15-3

21-1

-continued

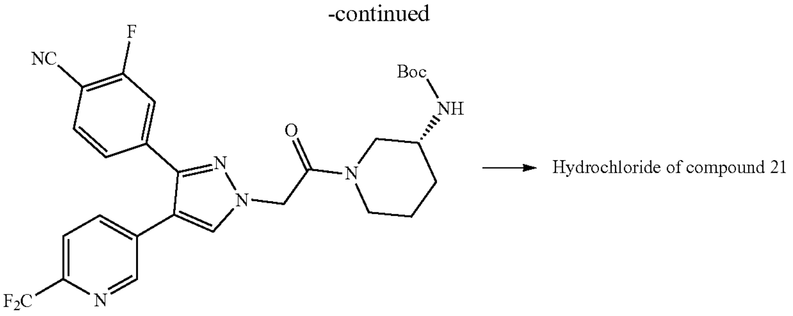

21-2

Step 1

Under the protection of nitrogen, compound 15-3 (100 mg, 197 μmol) was dissolved in 1,4-dioxane (10.0 mL) and water (2.00 mL), then compound 21-1 (45.2 mg, 237 μmol), potassium phosphate (83.8 mg, 395 μmol) and [1,1'-bis (diphenylphosphino)ferrocene]dichloropalladium(II) (28.9 mg, 39.5 μmol) were added, and the reaction solution was stirred at 90° C. for 12 hours. Water (50 mL) was added to the reaction solution, and the mixture was extracted with ethyl acetate (20 mL×3). The organic phase was washed with saturated brine (50 mL), dried over anhydrous sodium sulfate, filtered, concentrated under reduced pressure, and the residue was separated and purified by silica gel column chromatography (1/2, petroleum ether/ethyl acetate, Rf=0.14) to obtain compound 21-2. MS-ESI calculated $[M+Na]^+$595, found 595.

Step 2

Compound 21-2 (105 mg, 183 μmol) was dissolved in ethyl acetate (5.00 mL), then a solution of hydrogen chloride in ethyl acetate (4 mol/L, 500 μL) was added, and the reaction solution was stirred and reacted at 25° C. for 1 hour. The reaction solution was concentrated under reduced pressure, and the residue was separated and purified by preparative high performance liquid chromatography (Venusil ASB Phenyl 150*30 mm*5 μm; mobile phase A: 0.05% hydrochloric acid aqueous solution; mobile phase B: acetonitrile; B %: 24%-54%, 9 min) to obtain hydrochloride of compound 21. $^1H$ NMR (400 MHz, $CD_3OD$) δ=8.66 (s, 1H), 8.09 (s, 1H), 7.94 (d, J=8.0 Hz, 1H), 7.81 (d, J=8.0 Hz, 1H), 7.76-7.73 (m, 1H), 7.51-7.48 (m, 1H), 7.37 (dd, J=1.2, 8.0 Hz, 1H), 5.37 (s, 2H), 4.26-4.02 (m, 1H), 3.79-3.75 (m, 1H), 3.56-3.34 (m, 3H), 2.25-2.10 (m, 1H), 2.01-1.92 (m, 1H), 1.86-1.70 (m, 2H). MS-ESI calculated $[M+H]^+$473, found 473.

Embodiment 22

22

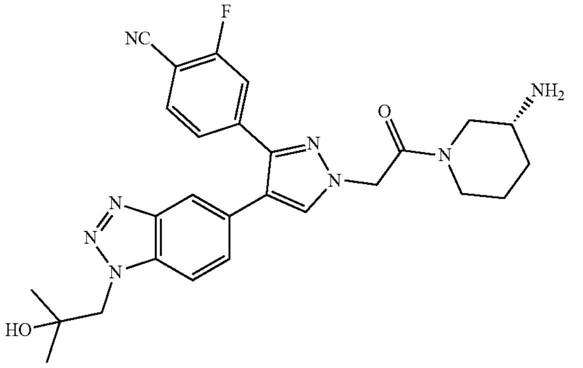

Synthetic Route:

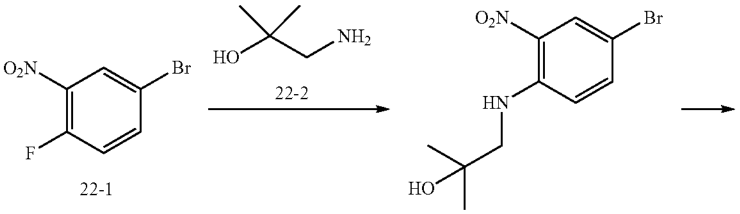

22-1

22-3

-continued

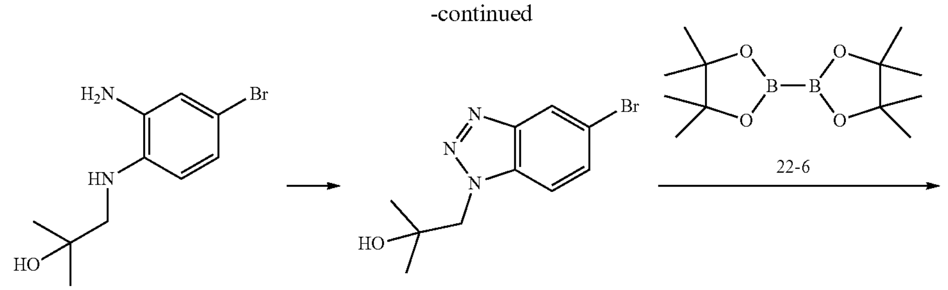

22-4 22-5

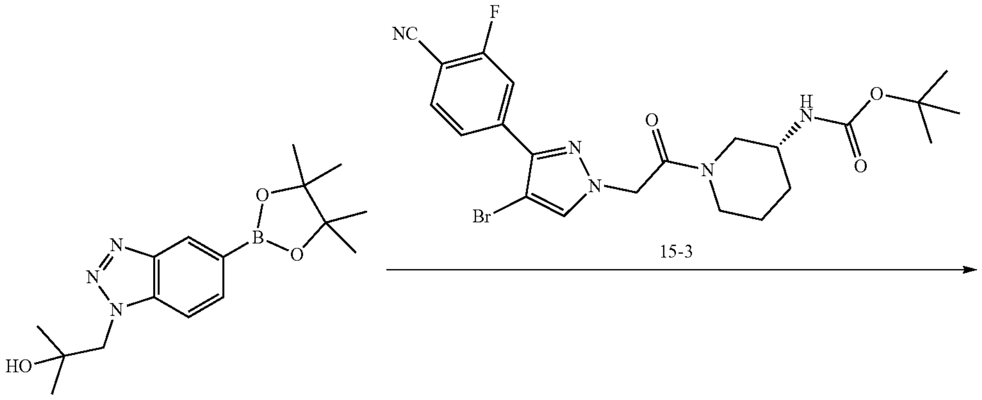

22-7

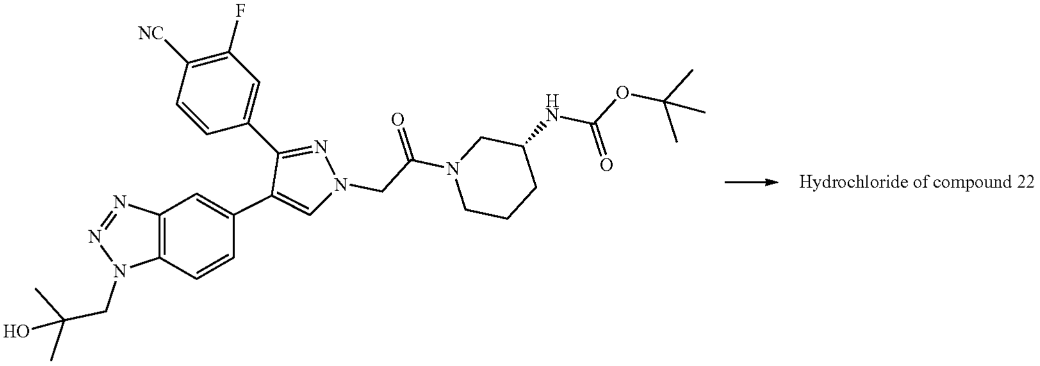

22-8

Step 1

Compound 22-1 (20.0 g, 90.9 mmol) was dissolved in N,N-dimethylformamide (5.00 mL), then compound 22-2 (9.72 g, 109 mmol) and N, N-diisopropyl ethyl amine (23.5 g, 182 mmol) were added, and the reaction solution was stirred at 80° C. for 12 hours. Water (50 mL) was added to the reaction solution, and the mixture was extracted with ethyl acetate (20 mL×3). The organic phase was washed with saturated brine (50 mL), dried over anhydrous sodium sulfate, filtered, concentrated under reduced pressure, and the residue was separated and purified by silica gel column chromatography (3/1, petroleum ether/ethyl acetate, Rf=0.37) to obtain compound 22-3. $^1$H NMR (400 MHz, $CDCl_3$) δ=8.36 (s, 1H), 8.33 (d, J=2.4 Hz, 1H), 7.49 (dd, J=2.4, 9.2 Hz, 1H), 6.85 (d, J=9.2 Hz, 1H), 3.30 (d, J=5.6 Hz, 2H), 1.38 (s, 6H). MS-ESI calculated $[M+H]^+$291, found 291.

Step 2

Compound 22-3 (19.0 g, 65.7 mmol) was dissolved in ethanol (5.00 mL), then tin (II) dichloride (59.3 g, 263 mmol) was added, and the reaction solution was stirred and reacted at 80° C. for 3 hours. The reaction solution was concentrated under reduced pressure, and the residue was separated and purified by silica gel column chromatography (3/1, petroleum ether/ethyl acetate, Rf=0.12) to obtain compound 22-4. $^1$H NMR (400 MHz, DMSO-$d_6$) δ=6.70 (d, J=2.4 Hz, 1H), 6.59 (dd, J=2.4, 8.4 Hz, 1H), 6.36 (d, J=8.4 Hz, 1H), 4.88 (, 2H), 4.47 (s, 1H), 3.17 (s, 2H), 1.18 (s, 6H). MS-ESI calculated $[M+Na]^+$261, found 261.

Step 3

Compound 22-4 (11.0 g, 42.5 mmol) was dissolved in water (50.0 mL), then concentrated sulfuric acid (14.2 mL) and sodium nitrite (4.39 g, 63.7 mmol) were added, and the reaction solution was stirred and reacted at 0° C. for 2 hours.

Water (30 mL) was added to the reaction solution, and the mixture was extracted with ethyl acetate (30 mL×2). The organic phase was washed with saturated brine (30 mL), dried over anhydrous sodium sulfate, filtered, concentrated under reduced pressure, and the residue was separated and purified by silica gel column chromatography (1/1, petroleum ether/ethyl acetate, Rf=0.30) to obtain compound 22-5. MS-ESI calculated $[M+H]^+$272, found 272.

Step 4

Under the protection of nitrogen, compound 22-5 (2.40 g, 4.98 mmol) was dissolved in 1,4-dioxane (20.0 mL), then compound 22-6 (1.90 g, 7.46 mmol), potassium phosphate (2.11 g, 9.95 mmol) and [1,1'-bis(diphenylphosphino)ferrocene]dichloropalladium(II) (364 mg, 497 μmol) were added, and the reaction solution was stirred at 100° C. for 12 hours. Water (50 mL) was added to the reaction solution, and the mixture was extracted with ethyl acetate (20 mL×3). The organic phase was washed with saturated brine (50 mL), dried over anhydrous sodium sulfate, filtered, concentrated under reduced pressure, and the residue was separated and purified by silica gel column chromatography (1/1, petroleum ether/ethyl acetate, Rf=0.50) to obtain compound 22-7. MS-ESI calculated $[M+H]^+$318, found 318.

Step 5

Under the protection of nitrogen, compound 22-7 (100 mg, 197 μmol) was dissolved in 1,4-dioxane (4.00 mL) and water (1.00 mL), then compound 15-3 (47.6 mg, 150 μmol), potassium phosphate (63.7 mg, 300 μmol) and [1,1'-bis(diphenylphosphino)ferrocene]dichloropalladium(II) (22.0 mg, 30.0 μmol) were added, and the reaction solution was stirred at 90° C. for 12 hours. Water (30 mL) was added to the reaction solution, and the mixture was extracted with ethyl acetate (10 mL×3). The organic phase was washed with saturated brine (50 mL), dried over anhydrous sodium sulfate, filtered, concentrated under reduced pressure to obtain compound 22-8. MS-ESI calculated $[M+H]^+$618, found 618.

Step 6

Compound 22-8 (90 mg, 146 μmol) was dissolved in ethyl acetate (10.0 mL), and a solution of hydrogen chloride in ethyl acetate (4 mol/L, 400 μL) was added. The reaction solution was stirred at 25° C. for 1 hour. The reaction solution was concentrated under reduced pressure, and the residue was separated and purified by preparative high performance liquid chromatography (Venusil ASB Phenyl 150*30 mm*5 μm; mobile phase A: 0.05% hydrochloric acid aqueous solution; mobile phase B: acetonitrile; B %: 15%-45%, 9 min) to obtain hydrochloride of compound 22. $^1H$ NMR (400 MHz, $CD_3OD$) δ=7.96 (s, 1H), 7.91-7.83 (m, 2H), 7.65 (t, J=7.6 Hz, 1H), 7.49-7.35 (m, 3H), 5.36 (s, 2H), 4.70 (s, 2H), 4.22-4.02 (m, 1H), 3.78-3.74 (m, 1H), 3.58-3.35 (m, 3H), 2.20-2.10 (m, 1H), 1.98-1.70 (m, 3H), 1.29 (s, 6H). MS-ESI calculated $[M+H]^+$517, found 517.

Embodiment 23

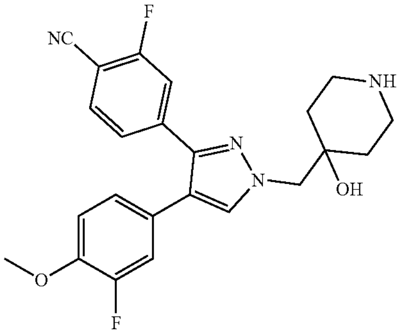

23

Synthetic Route:

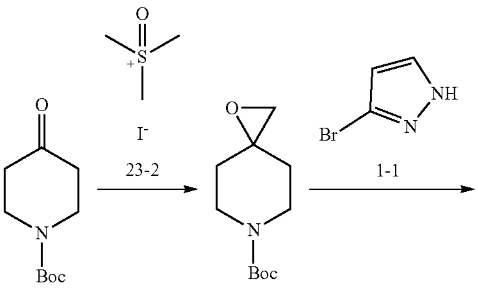

23-1

23-3

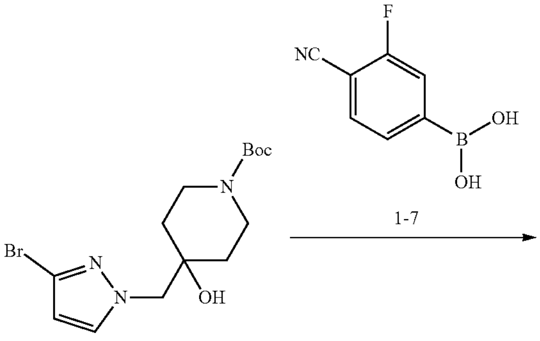

23-4

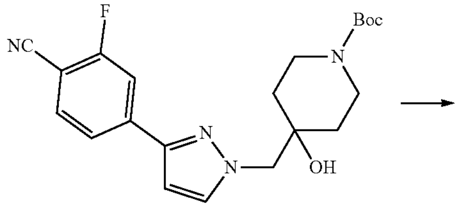

23-5

-continued

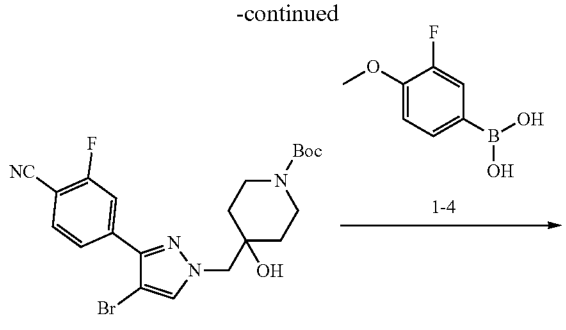

23-6

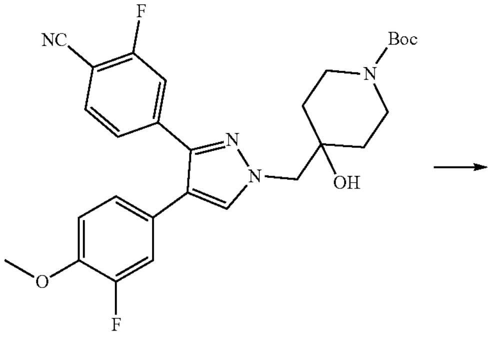

23-7

Hydrochloride of compound 23

Step 1

Compound 23-1 (2.43 g, 11.0 mmol) and sodium hydride (442 mg, 11.0 mmol, 60% purity) were dissolved in dimethyl sulfoxide (10.0 mL), and a solution of compound 23-2 (2.00 g, 10.0 mmol) in dimethyl sulfoxide (10.0 mL) was added dropwise to the reaction solution. The reaction solution was stirred at 55° C. for 6 hours under the protection of nitrogen. Ice water (50 mL) was added to the reaction solution, and the mixture was extracted with ethyl acetate (100 mL×2). The organic phase was washed with saturated brine (100 mL), dried over anhydrous sodium sulfate, filtered, concentrated under reduced pressure, and the residue was separated and purified by silica gel column chromatography (3/1, petroleum ether/ethyl acetate, Rf=0.48) to obtain compound 23-3. $^1$H NMR (400 MHz, $CDCl_3$) δ=3.76-3.73 (m, 2H), 3.48-3.42 (m, 2H), 2.71 (s, 2H), 1.85-1.78 (m, 2H), 1.50 (s, 9H), 1.48-1.44 (m, 2H). MS-ESI calculated $[M-56+H]^+$158, found 158.

Step 2

Under the protection of nitrogen, compound 23-3 (300 mg, 2.04 mmol) was dissolved in N,N-dimethylformamide (6.00 mL), then sodium hydride (122 mg, 3.06 mmol, 60% purity) and compound 1-1 (435 mg, 2.04 mmol) were added, and the reaction solution was stirred at 90° C. for 3 hours. The reaction solution was quenched with saturated sodium bicarbonate aqueous solution (50.0 mL), and extracted with ethyl acetate (50 mL×2). The organic phase was washed with saturated brine (100 mL), dried over anhydrous sodium sulfate, filtered, concentrated under reduced pressure, and the residue was separated and purified by thin layer chromatography (1/2, petroleum ether/ethyl acetate, Rf=0.5) to obtain compound 23-4. $^1$H NMR (400 MHz, $CDCl_3$) δ 7.23 (d, J=2.4 Hz, 1H), 6.23 (d, J=2.4 Hz, 1H), 3.97 (s, 2H), 3.87-3.78 (m, 2H), 3.37 (s, 1H), 3.11-3.05 (m, 2H), 1.44-1.41 (m, 1H), 1.38 (s, 9H), 1.36-1.29 (m, 3H). MS-ESI calculated $[M-100+H]^+$260, found 260.

Step 3

Compound 23-4 (270 mg, 749 μmol), compound 1-7 (130 mg, 787 μmol) and potassium phosphate (320 mg, 1.51 mmol) were dissolved in 1,4-dioxane (5.00 mL) and water (0.500 mL), then [1,1'-bis(diphenylphosphino)ferrocene]dichloropalladium(II) (48.9 mg, 75.0 μmol) was added to the reaction solution under the protection of nitrogen, and the reaction solution was stirred at 90° C. for 12 hours. The reaction solution was filtered, the filtrate was concentrated under reduced pressure, and the residue was separated and purified by thin layer chromatography (1/2, petroleum ether/ethyl acetate, Rf=0.50) to obtain compound 23-5. MS-ESI calculated $[M-56+H]^+$345, found 345.

Step 4

Compound 23-5 (320 mg, 799 μmol) and N-bromosuccinimide (160 mg, 899 mmol) were dissolved in acetonitrile (10.0 mL). The reaction solution was stirred at 25° C. for 12 hours. The reaction solution was concentrated under reduced pressure, and the residue was separated and purified by thin layer chromatography (1/1, petroleum ether/ethyl acetate, Rf=0.38) to obtain compound 23-6. $^1$H NMR (400 MHz, $CDCl_3$) δ=7.92-7.85 (m, 2H), 7.71-7.69 (m, 1H), 7.60 (s, 1H), 4.13 (s, 2H), 3.90-3.81 (m, 2H), 3.26 (s, 1H), 3.21-3.15 (m, 2H), 1.59-1.51 (m, 3H), 1.47 (s, 9H), 1.45-1.43 (m, 1H). MS-ESI calculated $[M-56+H]^+$423, found 423.

Step 5

Compound 23-6 (320 mg, 668 μmol), compound 1-4 (119 mg, 701 μmol) and potassium phosphate (283 mg, 1.34 mmol) were dissolved in 1,4-dioxane (10.0 mL) and water (1.00 mL), and [1,1'-bis(diphenylphosphino)ferrocene]dichloropalladium(II) (43.5 mg, 66.8 μmol) was added to the reaction solution under the protection of nitrogen. The reaction solution was stirred at 90° C. for 12 hours. The reaction solution was filtered, the filtrate was concentrated under reduced pressure, and the residue was separated and purified by thin layer chromatography (1/1, petroleum ether/ethyl acetate, Rf=0.20) to obtain compound 23-7. MS-ESI calculated $[M-56+H]^+$469, found 469.

Step 6

Compound 23-7 (371 mg, 695 μmol) was dissolved in ethyl acetate (5.00 mL), and a solution of hydrogen chloride in ethyl acetate (4 mol/L, 5.00 mL) was added. The reaction solution was stirred at 25° C. for 2 hours. The reaction solution was concentrated under reduced pressure, and the residue was separated and purified by preparative high performance liquid chromatography (3_Phenomenex Luna C18 75×30 mm×3 μm; mobile phase A: 0.05% hydrochloric acid aqueous solution; mobile phase B: acetonitrile; B %: 20%-40%, 7.5 min) to obtain hydrochloride of compound 23. $^1$H NMR (400 MHz, $CD_3OD$) δ 7.85 (s, 1H), 7.72-7.68 (m, 1H), 7.49-7.42 (m, 2H), 7.14-7.09 (m, 1H), 7.06-7.02 (m, 2H), 4.31 (s, 2H), 3.91 (s, 3H), 3.32-3.27 (m, 4H), 2.02-1.94 (m, 2H), 1.84-1.80 (m, 2H). MS-ESI calculated $[M+H]^+$425, found 425.

Embodiment 24

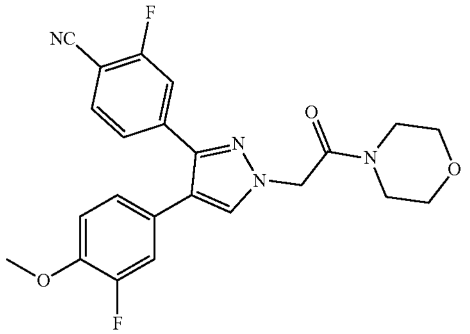

24

Synthetic Route:

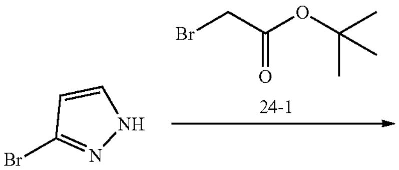

24-1

1-1

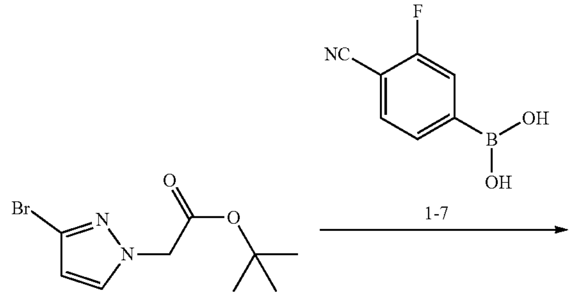

1-7

24-2

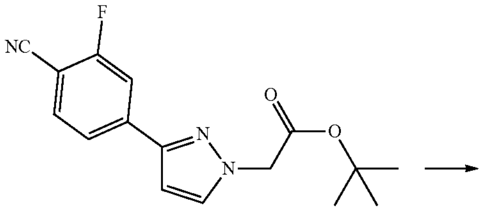

24-3

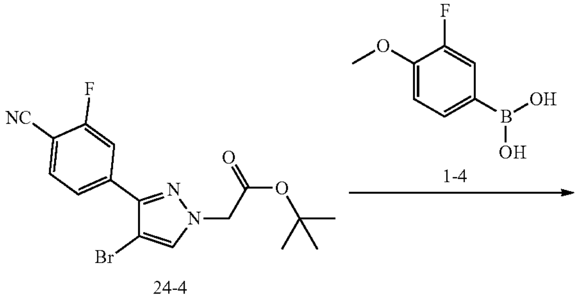

1-4

24-4

-continued

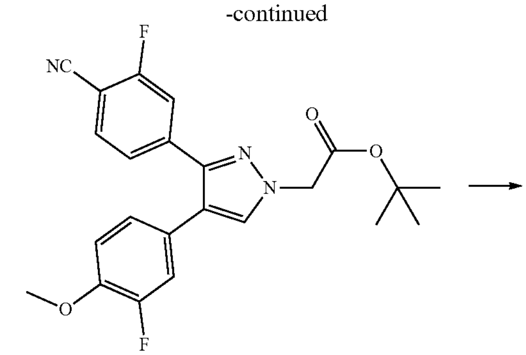

24-5

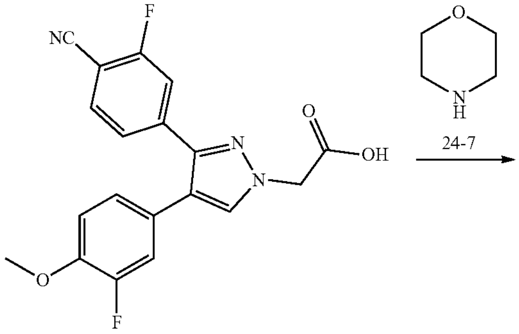

24-7

24-6

Hydrochloride of compound 24

Step 1

Compound 1-1 (3.00 g, 20.4 mmol) was dissolved in acetonitrile (50.0 mL), compound 24-1 (5.97 g, 30.6 mmol) and potassium carbonate (5.64 g, 40.8 mmol) were added, and the reaction solution was stirred at 50° C. for 12 hours under the protection of nitrogen. The reaction solution was filtered, and the filter residue was washed with ethyl acetate (100 mL), the filtrate was concentrated under reduced pressure, and the residue was separated and purified by silica gel column chromatography (5/1, petroleum ether/ethyl acetate, Rf=0.40) to obtain compound 24-2. $^1$H NMR (400 MHz, $CDCl_3$) δ=7.30 (d, J=2.4 Hz, 1H), 6.26 (d, J=2.4 Hz, 1H), 4.70 (s, 2H), 1.40 (s, 9H). MS-ESI calculated $[M-56+H]^+$ 205, found 205.

Step 2

Under the protection of nitrogen, compound 24-2 (2.93 g, 11.2 mmol), compound 1-7 (1.94 g, 11.8 mmol) and potassium phosphate (4.80 g, 22.6 mmol) were dissolved in 1,4-dioxane (30.0 mL) and water (3.00 mL), then dichloro [1,1'-bis(di-tert-butylphosphino)ferrocene]palladium(II) (733 mg, 1.12 mmol) was added, and the reaction solution was stirred at 90° C. for 12 hours. The reaction solution was filtered, the filtrate was concentrated under reduced pressure, and the residue was separated and purifiedby silica gel column chromatography (3/1, petroleum ether/ethyl acetate, Rf=0.43) to obtain compound 24-3. $^1$H NMR (400 MHz, $CDCl_3$) δ=7.61-7.53 (m, 3H), 7.47 (d, J=2.4 Hz, 1H), 6.60 (d, J=2.4 Hz, 1H), 4.79 (s, 2H), 1.42 (s, 9H). MS-ESI calculated $[M-56+H]^+$246, found 246.

Step 3

Compound 24-3 (3.10 g, 10.3 mmol) and N-bromosuccinimide (1.92 g, 10.8 mmol) were dissolved in acetonitrile (35.0 mL). The reaction solution was stirred at 25° C. for 12 hours. Ethyl acetate (150 mL) was added to the reaction solution, and the mixture was washed with water (100 mL×1) and saturated brine (100 mL×1) successively. The organic phase was dried over anhydrous sodium sulfate, and filtered. The filtrate was concentrated under reduced pressure, and the residue was separated and purified by silica gel column chromatography (3/1, petroleum ether/ethyl acetate, Rf=0.50) to obtain compound 24-4. $^1$H NMR (400 MHz, $CDCl_3$) δ=7.83-7.77 (m, 2H), 7.60-7.56 (m, 2H), 4.76 (s, 2H), 1.43 (s, 9H). MS-ESI calculated [M−56+H]$^+$324, found 324.

Step 4

Under the protection of nitrogen, compound 24-4 (3.72 g, 9.78 mmol), compound 1-4 (1.75 g, 10.3 mmol) and potassium phosphate (4.15 g, 19.6 mmol) were dissolved in 1,4-dioxane (50.0 mL) and water (5.00 mL), then dichloro [1,1'-bis(di-tert-butylphosphino)ferrocene]palladium(II) (638 mg, 978 μmol) was added, and the reaction solution was stirred at 90° C. for 12 hours. The reaction solution was filtered, the filtrate was concentrated under reduced pressure, and the residue was separated and purified by silica gel column chromatography (3/1, petroleum ether/ethyl acetate, Rf=0.25) to obtain compound 24-5. $^1$H NMR (400 MHz, $CDCl_3$) δ=7.47-7.43 (m, 2H), 7.36-7.29 (m, 2H), 6.95-6.84 (m, 3H), 4.80 (s, 2H), 3.85 (s, 3H), 1.44 (s, 9H). MS-ESI calculated [M+H]$^+$426, found 426.

Step 5

Compound 24-5 (200 mg, 470 mol) was dissolved in anhydrous dichloromethane (5.00 mL), then trifluoroacetic acid (0.500 mL) was added, and the reaction solution was stirred at 25° C. for 16 hours. The reaction solution was concentrated under reduced pressure to obtain compound 24-6. MS-ESI calculated [M+H]$^+$370, found 370.

Step 6

Compound 24-6 (174 mg, 471 μmol) was dissolved in anhydrous N,N-dimethylformamide (6.00 mL), then O-(7-azabenzotriazol-1-yl)-N,N,N,N-tetramethyluronium hexafluorophosphate (269 mg, 707 μmol) and N,N-diisopropylethylamine (122 mg, 942 μmol) were added, and the reaction solution was stirred at 25° C. for 0.5 hours. Compound 24-7 (50.0 mg, 574 μmol) was added, and the reaction solution was stirred at 25° C. for 12 hours. Ethyl acetate (50.0 mL) was added to the reaction solution, and then the mixture was washed with water (50.0 mL×3) and saturated brine (50.0 mL×1). The organic phase was dried over anhydrous sodium sulfate, filtered, the filtrate was concentrated under reduced pressure, and the residue was separated and purified by preparative high performance liquid chromatography (3_Phenomenex Luna C18 75×30 mm×3 μm; mobile phase A: 0.05% hydrochloric acid aqueous solution; mobile phase B: acetonitrile; B %: 42%-62%, 7 min) to obtain hydrochloride of compound 24. $^1$H NMR (400 MHz, $CD_3OD$) δ=7.79 (s, 1H), 7.72-7.68 (m, 1H), 7.47-7.42 (m, 2H), 7.14-7.03 (m, 3H), 5.27 (s, 2H), 3.91 (s, 3H), 3.78-3.76 (m, 2H), 3.73-3.71 (m, 2H), 3.67-3.64 (m, 4H). MS-ESI calculated [M+H]$^+$439, found 439.

Embodiment 25

25

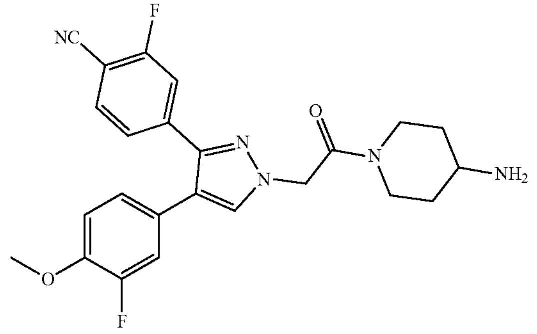

Synthetic Route:

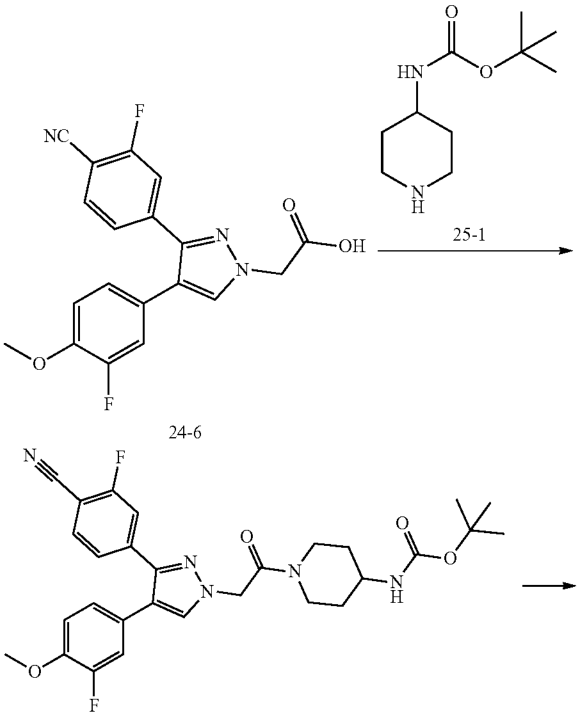

24-6

25-2

Hydrochloride of compound 25

Step 1

Compound 24-6 (200 mg, 541 μmol) was dissolved in anhydrous N,N-dimethylformamide (6.00 mL), then compound 25-1 (119 mg, 595 mol), 0-(7-azabenzotriazol-1-yl)-N,N,N,N-tetramethyluronium hexafluorophosphate (309 mg, 812 μmol) and N,N-diisopropylethylamine (280 mg, 2.17 mmol) were added; and the reaction solution was stirred at 25° C. for 12 hours. Water (50.0 mL) was added to the reaction solution, the resulting suspension was filtered, and the collected filter cake was washed with water (30.0 mL) and dried under vacuum to obtain compound 25-2. MS-ESI calculated $[M+H]^+$552, found 552.

Step 2

Compound 25-2 (290 mg, 525 μmol) was dissolved in ethyl acetate (5.00 mL), and a solution of hydrogen chloride in ethyl acetate (4 mol/L, 5.00 mL) was added. The reaction solution was stirred at 25° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 22%-42%, 7 min) to obtain hydrochloride of compound 25. $^1$NMR (400 MHz, $CD_3OD$) δ=7.80 (s, 1H), 7.72-7.68 (m, 1H), 7.48-7.42 (m, 2H), 7.14-7.02 (m, 3H), 5.37-5.24 (m, 2H), 4.64-4.60 (m, 1H), 4.19-4.16 (m, 1H), 3.91 (s, 3H), 3.50-3.43 (m, 1H), 3.35-3.33 (m, 1H), 2.88-2.82 (m, 1H), 2.18-2.08 (m, 2H), 1.75-1.66 (m, 1H), 1.59-1.50 (m, 1H). MS-ESI calculated $[M+H]^+$452, found 452.

Embodiment 26

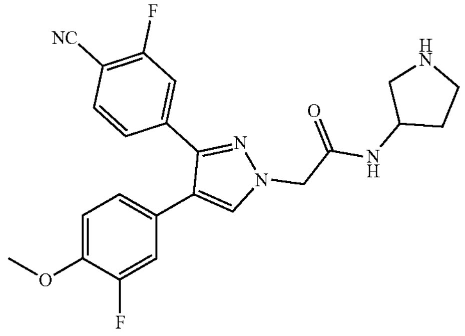

26

Synthetic Route:

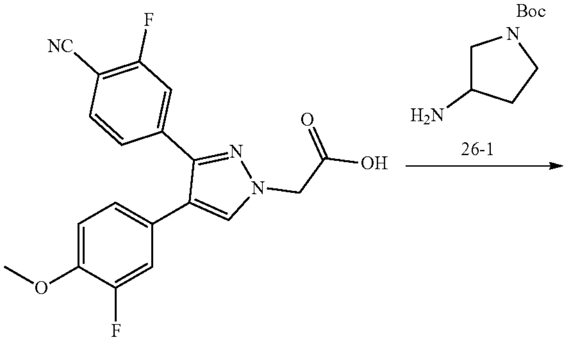

24-6

-continued

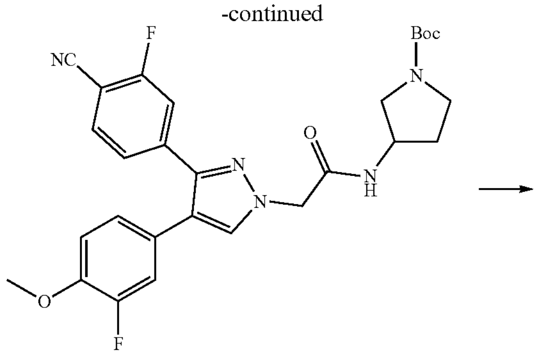

26-2

Hydrochloride of compound 26

Step 1

Compound 24-6 (240 mg, 650 μmol) was dissolved in anhydrous N,N-dimethylformamide (6.00 mL), then compound 26-1 (133 mg, 715 μmol), 0-(7-azabenzotriazol-1-yl)-N,N,N,N-tetramethyluronium hexafluorophosphate (371 mg, 975 μmol) and N,N-diisopropylethylamine (336 mg, 2.60 mmol) were added. The reaction solution was stirred at 25° C. for 12 hours. Water (100 mL) was added to precipitate a solid, filtered, and the filter cake was washed with water (50.0 mL) and dried under vacuum to obtain compound 26-2. MS-ESI calculated $[M+Na]^+$560, found 560.

Step 2

Compound 26-2 (320 mg, 595 μmol) was dissolved in ethyl acetate (5 mL), and a solution of hydrogen chloride in ethyl acetate (4 mol/L, 5.00 mL) was added. The reaction solution was stirred at 25° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 21%-41%, 7 min) to obtain hydrochloride of compound 26. $^1$H NMR (400 MHz, $CD_3OD$) δ=7.86 (s, 1H), 7.72-7.69 (m, 1H), 7.47-7.41 (m, 2H), 7.14-7.02 (m, 3H), 5.00 (d, J=1.6 Hz, 2H), 4.50-4.44 (m, 1H), 3.91 (s, 3H), 3.58-3.49 (m, 2H), 3.43-3.38 (m, 1H), 3.36-3.34 (m, 1H), 2.43-2.34 (m, 1H), 2.17-2.08 (m, 1H). MS-ESI calculated $[M+H]^+$438, found 438.

Embodiment 27

27

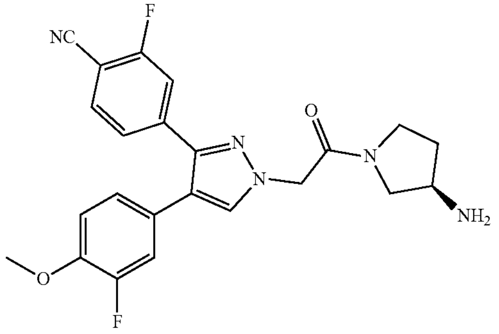

Synthetic Route:

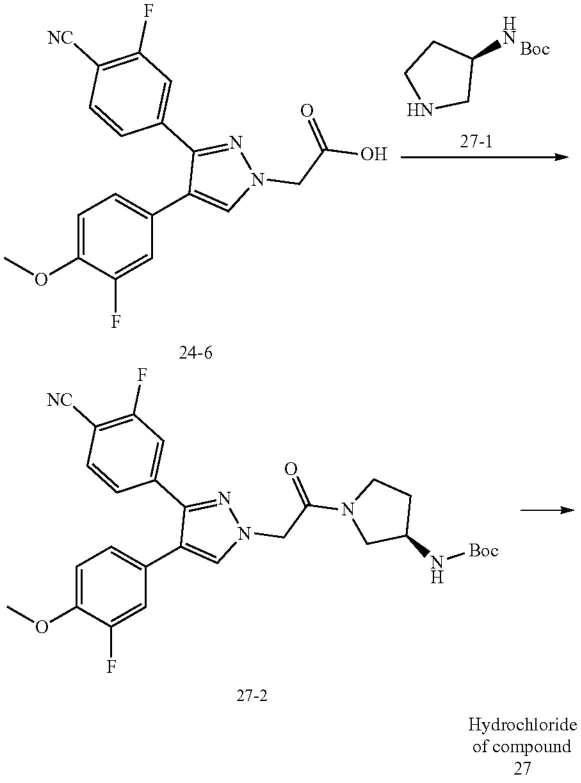

24-6

27-2

Hydrochloride of compound 27

Step 1

Compound 24-6 (200 mg, 541 μmol) was dissolved in N,N-dimethylformamide (5.00 mL), then compound 27-1 (111 mg, 595 μmol), 0-(7-azabenzotriazol-1-yl)-N,N,N,N-tetramethyluronium hexafluorophosphate (309 mg, 812 μmol) and N,N-diisopropylethylamine (280 mg, 2.17 mmol) were added, and the reaction solution was stirred at 25° C. for 12 hours. Water (50.0 mL) was added to the reaction solution, filtered, and the filter cake was washed with water (30.0 mL) and dried under vacuum to obtain compound 27-2. MS-ESI calculated $[M+H]^+$538, found 538.

Step 2

Compound 27-2 (340 mg, 632 μmol) was dissolved in ethyl acetate (5.00 mL), then a solution of hydrogen chloride in ethyl acetate (4 mol/L, 5.00 mL) was added, and the reaction solution was stirred and reacted at 25° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 20%-40%, 7 min) to obtain hydrochloride of compound 27. $^1$H NMR (400 MHz, $CD_3OD$) δ=7.82 (d, J=2.0 Hz, 1H), 7.73-7.69 (m, 1H), 7.48-7.41 (m, 2H), 7.14-7.02 (m, 3H), 5.20-5.18 (m, 2H), 4.09-3.97 (m, 1H), 3.91 (s, 3H), 3.88-3.81 (m, 2H), 3.75-3.64 (m, 2H), 2.59-2.39 (m, 1H), 2.29-2.07 (m, 1H). MS-ESI calculated $[M+H]^+$438, found 438.

Embodiment 28

28

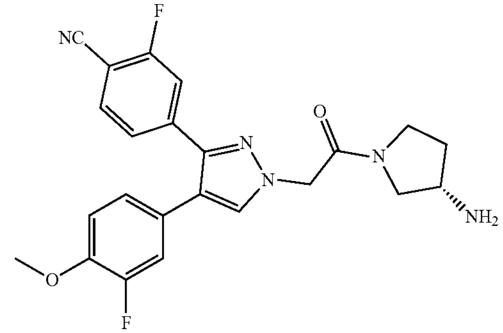

Synthetic Route:

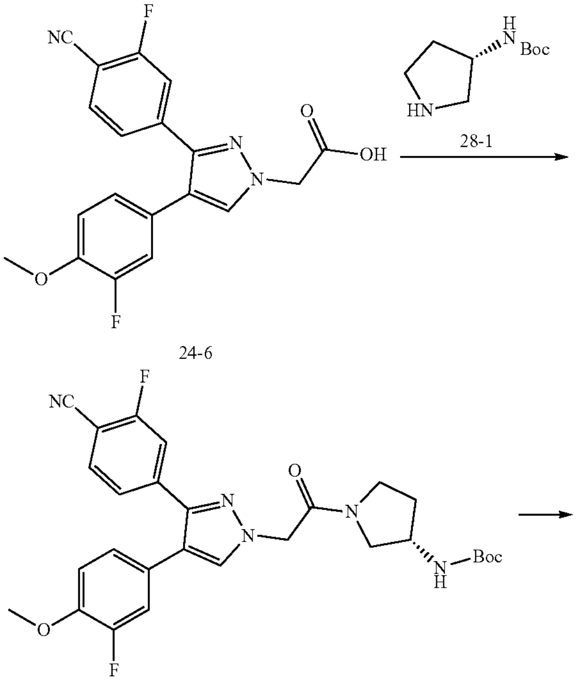

24-6

28-2

Hydrochloride of compound 28

Step 1

Compound 24-6 (200 mg, 541 μmol) was dissolved in N,N-dimethylformamide (5.00 mL), compound 28-1 (111 mg, 595 μmol), then O-(7-azabenzotriazol-1-yl)-N,N,N,N-tetramethyluronium hexafluorophosphate (309 mg, 812 μmol) and N,N-diisopropylethylamine (280 mg, 2.17 mmol) were added, and the reaction solution was stirred at 25° C. for 12 hours. Water (50.0 mL) was added to the reaction solution, filtered, and the filter cake was washed with water (30.0 mL) and dried under vacuum to obtain compound 28-2. MS-ESI calculated $[M+H]^+$538, found 538.

Step 2

Compound 28-2 (320 mg, 595 μmol) was dissolved in ethyl acetate (5.00 mL), then a solution of hydrogen chloride in ethyl acetate (4 mol/L, 5.00 mL) was added, and the reaction solution was stirred and reacted at 25° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 19%-39%, 7 min) to obtain hydrochloride of compound 28. $^1H$ NMR (400 MHz, $CD_3OD$) δ=7.83 (d, J=1.2 Hz, 1H), 7.72-7.68 (m, 1H), 7.47-7.41 (m, 2H), 7.14-7.02 (m, 3H), 5.21-5.19 (m, 2H), 4.09-3.99 (m, 1H), 3.91 (s, 3H), 3.90-3.82 (m, 2H), 3.77-3.65 (m, 2H), 2.59-2.37 (m, 1H), 2.30-2.05 (m, 1H). MS-ESI calculated $[M+H]^+$438, found 438.

Embodiment 29

29

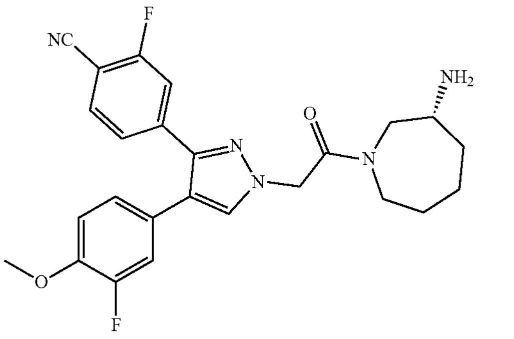

Synthetic Route:

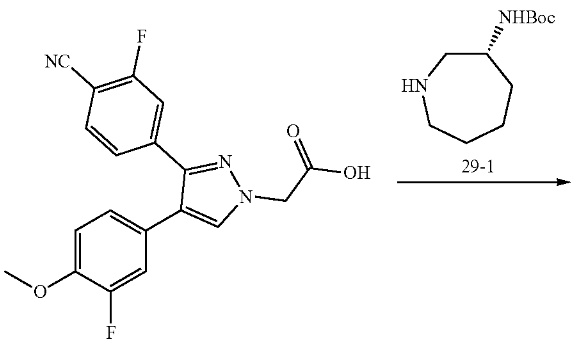

24-6

-continued

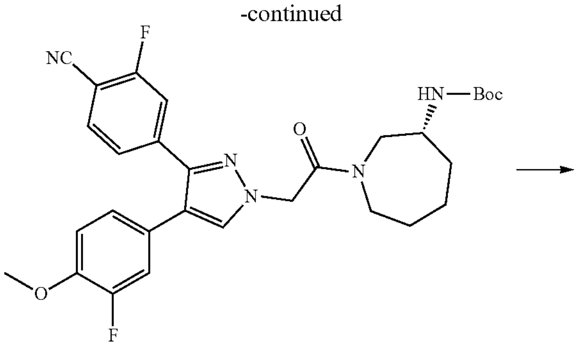

29-2

Hydrochloride of compound 29

Step 1

Compound 24-6 (200 mg, 541 μmol) was dissolved in anhydrous N,N-dimethylformamide (5.00 mL), then compound 29-1 (128 mg, 597 μmol), 0-(7-azabenzotriazol-1-yl)-N,N,N,N-tetramethyluronium hexafluorophosphate (309 mg, 812 μmol) and N,N-diisopropylethylamine (280 mg, 2.17 mmol) were added. The reaction solution was stirred at 25° C. for 12 hours. Water (50.0 mL) was added to the reaction solution, filtered, and the filter cake was washed with water (30.0 mL) and dried under vacuum to obtain compound 29-2. MS-ESI calculated $[M+H]^+$566, found 566.

Step 2

Compound 29-2 (350 mg, 619 μmol) was dissolved in ethyl acetate (5.00 mL), and a solution of hydrogen chloride in ethyl acetate (4 mol/L, 5.00 mL) was added. The reaction solution was stirred at 25° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 21%-41%, 7 min) to obtain hydrochloride of compound 29. $^1H$ NMR (400 MHz, CD3OD) δ=7.87 (s, 1H), 7.73-7.70 (m, 1H), 7.47-7.42 (m, 2H), 7.14-7.02 (m, 3H), 5.40-5.29 (m, 2H), 4.02-3.97 (m, 1H), 3.91 (s, 3H), 3.89-3.85 (m, 1H), 3.75-3.70 (m, 1H), 3.54-3.46 (m, 2H), 2.21-2.15 (m, 1H), 2.01-1.82 (m, 3H), 1.70-1.60 (m, 2H). MS-ESI calculated $[M+H]^+$466, found 466.

Embodiment 30

30

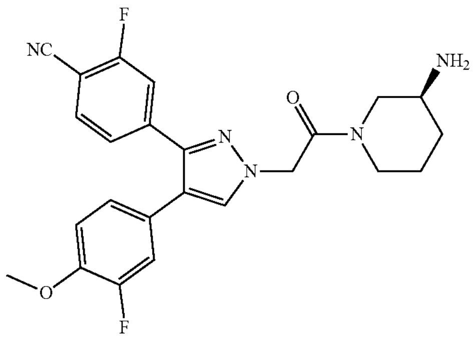

Synthetic Route:

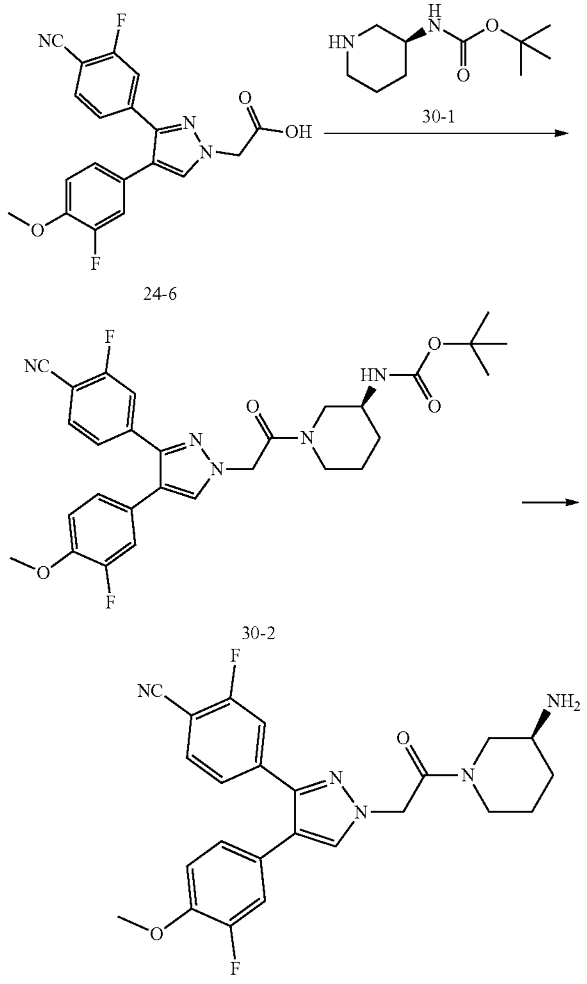

24-6

30-1

30-2

30

Step 1

Compound 24-6 (200 mg, 542 μmol), compound 30-1 (130 mg, 650 μmol) and O-(7-azabenzotriazol-1-yl)-N,N,N,N-tetramethyluronium hexafluorophosphate (309 mg, 812 μmol) were dissolved in N,N-dimethylformamide (2.00 mL), then N,N-diisopropylethylamine (210 mg, 1.62 mmol) was added and the reaction solution was stirred at 20° C. for 12 hours. Water (20 mL) was added to the reaction solution, the mixture was extracted with ethyl acetate (10 mL×3), and the organic phases were combined, washed with saturated brine (20 mL), dried over anhydrous sodium sulfate, filtered, concentrated, and the crude product was separated and purified by column chromatography (1/1, petroleum ether/ethyl acetate, Rf=0.46) to obtain compound 30-2. MS-ESI calculated $[M-56+H]^+$552, found 552.

Step 2

Compound 30-2 (280 mg, 508 μmol) was dissolved in ethyl acetate (3.00 mL), and a solution of hydrogen chloride in ethyl acetate (4 mol/L, 3.00 mL) was added. The reaction solution was stirred at 25° C. for 3 hours. The reaction solution was concentrated under reduced pressure, and the residue was separated and purified by preparative high performance liquid chromatography (Phenomenex Synergi C18 150*30 mm*4 μm; mobile phase A: 0.05% hydrochloric acid aqueous solution; mobile phase B: acetonitrile; B %: 28%-58%, 9 min) to obtain hydrochloride of compound 30. $^1H$ NMR (400 MHz, $CD_3OD$) δ=7.78 (s, 1H), 7.72-7.66 (m, 1H), 7.47-7.39 (m, 2H), 7.10 (t, J=8.8 Hz, 1H), 7.07-6.99 (m, 2H), 5.29 (s, 2H), 4.25-4.01 (m, 1H), 3.89 (s, 3H), 3.82-3.71 (m, 1H), 3.58-3.34 (m, 3H), 2.25-2.08 (m, 1H), 2.02-1.69 (m, 3H). MS-ESI calculated $[M+H]^+$452, found 452.

Embodiment 31

31

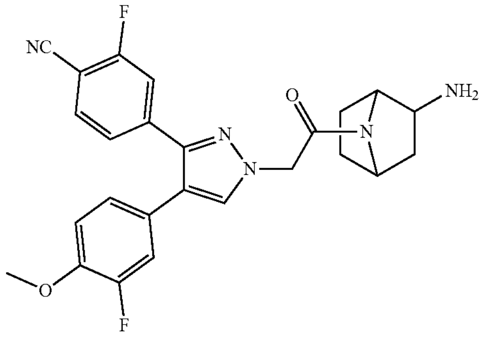

Synthetic Route:

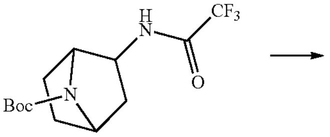

31-1

-continued

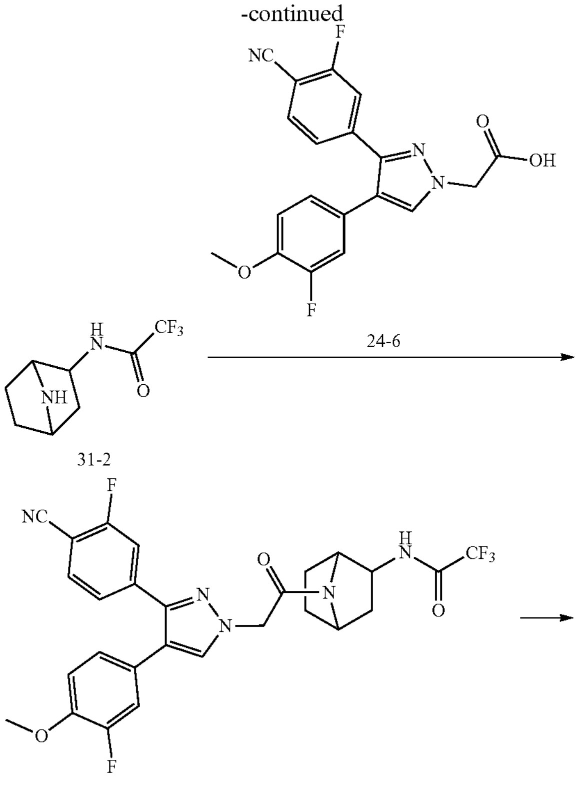

24-6

31-2

31-3

Hydrochloride of compound 31

Step 1

Compound 31-1 (190 mg, 616 μmol) was dissolved in ethyl acetate (3.00 mL), then a solution of hydrogen chloride in ethyl acetate (4 mol/L, 3.00 mL) was added, and the reaction solution was stirred and reacted at 25° C. for 2 hours. The reaction solution was concentrated under reduced pressure to obtain hydrochloride of compound 31-2. MS-ESI calculated $[M+H]^+$209, found 209.

Step 2

Compound 24-6 (200 mg, 541 μmol) was dissolved in N,N-dimethylformamide (5.00 mL), then compound 31-2 (150 mg, 613 μmol), 0-(7-azabenzotriazol-1-yl)-N,N,N,N-tetramethyluronium hexafluorophosphate (309 mg, 812 μmol) and N,N-diisopropylethylamine (280 mg, 2.17 mmol) were added, and the reaction solution was stirred at 25° C. for 12 hours. Water (50.0 mL) was added to the reaction solution, filtered, and the filter cake was washed with water (30.0 mL) and dried under vacuum to obtain compound 31-3. MS-ESI calculated $[M+H]^+$560, found 560.

Step 3

Compound 31-3 (300 mg, 536 μmol) was dissolved in anhydrous tetrahydrofuran (10.0 mL) and water (2.00 mL), and sodium hydroxide (42.9 mg, 1.07 mmol) was added. The reaction solution was stirred at 50° C. for 12 hours. The reaction solution was diluted with water (30.0 mL), and extracted with ethyl acetate (30.0 mL×2). The organic phase was washed with saturated brine (50.0 mL), dried over anhydrous sodium sulfate, filtered, concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 20%-40%, 7 min) to obtain hydrochloride of compound 31. $^1H$ NMR (400 MHz, $CD_3OD$) δ=7.84 (s, 1H), 7.72-7.68 (m, 1H), 7.47-7.41 (m, 2H), 7.14-7.02 (m, 3H), 5.20 (s, 2H), 4.85-4.65 (m, 2H), 3.91 (s, 3H), 3.85-3.67 (m, 1H), 2.52-2.34 (m, 1H), 2.11-1.74 (m, 4H), 1.54-1.42 (m, 1H). MS-ESI calculated $[M+H]^+$464, found 464.

Embodiment 32

32

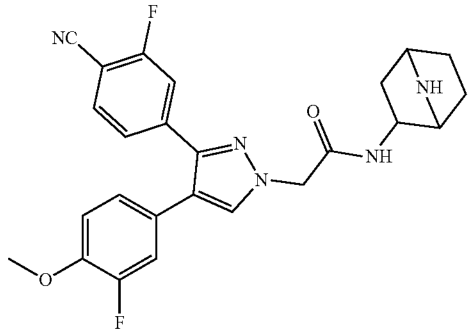

Synthetic Route:

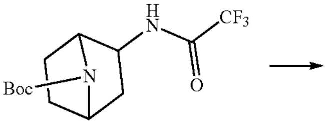

31-1

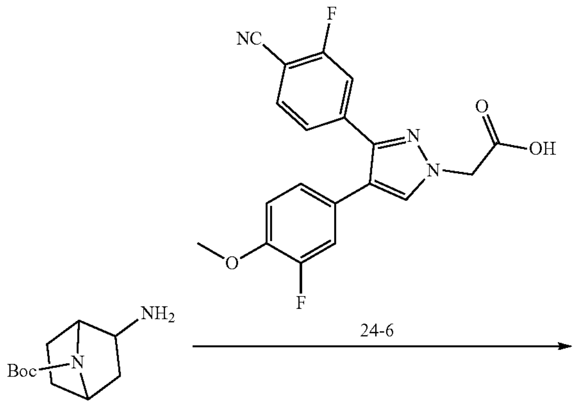

24-6

32-1

-continued

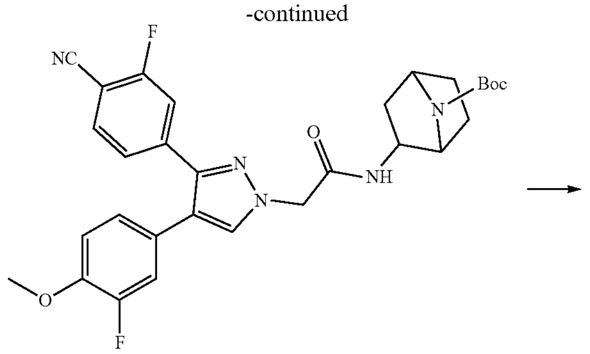

32-2

Hydrochloride of compound 32

Step 1

Compound 31-1 (100 mg, 324 μmol) was dissolved in anhydrous tetrahydrofuran (5.00 mL) and water (1.00 mL), and sodium hydroxide (26.0 mg, 650 μmol) was added. The reaction solution was stirred at 50° C. for 12 hours. The reaction solution was diluted with water (10.0 mL), extracted with ethyl acetate (20.0 mL×2), and the organic phase was washed with saturated brine (30.0 mL), dried over anhydrous sodium sulfate, filtered, concentrated under reduced pressure to obtain compound 32-1. MS-ESI calculated $[M+H]^+$213, found 213.

Step 2

Compound 24-6 (100 mg, 271 μmol) was dissolved in anhydrous N,N-dimethylformamide (5.00 mL), then compound 32-1 (78.0 mg, 367 μmol), 0-(7-azabenzotriazol-1-yl)-N,N,N,N-tetramethyluronium hexafluorophosphate (154 mg, 406 μmol) and N,N-diisopropylethylamine (140 mg, 1.08 mmol) were added, and the reaction solution was stirred at 25° C. for 12 hours. Water (50.0 mL) was added to the reaction solution, filtered, and the filter cake was washed with water (30.0 mL) and dried under vacuum to obtain compound 32-2. MS-ESI calculated $[M-56+H]^+$508, found 508.

Step 3

Compound 32-2 (190 mg, 337 μmol) was dissolved in ethyl acetate (5.00 mL), then a solution of hydrogen chloride in ethyl acetate (4 mol/L, 5.00 mL) was added, and the reaction solution was stirred and reacted at 25° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 20%-40%, 7 min) to obtain hydrochloride of compound 32. $^1H$ NMR (400 MHz, $CD_3OD$) δ=7.85 (s, 1H), 7.72-7.68 (m, 1H), 7.47-7.41 (m, 2H), 7.14-7.02 (m, 3H), 5.04 (s, 2H), 4.45-4.40 (m, 1H), 4.37-4.35 (m, 1H), 4.25-4.23 (m, 1H), 3.91 (s, 3H), 2.48-2.42 (m, 1H), 2.23-2.18 (m, 1H), 2.05-2.02 (m, 1H), 1.92-1.84 (m, 2H), 1.63-1.59 (m, 1H). MS-ESI calculated $[M+H]^+$464, found 464.

Embodiment 33

33

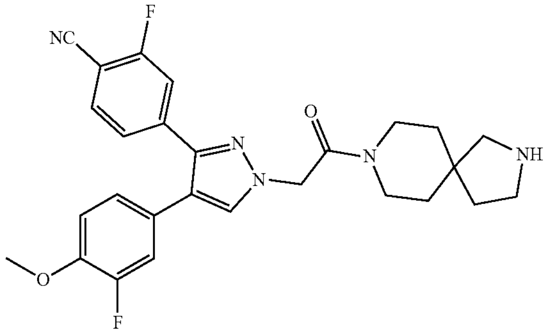

Synthetic Route:

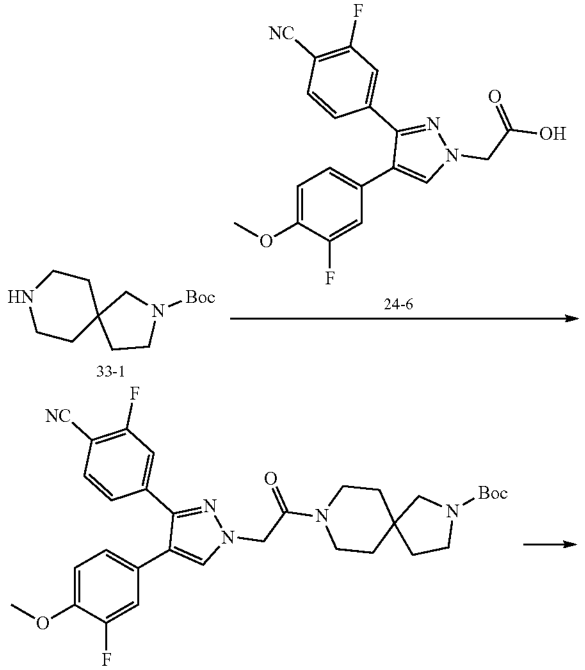

33-1

33-2

Hydrochloride of compound 33

Step 1

Compound 24-6 (100 mg, 271 μmol) was dissolved in anhydrous N,N-dimethylformamide (5.00 mL), then compound 33-1 (69.0 mg, 287 μmol), 0-(7-azabenzotriazol-1-yl)-N,N,N,N-tetramethyluronium hexafluorophosphate (154 mg, 406 μmol) and N,N-diisopropylethylamine (140 mg, 1.08 mmol) were added, and the reaction solution was stirred at 28° C. for 12 hours. Water (50.0 mL) was added to the reaction solution, filtered, and the filter cake was washed with water (30.0 mL) and dried under vacuum to obtain compound 33-2. Compound 33-2 MS-ESI calculated $[M+H]^+$592, found 592.

Step 2

Compound 33-2 (187 mg, 316 μmol) was dissolved in ethyl acetate (5.00 mL), and a solution of hydrogen chloride in ethyl acetate (4 mol/L, 5.00 mL) was added. The reaction solution was stirred at 28° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 21%-41%, 7 min) to obtain hydrochloride of compound 33. $^1$H NMR (400 MHz, CD3OD) δ=7.80 (s, 1H), 7.71-7.68 (m, 1H), 7.47-7.41 (m, 2H), 7.13-7.03 (m, 3H), 5.28 (s, 2H), 3.91 (s, 3H), 3.79-3.58 (m, 4H), 3.47-3.43 (m, 2H), 3.21 (s, 2H), 2.07-2.03 (m, 2H), 1.81-1.79 (m, 2H), 1.71-1.68 (m, 2H). MS-ESI calculated $[M+H]^+$492, found 492.

Embodiment 34

34

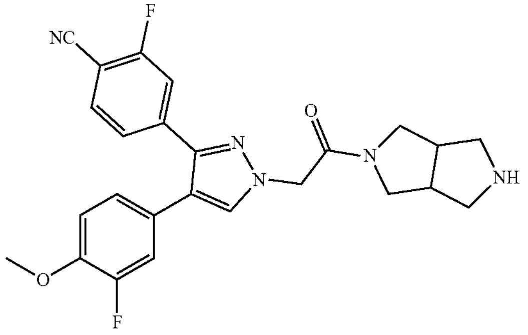

Synthetic Route:

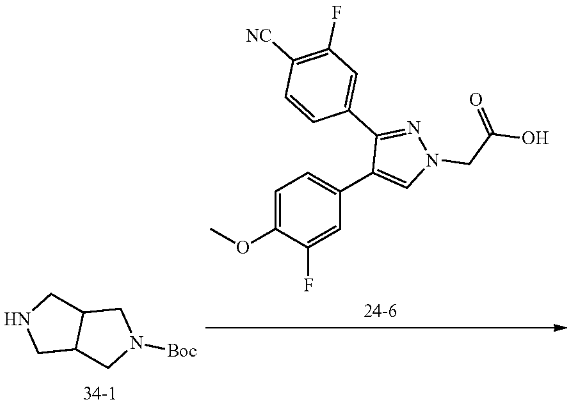

34-1

-continued

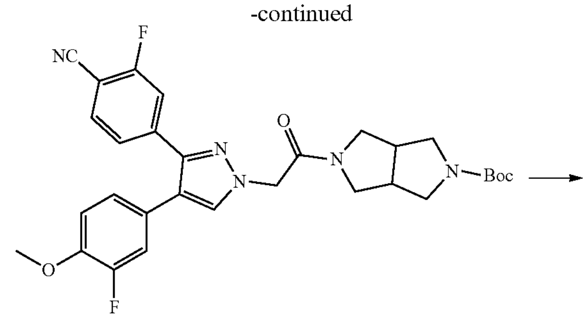

34-2

Hydrochloride of compound 34

Step 1

Compound 24-6 (100 mg, 271 μmol) was dissolved in anhydrous N,N-dimethylformamide (5.00 mL), then compound 34-1 (60.4 mg, 284 μmol), 0-(7-azabenzotriazol-1-yl)-N,N,N,N-tetramethyluronium hexafluorophosphate (154 mg, 406 μmol) and N,N-diisopropylethylamine (140 mg, 1.08 mmol) were added, and the reaction solution was stirred at 28° C. for 12 hours. Water (50.0 mL) was added to the reaction solution, filtered, and the filter cake was washed with water (30.0 mL) and dried under vacuum to obtain compound 34-2. MS-ESI calculated $[M+H]^+$564, found 564.

Step 2

Compound 34-2 (189 mg, 335 μmol) was dissolved in ethyl acetate (5.00 mL), then a solution of hydrogen chloride in ethyl acetate (4 mol/L, 5.00 mL) was added, and the reaction solution was stirred and reacted at 28° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 20%-40%, 7 min) to obtain hydrochloride of compound 34. $^1$H NMR (400 MHz, $CD_3OD$) δ=7.83 (s, 1H), 7.71-7.68 (m, 1H), 7.47-7.41 (m, 2H), 7.13-7.03 (m, 3H), 5.27-5.14 (m, 2H), 3.95-3.92 (m, 1H), 3.91 (s, 3H), 3.79-3.74 (m, 2H), 3.67-3.59 (m, 3H), 3.32-3.30 (m, 2H), 3.27-3.18 (m, 2H). MS-ESI calculated $[M+H]^+$464, found 464.

Embodiment 35

35

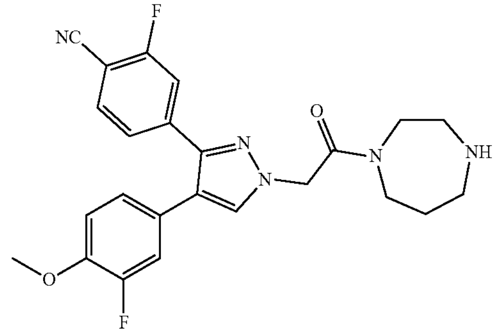

Synthetic Route:

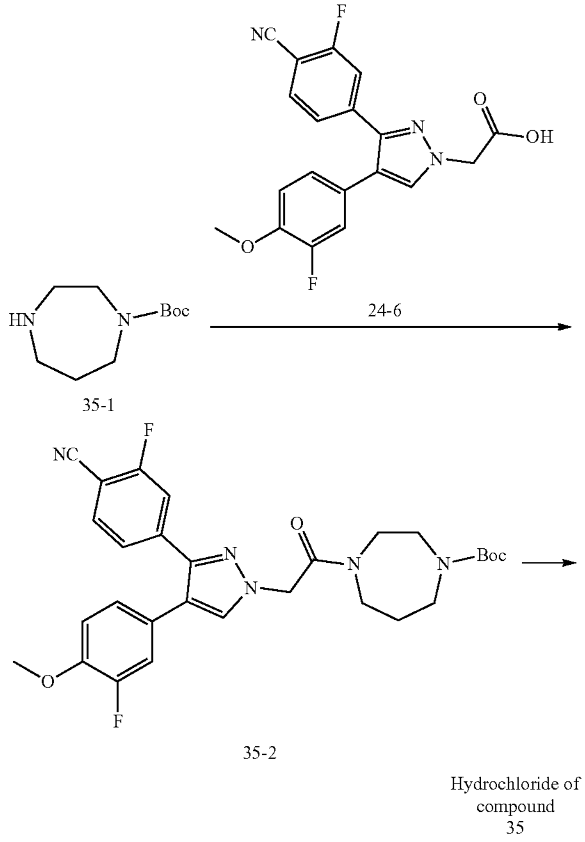

24-6

35-1

35-2

Hydrochloride of compound 35

Step 1

Compound 24-6 (130 mg, 352 μmol) was dissolved in anhydrous N,N-dimethylformamide (6.00 mL), then compound 35-1 (74.0 mg, 369 μmol), 0-(7-azabenzotriazol-1-yl)-N,N,N,N-tetramethyluronium hexafluorophosphate (201 mg, 528 μmol) and N,N-diisopropylethylamine (182 mg, 1.41 mmol) were added, and the reaction solution was stirred at 28° C. for 12 hours. Water (60.0 mL) was added to the reaction solution, filtered, and the filter cake was washed with water (30.0 mL) and dried under vacuum to obtain compound 35-2. MS-ESI calculated $[M+H]^+552$, found 552.

Step 2

Compound 35-2 (248 mg, 449 μmol) was dissolved in ethyl acetate (5.00 mL), then a solution of hydrogen chloride in ethyl acetate (4 mol/L, 5.00 mL) was added, and the reaction solution was stirred and reacted at 28° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 20%-40%, 7 min) to obtain hydrochloride of compound 35. $^1H$ NMR (400 MHz, $CD_3OD$) δ=7.86 (d, J=1.2 Hz, 1H), 7.73-7.69 (m, 1H), 7.47-7.42 (m, 2H), 7.14-7.03 (m, 3H), 5.34 (s, 2H), 4.01-3.92 (m, 1H), 3.91 (s, 3H), 3.90-3.88 (m, 1H), 3.82-3.76 (m, 2H), 3.56-3.44 (m, 2H), 3.39-3.34 (m, 2H), 2.30-2.09 (m, 2H). MS-ESI calculated $[M+H]^+452$, found 452.

Embodiment 36

36

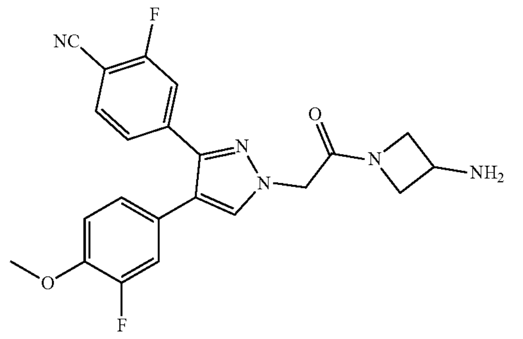

Synthetic Route:

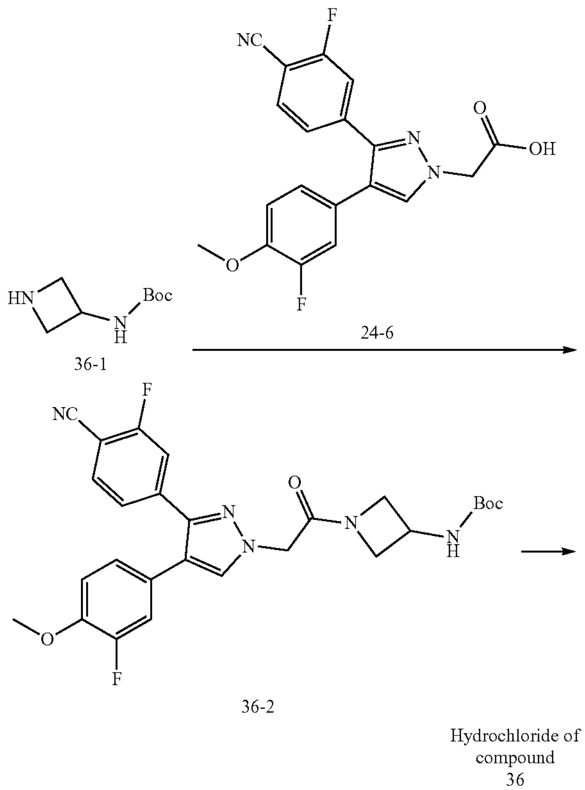

36-1

24-6

36-2

Hydrochloride of compound 36

Step 1

Compound 24-6 (110 mg, 298 μmol) was dissolved in anhydrous N,N-dimethylformamide (5.00 mL), then compound 36-1 (53.8 mg, 313 μmol), 0-(7-azabenzotriazol-1-yl)-N,N,N,N-tetramethyluronium hexafluorophosphate (170 mg, 447 μmol) and N,N-diisopropylethylamine (154 mg, 1.19 mmol) were added, and the reaction solution was stirred at 28° C. for 12 hours. Water (50.0 mL) was added to the reaction solution, filtered, and the filter cake was washed with water (30.0 mL) and dried under vacuum to obtain compound 36-2. MS-ESI calculated $[M+H]^+$524, found 524.

Step 2

Compound 36-2 (150 mg, 286 μmol) was dissolved in ethyl acetate (5.00 mL), then a solution of hydrogen chloride in ethyl acetate (4 mol/L, 5.00 mL) was added, and the reaction solution was stirred and reacted at 28° C. for 2 hours. The reaction solution was concentrated under reduced pressure, and the residue was separated and purified by preparative high performance liquid chromatography (3_Phenomenex Luna C18 75*30 mm*3 μm; mobile phase A: 0.05% hydrochloric acid aqueous solution; mobile phase B: acetonitrile; B %: 19%-39%, 7 min) to obtain hydrochloride of compound 36. $^1H$ NMR (400 MHz, $CD_3OD$) δ=7.85 (s, 1H), 7.73-7.69 (m, 1H), 7.49-7.41 (m, 2H), 7.14-7.02 (m, 3H), 5.03 (s, 2H), 4.68-4.64 (m, 1H), 4.45-4.40 (m, 1H), 4.32-4.28 (m, 1H), 4.25-4.19 (m, 1H), 4.09-4.05 (m, 1H), 3.91 (s, 3H). MS-ESI calculated $[M+H]^+$424, found 424.

Biochemical Assay:

Experimental Embodiment 1: Evaluation of LSD1 Enzyme Activity

The purpose of this assay was to detect the inhibitory activity of the compounds against LSD1 in vitro. The enzyme used in this assay was human LSD1 and the standard substrate was histone H3K4me peptide (20 M); the activity of the compounds was determined by the enzyme fluorescence coupling method using a combination of horseradish peroxidase (HRP) and Amplex Red to detect the $H_2O_2$ generated after the reaction. The $IC_{50}$ values of the compounds were measured at 10 concentrations after 3 times dilution from 10 μm. Before the compound was added to the substrate to start the reaction, enzyme and substrate were incubated for 30 minutes. Fluorescence detector: EnVision, excitation wavelength: Ex/Em=530/590 nM.

The compounds were tested for their LSD1 inhibitory activity and the results are shown in Table 1.

TABLE 1

Screening test results of enzyme activity of compounds of the present disclosure in vitro

| Compound number | $IC_{50}$ (nM) |
|---|---|
| Hydrochloride of compound 1 | 330.1 |
| Hydrochloride of compound 9 | 228.1 |
| Hydrochloride of compound 10 | 97.91 |
| Hydrochloride of compound 12 | 568.7 |
| Hydrochloride of compound 15 | 275 |
| Hydrochloride of compound 18 | 194.4 |
| Hydrochloride of compound 19 | 349.3 |
| Hydrochloride of compound 22 | 112.5 |
| Hydrochloride of compound 27 | 525.5 |
| Hydrochloride of compound 29 | 307.5 |
| Hydrochloride of compound 31 | 289.7 |
| Hydrochloride of compound 32 | 432.6 |

TABLE 1-continued

Screening test results of enzyme activity of compounds of the present disclosure in vitro

| Compound number | $IC_{50}$ (nM) |
|---|---|
| Hydrochloride of compound 34 | 302.8 |
| Hydrochloride of compound 35 | 186.4 |
| Hydrochloride of compound 36 | 307.5 |

Conclusion: The compounds of this disclosure have obvious inhibitory activity against LSD1.

Experimental Embodiment 2: Evaluation of Proliferation Inhibitory Activity Against NCI-H1417 Cells Experimental purpose: To detect the inhibitory activity of the compounds against NCI-H1417 cells.

Experimental materials: RPMI 1640 medium, fetal bovine serum, Promega CellTiter-Glo reagent. The NCI-H1417 cell line was purchased from ATCC. Envision multilabel analyzer (PerkinElmer).

Experimental method: The compounds were dissolved to 10 mM, and the compounds were diluted 5 times with DMSO in the compound plate. The starting concentration of the compound was 2 mM, diluted 3 times with Bravo to 10 concentrations. Echo was used to transfer 250 nL to the top and bottom double wells of a blank 384 cell plate, and 250 nL of DMSO/compound was added to a cell suspension of 1000 cells/50 μL per well, and the compounds were diluted 200 times, i.e. the starting concentration was 10 μM. Cell plates were incubated in a carbon dioxide incubator for 10 days. 25 μL of Promega CellTiter-Glo reagent per well was added to the cell plate, and the mixture was shaken for 10 minutes at room temperature to stabilize the luminescence signal. Readings were taken using a PerkinElmer Envision multilabel analyzer.

Data analysis: The equation (Max-Ratio)/(Max-Min) *100% was used to convert the original data into inhibition rate, the $IC_{50}$ value can be obtained by curve fitting with four parameters. (derived from 205 mode in XLFIT5, iDBS)

The inhibitory activity of compounds against NCI-H1417 cell proliferation was tested, and the results are shown in Table 2.

TABLE 2

Test results of NCI-H1417 cell proliferation inhibition of compounds of the present disclosure

| Compound number | $IC_{50}$ (nM) |
|---|---|
| Hydrochloride of compound 10 | 42.55 |
| Hydrochloride of compound 15 | 76.77 |
| Hydrochloride of compound 19 | 28.90 |
| Hydrochloride of compound 22 | 107.34 |

Conclusion: The compounds of this disclosure have obvious inhibitory activity against the proliferation of NCI-H1417 cells.

What is claimed is:

1. A compound represented by formula (II) or a pharmaceutically acceptable salt thereof, (II)

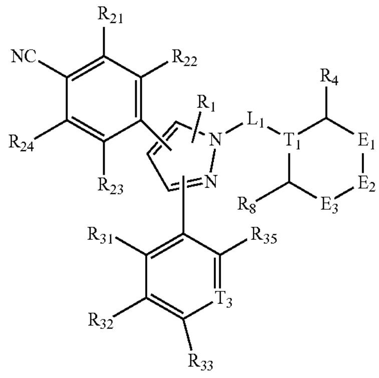

wherein, $L_1$ is single bond, —$CH_2$—, —$CH_2$—C(═O)— or —$CH_2$—C(═O)—NH—;

$T_1$ is $CR_{t1}$ or N;

$T_3$ is $CR_{34}$ or N;

$E_1$ is single bond, —$C(R_5)_2$— or —$C(R_5)_2C(R_5)_2$—;

$E_2$ is O, —$NR_6$— or —$C(R_{61})_2$—;

$E_3$ is single bond, —$C(R_7)_2$— or —$C(R_7)_2C(R_7)_2$—;

$R_1$ is H, halogen or $C_{1-3}$ alkyl, wherein the $C_{1-3}$ alkyl is optionally substituted by one, two or three $R_a$;

$R_{21}$, $R_{22}$, $R_{23}$ and $R_{24}$ are independently H or halogen;

$R_{31}$, $R_{32}$, $R_{33}$, $R_{34}$ and $R_{35}$ are independently H, halogen, $C_{1-3}$ alkyl or $C_{1-3}$ alkoxyl, wherein the $C_{1-3}$ alkyl and $C_{1-3}$ alkoxyl are optionally substituted by one, two or three $R_b$;

$R_4$ is H, halogen or $C_{1-3}$ alkyl, wherein the $C_{1-3}$ alkyl is optionally substituted by one, two or three $R_e$;

$R_5$ is independently H, halogen, OH, $NH_2$ or $C_{1-3}$ alkyl, wherein the $C_{1-3}$ alkyl is optionally substituted by one, two or three $R_d$;

$R_6$ is H or $C_{1-3}$ alkyl, wherein the $C_{1-3}$ alkyl is optionally substituted by one, two or three $R_e$;

$R_{61}$ is independently H, halogen, OH, $NH_2$ or $C_{1-3}$ alkyl, wherein the $C_{1-3}$ alkyl is optionally substituted by one, two or three $R_f$;

$R_7$ is independently H, halogen, OH, $NH_2$ or $C_{1-3}$ alkyl, wherein the $C_{1-3}$ alkyl is optionally substituted by one, two or three $R_g$;

$R_8$ is independently H, halogen, OH, $NH_2$ or $C_{1-3}$ alkyl, wherein the $C_{1-3}$ alkyl is optionally substituted by one, two or three $R_h$;

or, $R_{32}$ and $R_{33}$ are attached together so that the structural unit

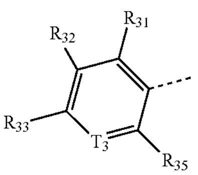

is

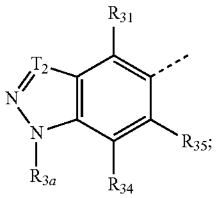

$T_2$ is $CR_{t2}$ or N;

$R_{3a}$ is H or $C_{1-3}$ alkyl, wherein the $C_{1-3}$ alkyl is optionally substituted by one, two or three $R_i$;

or, $R_5$ and $R_{61}$ are attached together so that the structural unit

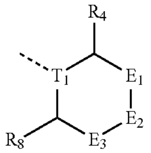

is

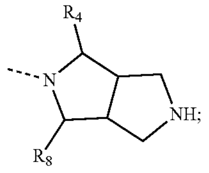

or, two $R_{61}$ are attached together with the C atom to which they are attached so that the structural unit

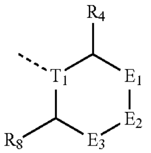

is

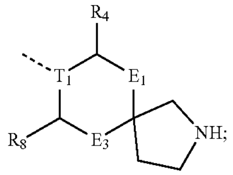

or, $R_4$ and $R_7$ are attached together so that the structural unit

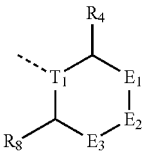

is

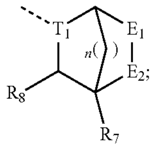

or, $R_4$ and $R_8$ are attached together so that the structural unit

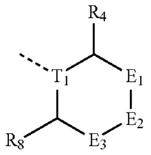

is

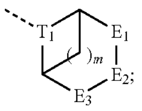

$R_{t1}$ is H or OH;

$R_{t2}$ is H or halogen;

$R_a$, $R_b$, $R_c$, $R_d$, $R_e$, $R_f$, $R_g$ and $R_h$ are independently halogen, OH or $NH_2$;

$R_1$ is independently halogen, OH or $CH_3$;

n is 1 or 2;

m is 1 or 2.

2. The compound or the pharmaceutically acceptable salt thereof as defined in claim 1, wherein, the compound has the structure represented by formula (I-1), (I-2), (I-3), (I-4) or (I-5):

(I-1)

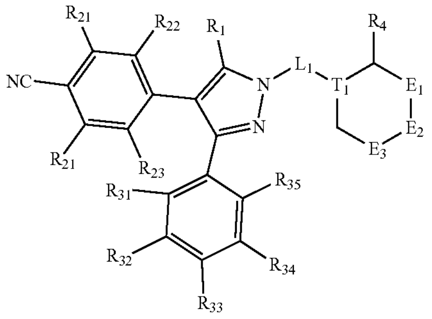

-continued (I-5)

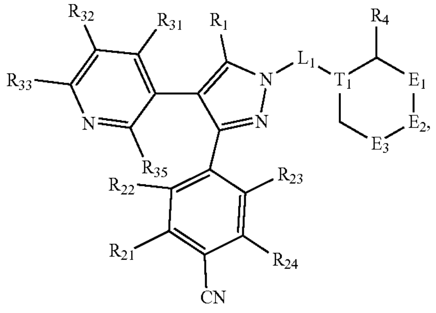

(I-2)

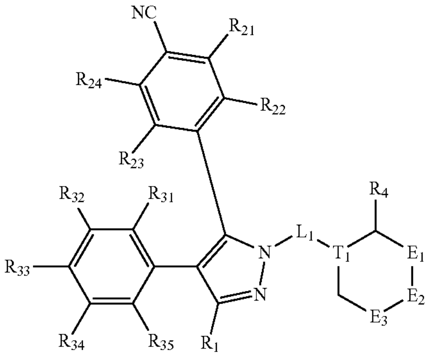

(I-3)

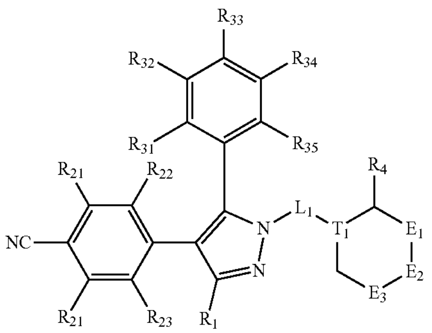

(I-4)

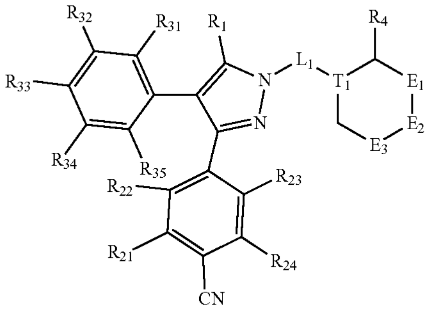

wherein, $L_1$, $T_1$, $E_1$, $E_2$, $E_3$, $R_1$, $R_{21}$, $R_{22}$, $R_{23}$, $R_{24}$, $R_{31}$, $R_{32}$, $R_{33}$, $R_{34}$, $R_{35}$ and $R_4$ are as defined in claim 1.

3. The compound or the pharmaceutically acceptable salt thereof as defined in claim 1, wherein, $R_1$ is H, F, Cl, Br, I or $CH_3$, wherein the $CH_3$ is optionally substituted by one, two or three $R_a$;

and/or, $R_{21}$, $R_{22}$, $R_{23}$ and $R_{24}$ are independently H, F, Cl, Br or I;

and/or, $R_{31}$, $R_{32}$, $R_{33}$, $R_{34}$ and $R_{35}$ are independently H, F, Cl, Br, I, $CH_3$ or $-OCH_3$, wherein the $CH_3$ or $-OCH_3$ is optionally substituted by one, two or three $R_b$;

and/or, $R_4$ is H, F, Cl, Br, I or $CH_3$, wherein the $CH_3$ is optionally substituted by one, two or three $R_c$;

and/or, $R_5$ is independently H, F, Cl, Br, I, OH, $NH_2$ or $CH_3$, wherein the $CH_3$ is optionally substituted by one, two or three $R_d$;

and/or, $R_6$ is H or $CH_3$, wherein the $CH_3$ is optionally substituted by one, two or three $R_e$;

and/or, $R_{61}$ is independently H, F, Cl, Br, I, OH, $NH_2$ or $CH_3$, wherein the $CH_3$ is optionally substituted by one, two or three $R_f$;

and/or, $R_7$ is independently H, F, Cl, Br, I, OH, $NH_2$ or $CH_3$, wherein the $CH_3$ is optionally substituted by one, two or three $R_g$;

and/or, $R_8$ is H.

4. The compound or the pharmaceutically acceptable salt thereof as defined in claim 3, wherein, $R_1$ is H, F or $CH_3$;

and/or, $R_{31}$, $R_{32}$, $R_{33}$, $R_{34}$ and $R_{35}$ are independently H, F, Cl, Br, I, $CH_3$, $CF_3$ or $-OCH_3$;

and/or, $R_4$ is H or $CH_3$;

and/or, $R_5$ is independently H or $NH_2$;

and/or, $R_6$ is H;

and/or, $R_{61}$ is independently H or $NH_2$;

and/or, $R_7$ is independently H or $NH_2$.

5. The compound or the pharmaceutically acceptable salt thereof as defined in claim 1, wherein, the structural unit

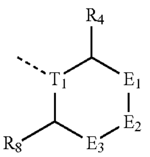 is 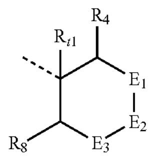 or

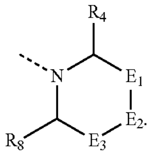

6. The compound or the pharmaceutically acceptable salt thereof as defined in claim 5, wherein, the structural unit

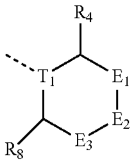

is

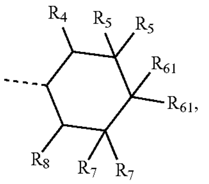

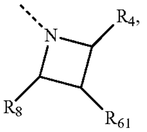

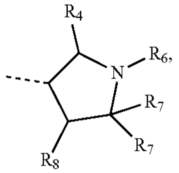

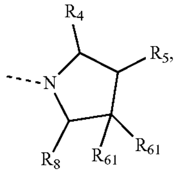

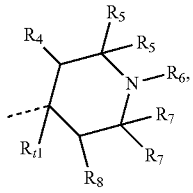

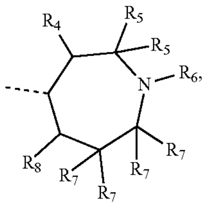

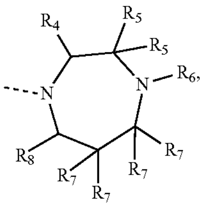

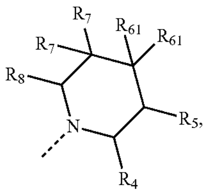

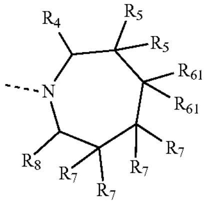

or

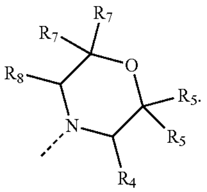

7. The compound or the pharmaceutically acceptable salt thereof as defined in claim 6, wherein, the structural unit

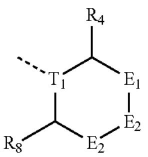

is

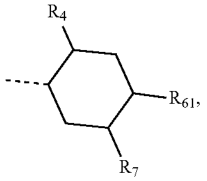

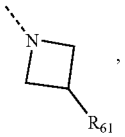

,

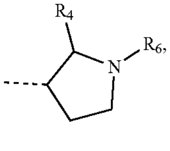

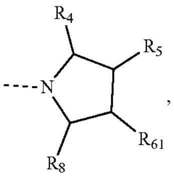

,

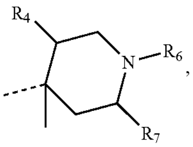

-continued

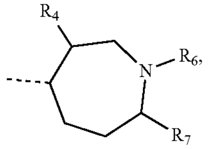

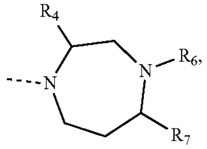

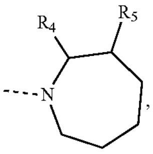

,

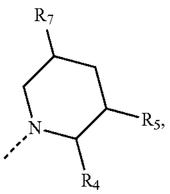

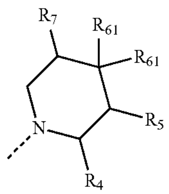

or

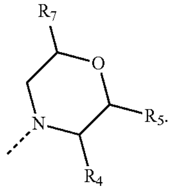

8. The compound or the pharmaceutically acceptable salt thereof as defined in claim 7, wherein, the structural unit

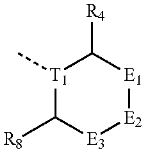

is

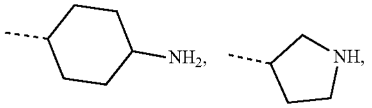

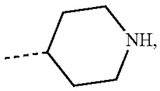

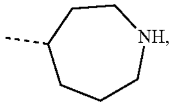

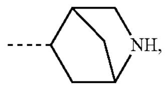

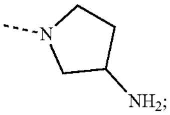

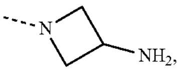

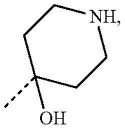

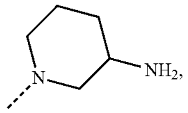

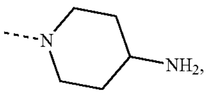

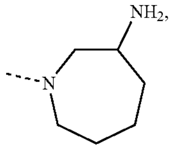

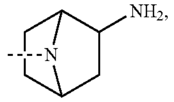

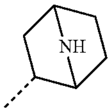

,

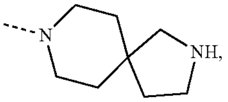

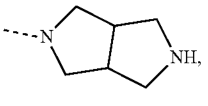

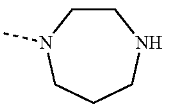

or

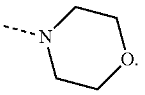

9. The compound or the pharmaceutically acceptable salt thereof as defined in claim 1, wherein, the compound is -continued
(I-1A)
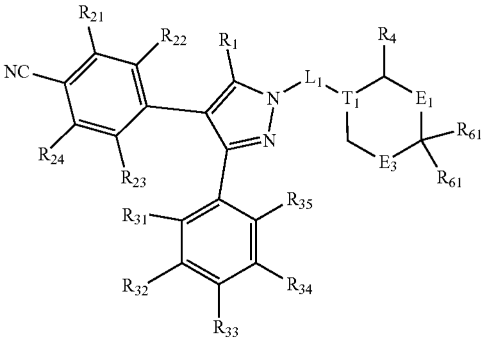
(I-1B)
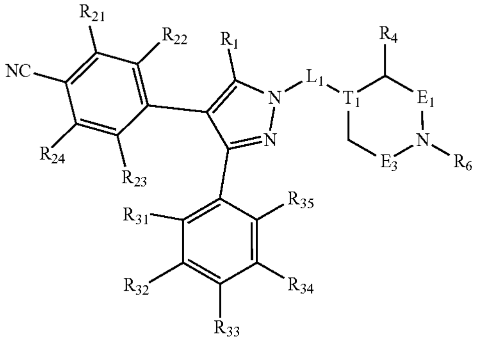
(I-2A)
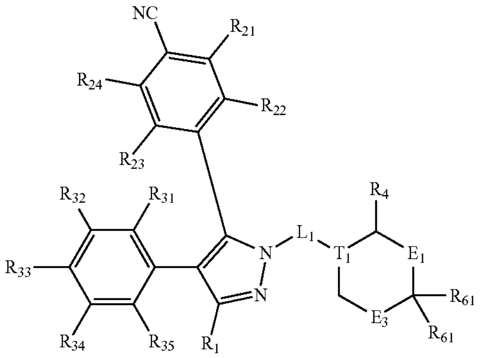
(I-2B)
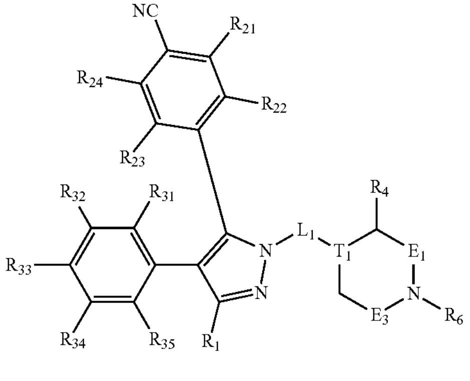
(I-2C)
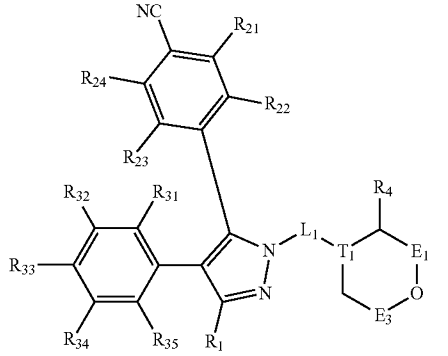
(I-3A)
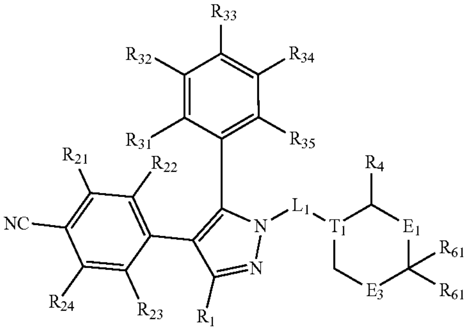
(I-3B)
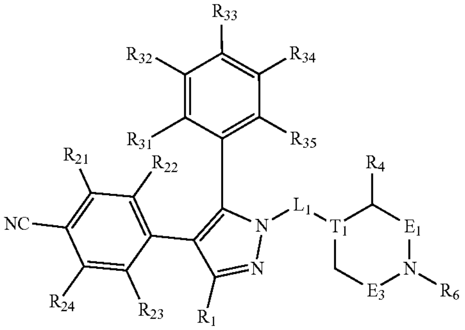
(I-4A)
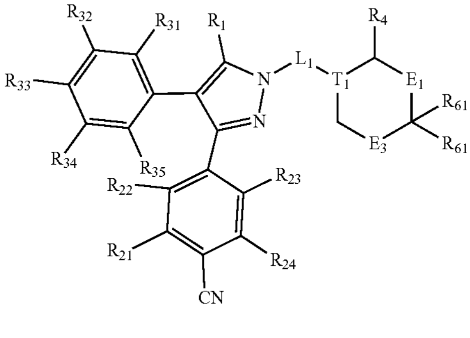

-continued (I-4B)

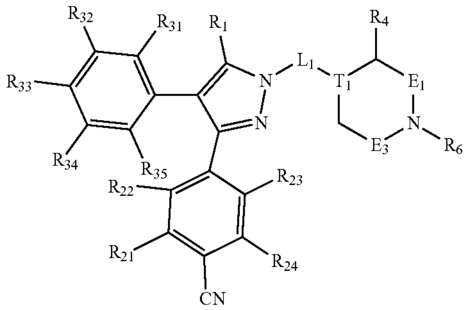

(I-4C)

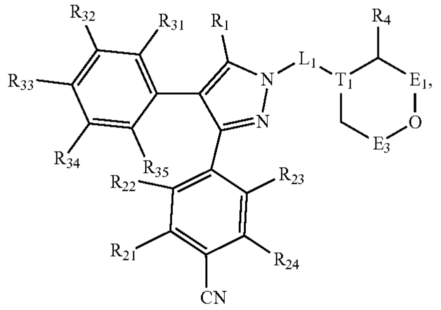

(I-5A)

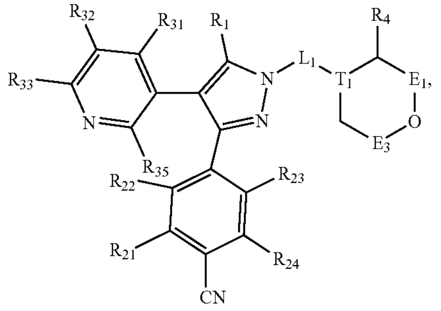

wherein, $L_1$, $T_1$, $E_1$, $E_3$, $R_1$, $R_{21}$, $R_{22}$, $R_{23}$, $R_{24}$, $R_{31}$, $R_{32}$, $R_{33}$, $R_{34}$, $R_{35}$, $R_4$, $R_6$ and $R_{61}$ are as defined in claim 1.

10. The compound or the pharmaceutically acceptable salt thereof as defined in claim 1, wherein, the compound is (I-4A-1)

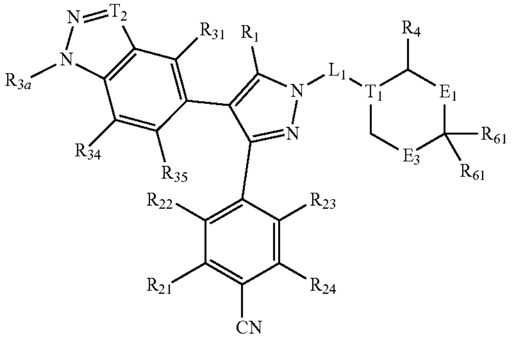

-continued (I-4B-1)

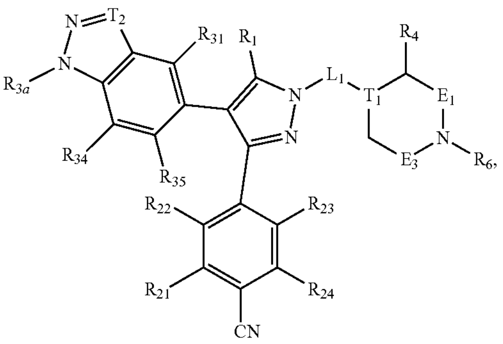

wherein, $L_1$, $T_1$, $T_2$, $E_1$, $E_3$, $R_1$, $R_{21}$, $R_{22}$, $R_{23}$, $R_{24}$, $R_{31}$, $R_{34}$, $R_{35}$, $R_{3a}$, $R_4$, $R_6$ and $R_{61}$ are as defined in claim 1.

11. The compound or the pharmaceutically acceptable salt thereof as defined in claim 1, wherein, the compound is

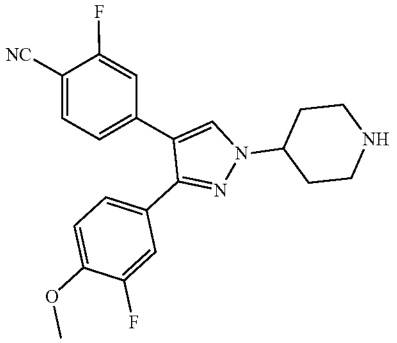

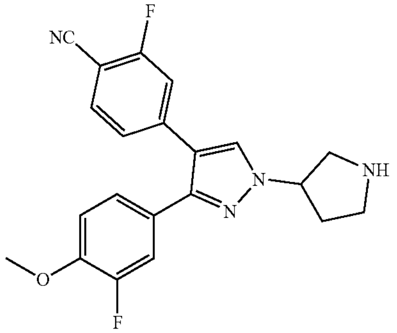

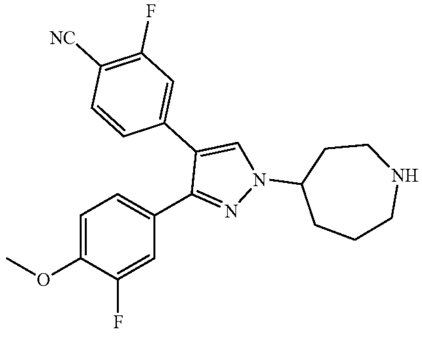

-continued
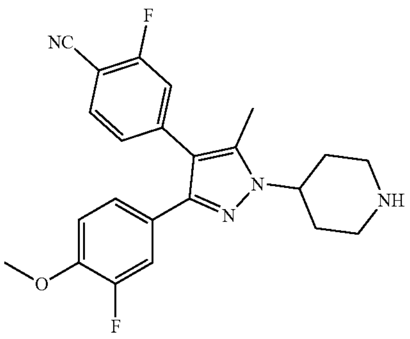
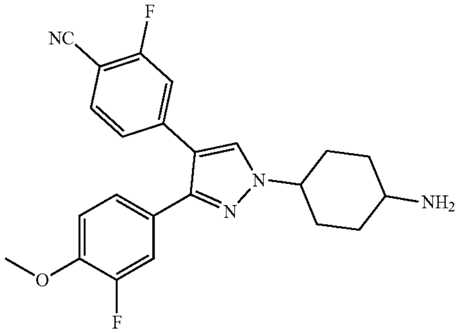
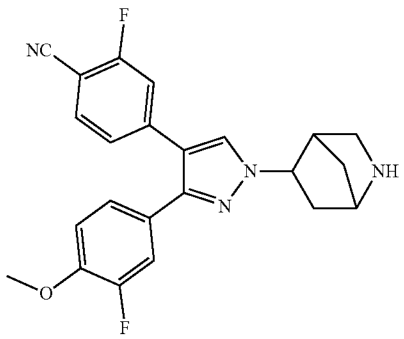
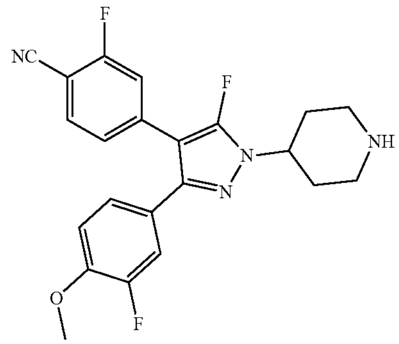
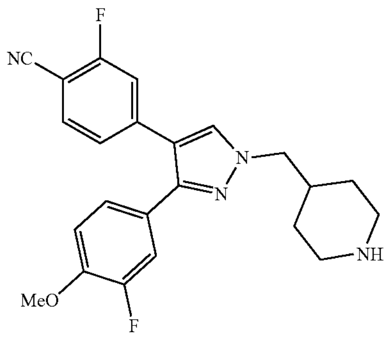
-continued
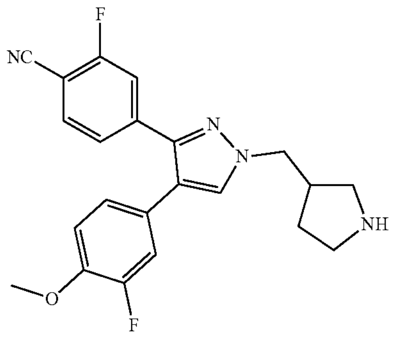
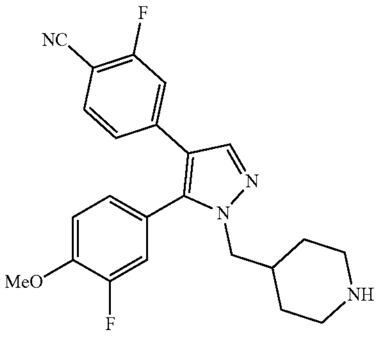
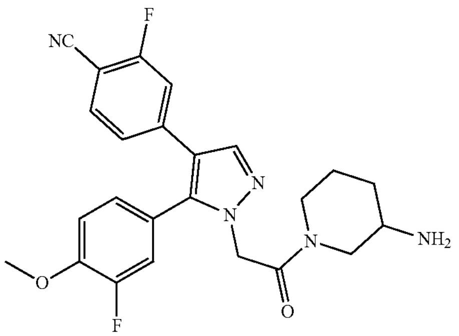
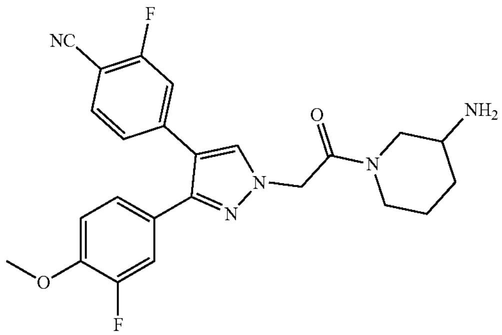
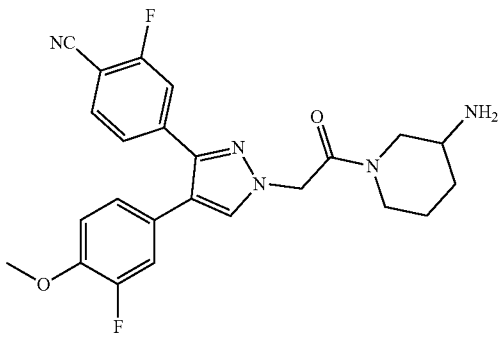

-continued
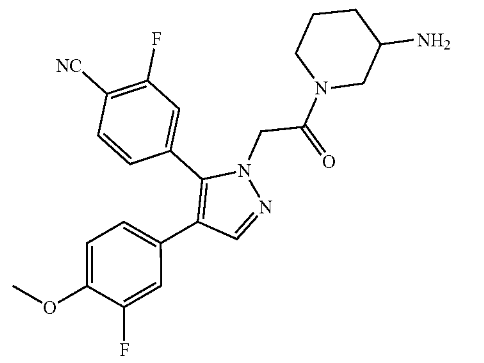
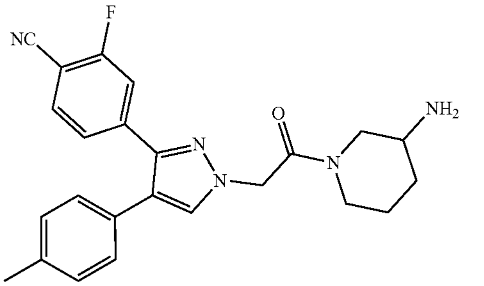
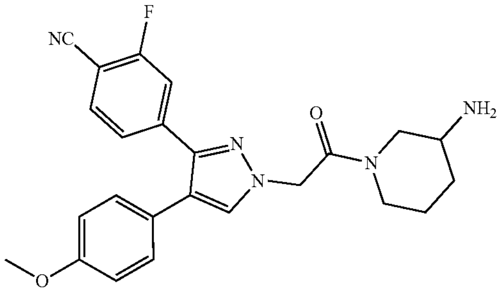
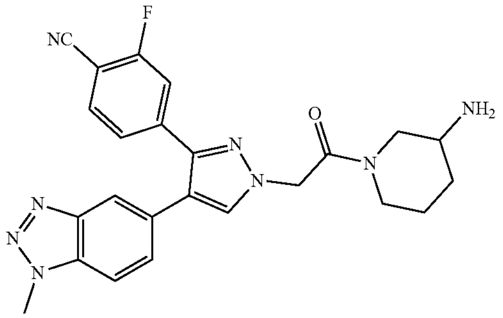
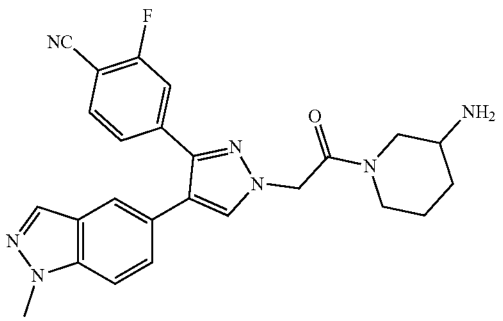
-continued
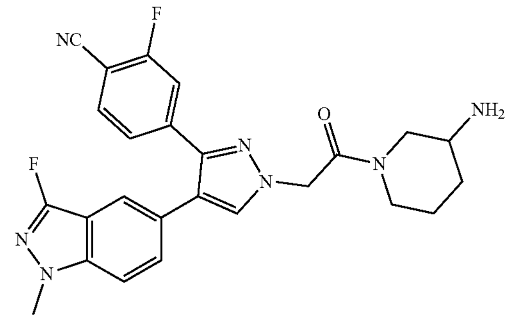
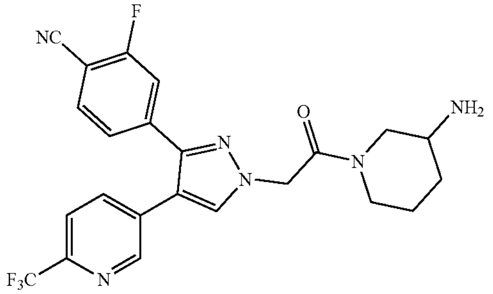
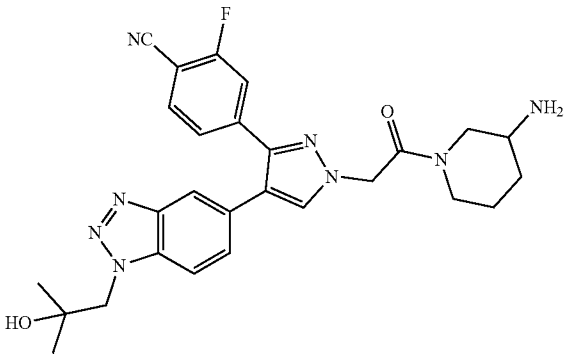
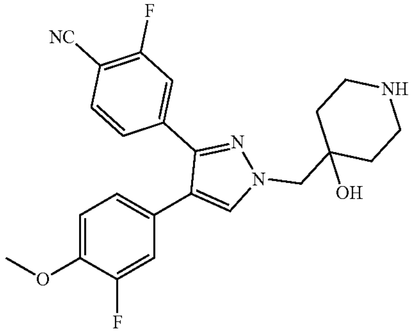
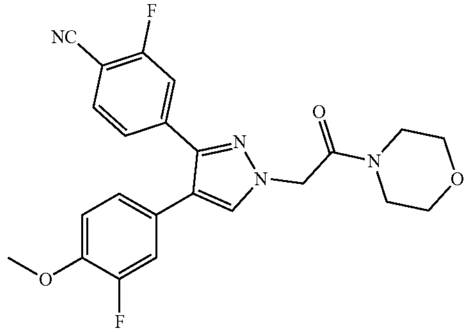

-continued
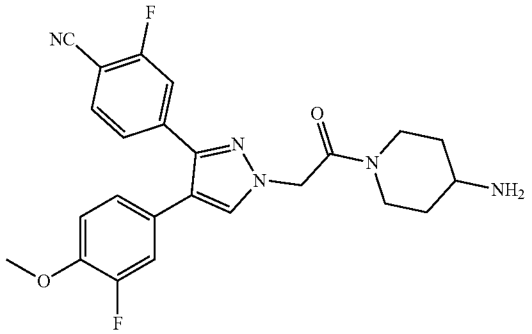
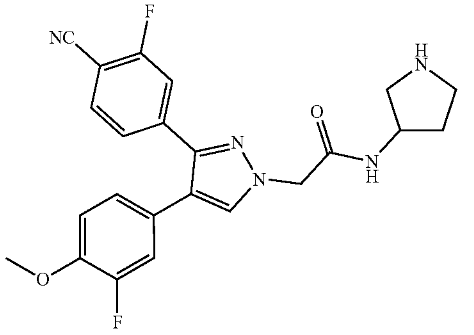
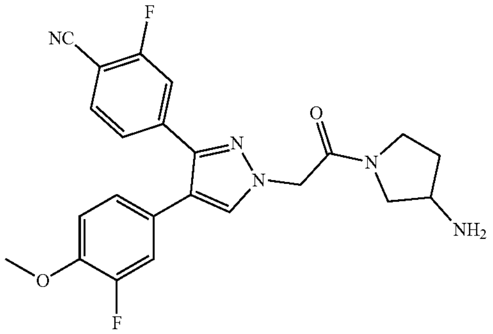
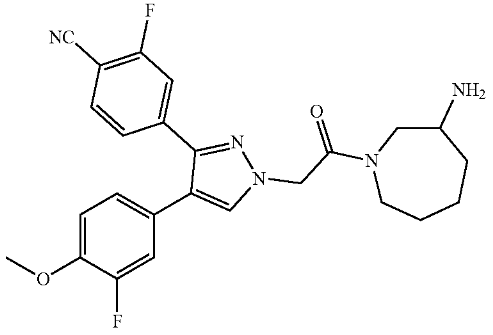
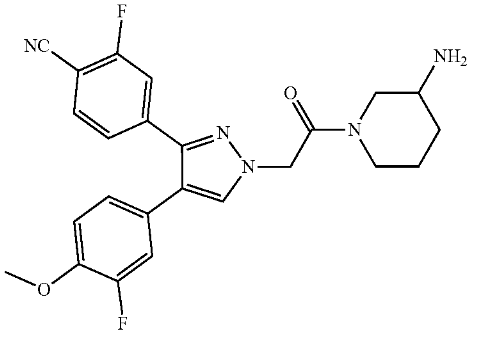
-continued
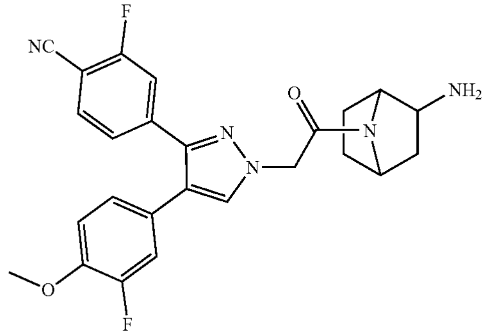
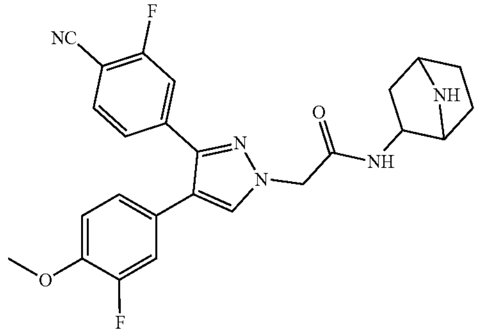
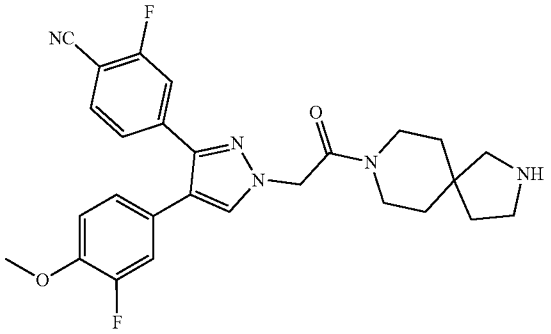
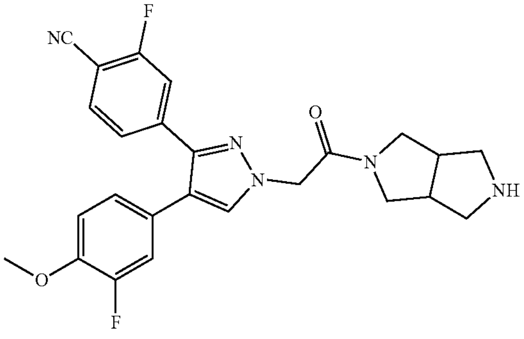
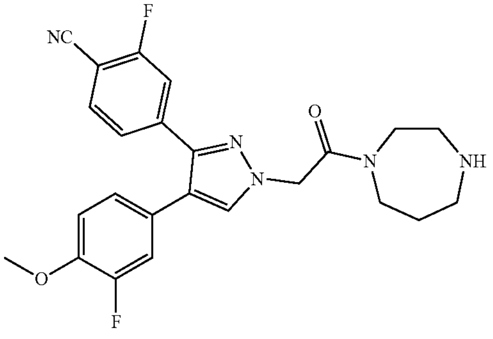
or -continued
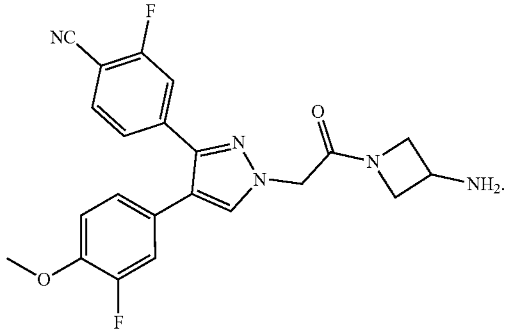
12. The compound or the pharmaceutically acceptable salt thereof as defined in claim 11, wherein, the compound is
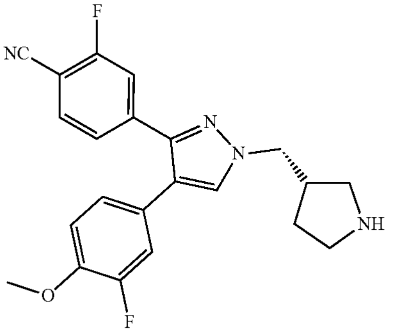
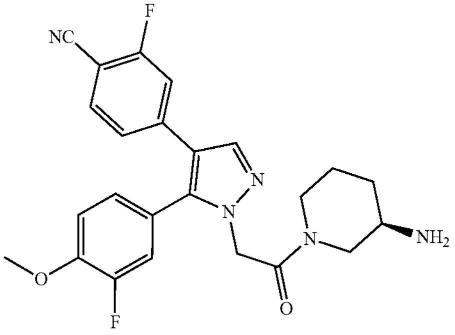
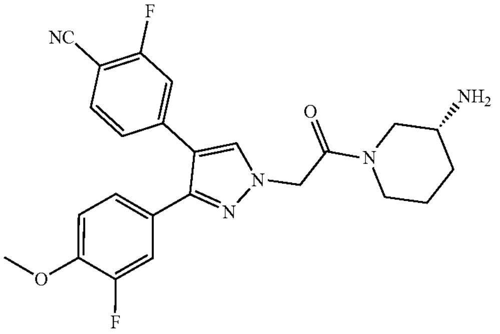
-continued
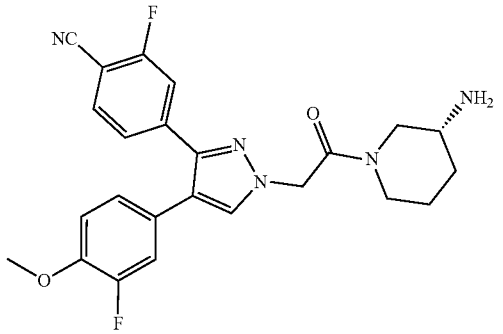
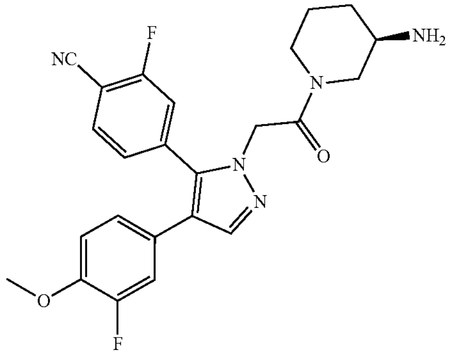
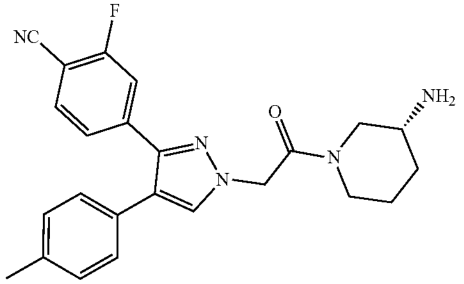
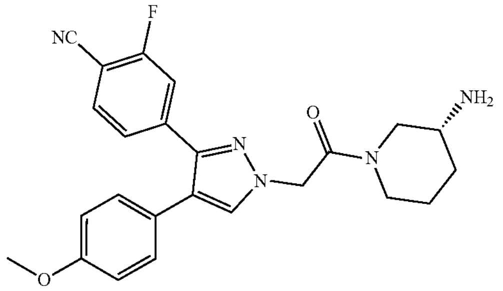
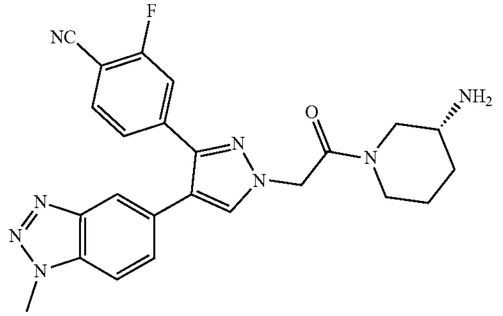

-continued

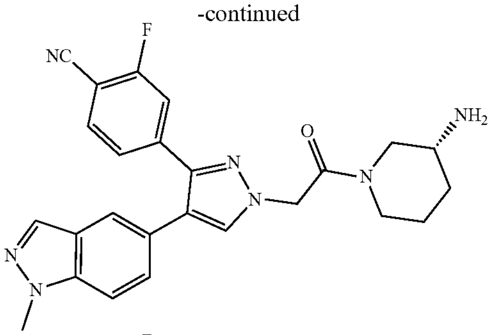

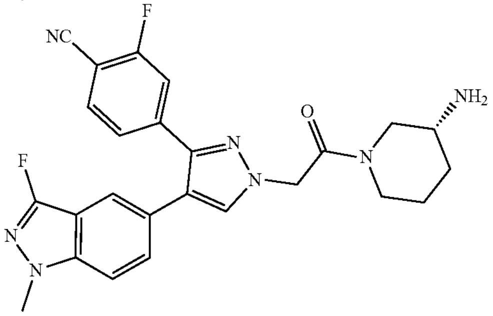

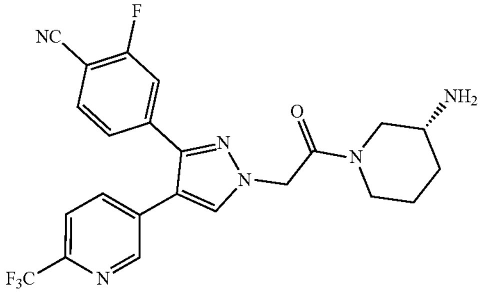

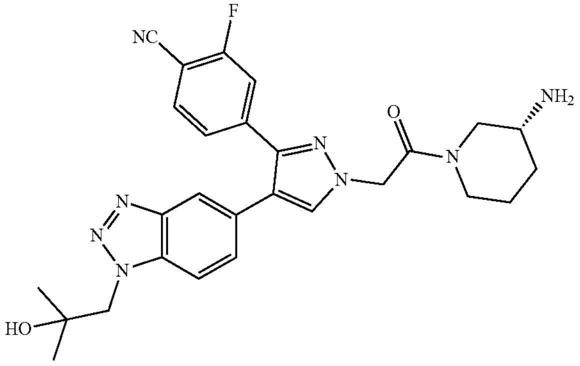

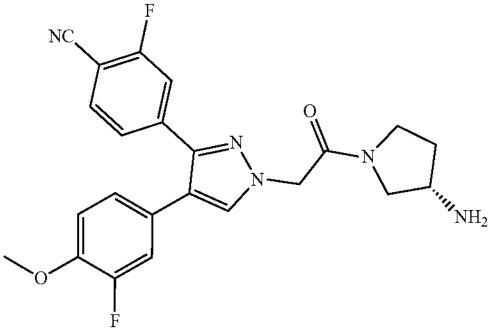

-continued

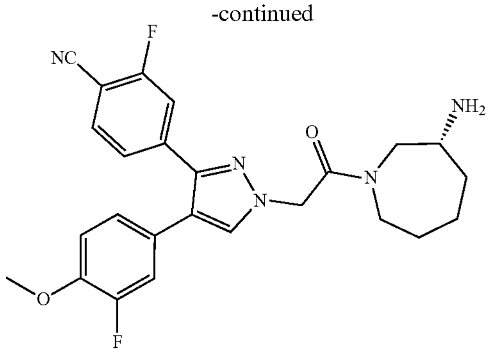

or

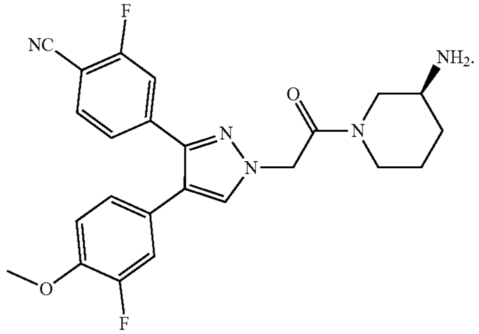

13. The compound or the pharmaceutically acceptable salt thereof as defined in claim 1, wherein the pharmaceutically acceptable salt is hydrochloride.

14. A pharmaceutical composition, which comprises the compound or the pharmaceutically acceptable salt thereof as defined in claim 1, and one or more pharmaceutically acceptable carriers.

15. A method for inhibiting LSD1 in-vitro, in-vivo or ex-vivo, which comprises administering the compound or the pharmaceutically acceptable salt thereof as defined in claim 1 in a sufficient amount to inhibit LSD1.

16. A method for treating a subject who has a disease associated with LSD1, which comprises administering to the subject a therapeutically effective amount of the compound or the pharmaceutically acceptable salt thereof as defined in claim 1.

17. A method for treating a subject who has a cancer, which comprises administering to the subject a therapeutically effective amount of the compound or the pharmaceutically acceptable salt thereof as defined in claim 1.

18. The method for treating a subject according to claim 17, wherein the cancer is acute myeloid leukemia (AML), acute lymphoblastic leukemia (ALL), small cell lung cancer (SCLC), non-small cell lung cancer (NSCLC), adult neuroblastoma, small round blue cell tumor, glioblastoma, prostate cancer, breast cancer, ovarian cancer, gastrointestinal cancer, liver cancer, bladder cancer, lung cancer, and/or melanoma.

* * * * *